US012735738B2

(12) United States Patent
Belhocine et al.

(10) Patent No.: US 12,735,738 B2
(45) Date of Patent: Sep. 15, 2026

(54) CIRCULAR PROBES AND METHODS FOR SAMPLE ANALYSIS

(71) Applicant: 10x Genomics, Inc., Pleasanton, CA (US)

(72) Inventors: Zahra Kamila Belhocine, Pleasanton, CA (US); Justin Costa, Union City, CA (US); Eswar Prasad Ramachandran Iyer, Sunnyvale, CA (US)

(73) Assignee: 10X GENOMICS, INC., Pleasanton, CA (US)

( * ) Notice: Subject to any disclaimer, the term of this patent is extended or adjusted under 35 U.S.C. 154(b) by 702 days.

(21) Appl. No.: 17/993,793

(22) Filed: Nov. 23, 2022

(65) Prior Publication Data

US 2023/0159997 A1 May 25, 2023

Related U.S. Application Data

(60) Provisional application No. 63/283,213, filed on Nov. 25, 2021.

(51) Int. Cl.
*C12Q 1/68* (2018.01)
*C12Q 1/682* (2018.01)
*C12Q 1/6841* (2018.01)
*C12Q 1/6844* (2018.01)

(52) U.S. Cl.
CPC .......... *C12Q 1/6841* (2013.01); *C12Q 1/682* (2013.01); *C12Q 1/6844* (2013.01)

(58) Field of Classification Search
None
See application file for complete search history.

(56) References Cited

U.S. PATENT DOCUMENTS 4,318,846 A 3/1982 Khanna et al.
4,683,195 A 7/1987 Mullis et al.
4,683,202 A 7/1987 Mullis
4,757,141 A 7/1988 Fung et al.
4,800,159 A 1/1989 Mullis et al.
4,849,336 A 7/1989 Miyoshi et al.
4,965,188 A 10/1990 Mullis et al.
5,066,580 A 11/1991 Lee
5,091,519 A 2/1992 Cruickshank
5,151,507 A 9/1992 Hobbs et al.
5,188,934 A 2/1993 Menchen
5,198,537 A 3/1993 Huber et al.
5,344,757 A 9/1994 Holtke et al.
5,354,657 A 10/1994 Boehringer et al.
5,366,860 A 11/1994 Bergot et al.
5,512,462 A 4/1996 Cheng
5,599,675 A 2/1997 Brenner
5,635,352 A 6/1997 Urdea et al.
5,688,648 A 11/1997 Mathies
5,695,940 A 12/1997 Drmanac et al.
5,702,888 A 12/1997 Holtke et al.
5,750,341 A 5/1998 Macevicz
5,800,996 A 9/1998 Lee et al.
5,847,162 A 12/1998 Lee et al.
5,990,479 A 11/1999 Weiss et al.
6,054,274 A 4/2000 Sampson et al.
6,172,218 B1 1/2001 Brenner
6,207,392 B1 3/2001 Weiss et al.
6,251,303 B1 6/2001 Bawendi et al.
6,265,552 B1 7/2001 Schatz
6,291,187 B1 9/2001 Kingsmore et al.
6,306,597 B1 10/2001 Macevicz
6,319,426 B1 11/2001 Bawendi et al.
6,322,901 B1 11/2001 Bawendi et al.
6,323,009 B1 11/2001 Lasken et al.
6,344,329 B1 2/2002 Lizardi et al.
6,368,801 B1 4/2002 Faruqi
6,391,937 B1 5/2002 Beuhler et al.
6,423,551 B1 7/2002 Weiss et al.
6,426,513 B1 7/2002 Bawendi et al.
6,444,143 B2 9/2002 Bawendi et al.
(Continued)

FOREIGN PATENT DOCUMENTS

WO WO 1991/017160 11/1991
WO WO 2014/163886 10/2014
(Continued)

OTHER PUBLICATIONS

Archer et al., "Selective and flexible depletion of problematic sequences from RNA-seq libraries at the cDNA stage," BMC Genomics. (2014) 15(1):401.
Baner et al., "Signal amplification of padlock probes by rolling circle replication," Nucleic Acids Res. (1998) 26(22):5073-5078.
Bibikova et al., "Quantitative gene expression profiling in formalin-fixed, paraffin-embedded tissues using universal bead arrays," Am J Pathol. Nov. 2004;165(5):1799-807.
Bolognesi et al., "Multiplex Staining by Sequential Immunostaining and Antibody Removal on Routine Tissue Sections," J. Histochem. Cytochem. (2017); 65(8): 431-444.
Capodieci et al., "Gene expression profiling in single cells within tissue," Nat Methods. (2005) 2(9): 663-5.
Chemeris et al., "Real-time hybridization chain reaction," Dokl Biochem Biophys. (2008) 419: 53-55.
Chen et al., "Nanoscale imaging of RNA with expansion microscopy," Nat Methods. (2016) 13:679-684.
(Continued)

*Primary Examiner* — Suryaprabha Chunduru
(74) *Attorney, Agent, or Firm* — MORRISON & FOERSTER LLP

(57) ABSTRACT

The present disclosure relates in some aspects to methods and compositions for analyzing a target nucleic acid, such as in situ detection of a region of interest in a polynucleotide in a cell or tissue sample. In some aspects, provided herein are circular probes (e.g., dumbbell probes) for analyzing a target nucleic acid, as well as methods comprising an enzymatic treatment to de-circularize unbound or non-specifically bound circular probes. Circular probes specifically bound to target nucleic acids remain intact during and after the enzymatic treatment and can be detected, e.g., via rolling circle amplification (RCA) of the circular probes and detection of the RCA products.

20 Claims, 4 Drawing Sheets

(56) References Cited

U.S. PATENT DOCUMENTS 6,534,266 B1 3/2003 Singer
6,576,291 B2 6/2003 Bawendi et al.
6,828,109 B2 12/2004 Kaplan et al.
6,969,488 B2 11/2005 Bridgham et al.
7,057,026 B2 6/2006 Barnes et al.
7,255,994 B2 8/2007 Lao
7,264,929 B2 9/2007 Rothberg et al.
7,345,159 B2 3/2008 Ju et al.
7,473,767 B2 1/2009 Dimitrov
7,534,991 B2 5/2009 Miller et al.
7,544,794 B1 6/2009 Benner
7,555,155 B2 6/2009 Levenson et al.
7,566,537 B2 7/2009 Balasubramanian et al.
7,632,641 B2 12/2009 Dirks et al.
7,655,898 B2 2/2010 Miller
7,721,721 B1 5/2010 Kronengold et al.
7,893,227 B2 2/2011 Wu et al.
7,910,304 B2 3/2011 Drmanac
7,941,279 B2 5/2011 Hwang et al.
7,989,166 B2 8/2011 Koch et al.
8,124,751 B2 2/2012 Pierce et al.
8,133,672 B2 3/2012 Bjornson et al.
8,199,999 B2 6/2012 Hoyt et al.
8,257,954 B2 9/2012 Clark et al.
8,268,554 B2 9/2012 Schallmeiner
8,330,087 B2 12/2012 Domenicali
8,343,746 B2 1/2013 Rank et al.
8,415,102 B2 4/2013 Geiss et al.
8,431,691 B2 4/2013 McKernan et al.
8,460,865 B2 6/2013 Chee et al.
8,462,981 B2 6/2013 Determan et al.
8,481,258 B2 7/2013 Church et al.
8,519,115 B2 8/2013 Webster et al.
8,551,710 B2 10/2013 Bernitz et al.
8,632,975 B2 1/2014 Vander Horn et al.
8,658,361 B2 2/2014 Wu et al.
8,658,365 B2 2/2014 Bjornson et al.
8,771,950 B2 7/2014 Church et al.
8,921,086 B2 12/2014 Hanzel et al.
8,986,926 B2 3/2015 Ferree et al.
9,201,063 B2 12/2015 Sood et al.
9,217,178 B2 12/2015 Fedurco et al.
9,273,349 B2 3/2016 Nguyen et al.
9,279,155 B2 3/2016 Bjornson et al.
9,371,563 B2 6/2016 Geiss et al.
9,371,598 B2 6/2016 Chee
9,376,717 B2 6/2016 Gao et al.
9,512,422 B2 12/2016 Barnard et al.
9,541,504 B2 1/2017 Hoyt
9,551,032 B2 1/2017 Landegren et al.
9,624,538 B2 4/2017 Church et al.
9,650,406 B2 5/2017 Zhou et al.
9,714,446 B2 7/2017 Webster et al.
9,714,937 B2 7/2017 Dunaway
9,727,810 B2 8/2017 Fodor et al.
9,778,155 B2 10/2017 Gradinaru et al.
9,783,841 B2 10/2017 Nolan et al.
9,889,422 B2 2/2018 Smith et al.
9,909,167 B2 3/2018 Samusik et al.
10,032,064 B2 7/2018 Hoyt
10,059,990 B2 8/2018 Boyden et al.
10,126,242 B2 11/2018 Miller et al.
10,138,509 B2 11/2018 Church et al.
10,179,932 B2 1/2019 Church et al.
10,227,639 B2 3/2019 Levner et al.
10,246,700 B2 4/2019 Dunaway et al.
10,266,888 B2 4/2019 Daugharthy et al.
10,267,808 B2 4/2019 Cai
10,309,879 B2 6/2019 Chen et al.
10,317,321 B2 6/2019 Tillberg et al.
10,364,457 B2 7/2019 Wassie et al.
10,370,698 B2 8/2019 Nolan et al.
10,415,080 B2 9/2019 Dunaway et al.
10,457,980 B2 10/2019 Cai et al.
10,465,235 B2 11/2019 Gullberg et al.
10,494,662 B2 12/2019 Church et al.
10,495,554 B2 12/2019 Deisseroth et al.
10,501,777 B2 12/2019 Beechem et al.
10,501,791 B2 12/2019 Church et al.
10,510,435 B2 12/2019 Cai et al.
10,526,649 B2 1/2020 Chen et al.
10,545,075 B2 1/2020 Deisseroth et al.
10,550,429 B2 2/2020 Harada et al.
10,580,128 B2 3/2020 Miller
10,640,816 B2 5/2020 Beechem et al.
10,640,826 B2 5/2020 Church et al.
10,669,569 B2 6/2020 Gullberg et al.
10,746,981 B2 8/2020 Tomer et al.
10,774,372 B2 9/2020 Chee et al.
10,774,374 B2 9/2020 Frisén et al.
10,794,802 B2 10/2020 Gradinaru et al.
10,802,262 B2 10/2020 Tomer et al.
10,815,519 B2 10/2020 Husain et al.
10,829,814 B2 11/2020 Fan et al.
10,844,426 B2 11/2020 Daugharthy et al.
10,858,698 B2 12/2020 Church et al.
10,872,679 B2 12/2020 Cai et al.
10,964,001 B2 3/2021 Miller
11,174,281 B1 11/2021 Graham et al.
11,287,422 B2 3/2022 Previte et al.
11,434,525 B2 9/2022 Glezer
11,459,603 B2 10/2022 Tyagi et al.
11,499,185 B2 11/2022 Vijayan et al.
11,643,679 B2 5/2023 Glezer et al.
11,999,999 B2 6/2024 Ju et al.
2002/0045045 A1 4/2002 Adams et al.
2003/0017264 A1 1/2003 Treadway et al.
2005/0100900 A1 5/2005 Kawashima et al.
2006/0188901 A1 8/2006 Barnes et al.
2006/0234261 A1 10/2006 Pierce et al.
2006/0240439 A1 10/2006 Smith et al.
2006/0281109 A1 12/2006 Barr et al.
2007/0166705 A1 7/2007 Milton et al.
2009/0118128 A1 5/2009 Liu et al.
2010/0055733 A1 3/2010 Lutolf et al.
2011/0059865 A1 3/2011 Smith et al.
2011/0223585 A1 9/2011 Gullberg et al.
2012/0270305 A1 10/2012 Reed et al.
2013/0079232 A1 3/2013 Kain et al.
2013/0260372 A1 10/2013 Buermann et al.
2013/0288249 A1 10/2013 Gullbert
2013/0323729 A1 12/2013 Landegren et al.
2014/0194311 A1 7/2014 Gullberg et al.
2016/0024555 A1 1/2016 Church et al.
2016/0108458 A1 4/2016 Frei et al.
2016/0305856 A1 10/2016 Boyden et al.
2016/0369329 A1 12/2016 Cai et al.
2016/0376642 A1 12/2016 Landegren et al.
2017/0009278 A1 1/2017 Söderberg et al.
2017/0081489 A1 3/2017 Rodriques et al.
2017/0101672 A1 4/2017 Luo et al.
2017/0219465 A1 8/2017 Desseroth et al.
2017/0220733 A1 8/2017 Zhuang et al.
2017/0253918 A1 9/2017 Kohman
2018/0052081 A1 2/2018 Kohman
2018/0080876 A1 3/2018 Rockel et al.
2018/0208967 A1 7/2018 Larman et al.
2018/0237864 A1 8/2018 Imler et al.
2018/0251833 A1 9/2018 Daugharthy et al.
2018/0320226 A1 11/2018 Church et al.
2019/0017106 A1 1/2019 Frisen et al.
2019/0032121 A1 1/2019 Daugharthy et al.
2019/0032128 A1 1/2019 Chen et al.
2019/0055594 A1 2/2019 Samusik et al.
2019/0106733 A1 4/2019 Kishi et al.
2019/0112599 A1 4/2019 Church et al.
2019/0119735 A1 4/2019 Deisseroth et al.
2019/0155835 A1 5/2019 Daugharthy et al.
2019/0161796 A1 5/2019 Hauling et al.
2019/0177718 A1* 6/2019 Church ................ C12Q 1/6874
2019/0177800 A1 6/2019 Boutet et al.
2019/0194709 A1 6/2019 Church et al.
2019/0218608 A1 7/2019 Daugharthy et al.
2019/0249248 A1 8/2019 Beechem et al.

(56) References Cited

U.S. PATENT DOCUMENTS

2019/0264270 A1 8/2019 Zhuang et al.
2019/0271028 A1 9/2019 Khafizov et al.
2019/0276881 A1 9/2019 Zhuang et al.
2019/0339203 A1 11/2019 Miller et al.
2019/0367969 A1 12/2019 Belhocine
2019/0376956 A1 12/2019 Bobrow et al.
2020/0010891 A1 1/2020 Beechem et al.
2020/0071751 A1 3/2020 Daugharthy et al.
2020/0123597 A1 4/2020 Daniel
2020/0140920 A1 5/2020 Pierce et al.
2020/0224243 A1 7/2020 Desai et al.
2020/0224244 A1* 7/2020 Nilsson ................ C12Q 1/6806
2020/0239946 A1 7/2020 Dewal
2020/0354774 A1 11/2020 Church et al.
2020/0354782 A1 11/2020 Dewal
2020/0362398 A1 11/2020 Kishi et al.
2020/0393343 A1 12/2020 Kennedy-Darling et al.
2020/0399689 A1 12/2020 Luo et al.
2021/0017587 A1 1/2021 Cai et al.
2021/0115504 A1 4/2021 Cai et al.
2021/0164039 A1 6/2021 Wang et al.
2021/0222234 A1 7/2021 Carlson
2021/0238662 A1 8/2021 Bava
2021/0238674 A1 8/2021 Bava
2021/0254140 A1 8/2021 Stahl et al.
2021/0262018 A1 8/2021 Bava et al.
2021/0277460 A1 9/2021 Bava
2021/0340621 A1 11/2021 Daugharthy et al.
2021/0388423 A1 12/2021 Bava et al.
2021/0388424 A1 12/2021 Bava
2022/0026433 A1 1/2022 Guo et al.
2022/0049302 A1 2/2022 Daugharthy et al.
2022/0049303 A1 2/2022 Busby et al.
2022/0083832 A1 3/2022 Shah
2022/0084628 A1 3/2022 Shah
2022/0084629 A1 3/2022 Shah
2022/0128565 A1 4/2022 Miller et al.
2022/0136049 A1 5/2022 Bava et al.
2022/0186300 A1 6/2022 Bava
2022/0195498 A1 6/2022 Kuhnemund et al.
2022/0213529 A1 7/2022 Kuhnemund et al.
2022/0228200 A1 7/2022 Bava
2022/0235403 A1 7/2022 Costa
2022/0282306 A1 9/2022 Bava et al.
2022/0282316 A1 9/2022 Bava
2022/0282319 A1 9/2022 Verheyen
2022/0372570 A1 11/2022 Costa
2022/0380838 A1 12/2022 Kuhnemund et al.
2022/0403458 A1 12/2022 Bava
2023/0002808 A1 1/2023 Mignardi
2023/0012607 A1 1/2023 Kuhnemund et al.
2023/0013775 A1 1/2023 Chen et al.
2023/0015226 A1 1/2023 Chen et al.
2023/0026886 A1 1/2023 Chen
2023/0031305 A1 2/2023 Hernandez Neuta et al.
2023/0031996 A1 2/2023 Hernandez Neuta et al.
2023/0035685 A1 2/2023 Hernandez Neuta et al.
2023/0037182 A1 2/2023 Bava et al.
2023/0039148 A1 2/2023 Verheyen
2023/0041485 A1 2/2023 Hernandez Neuta et al.
2023/0044650 A1 2/2023 Dockter
2023/0057571 A1 2/2023 Costa et al.
2023/0061542 A1 3/2023 Kuhnemund
2023/0084407 A1 3/2023 Hernandez Neuta et al.
2023/0159997 A1 5/2023 Belhocine et al.
2023/0160794 A1 5/2023 Dockter et al.
2023/0183787 A1 6/2023 Bava et al.
2023/0242974 A1 8/2023 Costa et al.
2023/0279465 A1 9/2023 He et al.
2023/0279475 A1 9/2023 Kuhnemund et al.
2023/0279480 A1 9/2023 Kuhnemund
2023/0287478 A1 9/2023 Bava
2023/0314327 A1 10/2023 Hoffman
2023/0314328 A1 10/2023 Costa
2023/0323427 A1 10/2023 Schnall-Levin
2023/0323430 A1 10/2023 Shastry
2023/0323437 A1 10/2023 Chen et al.
2023/0374573 A1 11/2023 Qian et al.
2023/0374580 A1 11/2023 Costa
2023/0416821 A1 12/2023 Bava et al.
2024/0002902 A1 1/2024 Jakobsen et al.
2024/0026426 A1 1/2024 Bava
2024/0026427 A1 1/2024 Kuhnemund et al.
2024/0026439 A1 1/2024 Sasaki
2024/0026448 A1 1/2024 Costa
2024/0035070 A1 2/2024 Christopherson
2024/0035071 A1 2/2024 Delaney et al.
2024/0035072 A1 2/2024 Christopherson
2024/0043910 A1 2/2024 Shastry
2024/0043914 A1 2/2024 Chen et al.
2024/0060119 A1 2/2024 Bava
2024/0084373 A1 3/2024 Shastry
2024/0084378 A1 3/2024 Marks et al.
2024/0101978 A1 3/2024 Boghospor et al.
2024/0132938 A1 4/2024 Kuhnemund
2024/0141418 A1 5/2024 Mielinis
2024/0150816 A1 5/2024 Feng et al.
2024/0158852 A1 5/2024 Belhocine et al.
2024/0167081 A1 5/2024 Bava et al.
2024/0175082 A1 5/2024 Costa
2024/0175083 A1 5/2024 Bava et al.
2024/0191297 A1 6/2024 Christopherson et al.
2024/0209330 A1 6/2024 Shastry et al.
2024/0218424 A1 7/2024 Costa et al.
2024/0218437 A1 7/2024 Belhocine et al.
2024/0263219 A1 8/2024 Kuhnemund
2024/0263220 A1 8/2024 Olofsson
2024/0264155 A1 8/2024 Costa

FOREIGN PATENT DOCUMENTS

WO WO 2017/079406 5/2017
WO WO 2017/143155 8/2017
WO WO 2018/026873 2/2018
WO WO 2019/199579 10/2019
WO WO 2019/236841 12/2019
WO WO 2020/076976 4/2020
WO WO 2020/076979 4/2020
WO WO 2020/096687 5/2020
WO WO 2020/099640 5/2020
WO WO 2020/117914 6/2020
WO WO 2020/123316 6/2020
WO WO 2020/123742 6/2020
WO WO 2020/142490 7/2020
WO WO 2020/240025 12/2020
WO WO 2020/254519 12/2020
WO WO 2021/123282 6/2021
WO WO 2021/123286 6/2021
WO WO 2021/138676 7/2021
WO WO 2021/155063 8/2021
WO WO 2021/168326 8/2021
WO WO 2023/108139 6/2023
WO WO 2023/141476 7/2023
WO WO 2023/172915 9/2023
WO WO 2023/192302 10/2023
WO WO 2024/148300 7/2024

OTHER PUBLICATIONS

Chen et al., "Expansion Microscopy," Science (2015) 347(6221):543-548.

Choi et al., "Programmable in situ amplification for multiplexed imaging of mRNA expression," Nat Biotechnol. (2010) 28(11): 1208-1212.

Conze et al., "Single molecule analysis of combinatorial splicing," Nucleic Acids Res. (2010) 38(16): e163.

Dean et al., "Rapid Amplification Of Plasmid And Phage DNA Using Phi29 DNA Polymerase And Multiply-Primed Rolling Circle Amplification," Genome Research (2001) 11:1095-1099.

Dirks et al., "Triggered amplification by hybridization chain reaction," Proc Natl Acad Sci USA. (2004) 101(43): 15275-15278.

Eng et al., "Transcriptome-scale super-resolved imaging in tissues by RNA seqFISH," Nature. (2019) 568(7751): 235-239.

(56) References Cited

OTHER PUBLICATIONS

Fang et al., "Fluoride-Cleavable Biotinylation Phosphoramidite for 5'-end-Labelling and Affinity Purification of Synthetic Oligonucleotides," Nucleic Acids Res. (2003) 31(2): 708-715.
Faruqi et al., "High-throughput genotyping of single nucleotide polymorphisms with rolling circle amplification," BMC Genomics. (2001) 2:4.
Femino et al., "Visualization of single RNA transcripts in situ," Science. (1998) 280(5363): 585-90.
Gavrilovic et al., "Automated classification of multicolored rolling circle products in dual-channel wide-field fluorescence microscopy," Cytometry A. (2011) 79(7): 518-27.
Geiss et al., "Direct multiplexed measurement of gene expression with color-coded probe pairs," Nat Biotechnol. (2008) 26(3): 317-25.
Glass et al., "SIMPLE: a sequential immunoperoxidase labeling and erasing method," J Histochem Cytochem. (2009) 57(10); 899-905.
Goh, J.J.L. et al. (Jul. 2020, e-pub. Jun. 15, 2020). "Highly Specific Multiplexed RNA Imaging In Tissues With Split-FISH," Nat Methods 17(7):689-693. doi: 10.1038/s41592-020-0858-0. Epub Jun. 15, 2020.
Goransson et al., "A single molecule array for digital targeted molecular analyses," Nucleic Acids Res. 2009 37(1):e7. doi: 10.1093/nar/gkn921.
Gunderson et al. "Decoding randomly ordered DNA arrays." Genome research 14.5 (2004): 870-877.
Gyllborg et al., "Hybridization-based in situ sequencing (HybISS) for spatially resolved transcriptomics in human and mouse brain tissue," Nucleic Acids Res. (2020) 48(19): e112.
Han et al., "Quantum-dot-tagged microbeads for multiplexed optical coding of biomolecules," Nat Biotechnol. (2001) 19(7): 631-5.
Henegariu et al., "Custom fluorescent-nucleotide synthesis as an alternative method for nucleic acid labeling," Nature Biotechnol. (2000) 18:345.
Itzkovitz et al., "Single-molecule transcript counting of stem-cell markers in the mouse intestine," Nat Cell Biol. (2011) 14(1): 106-14.
Itzkovitz et al., "Validating Transcripts with Probes and Imaging Technology," Nat Methods. (2011) 8(4 Suppl): S12-S19.
Jamur et al., "Permeabilization of cell membranes," Method Mol. Biol. (2010) 588: 63-66 (abstract only).
Ke et al., "In situ sequencing for RNA analysis in preserved tissue and cells," Nat Methods. (2013) 10(9):857-60.
Korlach et al. "Selective aluminum passivation for targeted immobilization of single DNA polymerase molecules in zero-mode waveguide nanostructures." *Proceedings of the National Academy of Sciences* 105.4 (2008): 1176-1181.
Lagunavicius et al., "Novel application of Phi29 DNA polymerase: RNA detection and analysis in vitro and in situ by target RNA-primed RCA," RNA. (2009) 15(5):765-71.
Lakowicz et al., "Silver particles enhance emission of fluorescent DNA oligomers," Bio Techniques (2003) 34(1); 62-66.
Larsson et al. "In situ detection and genotyping of individual mRNA molecules," Nat Methods. (2010) 7(5):395-397.
Lee et al. "Highly Multiplexed Subcellular RNA Sequencing In Situ", Science (2014) 343(6177):1360-1363.
Levene et al. "Zero-mode waveguides for single-molecule analysis at high concentrations." *science* 299.5607 (2003): 682-686.
Levsky et al., "Fluorescence in situ hybridization: past, present and future," J Cell Sci. (2003) 116(Pt 14): 2833-8.
Levsky et al., "Single-cell gene expression profiling," Science. (2002) 297(5582): 836-40.
Lin et al., "Highly multiplexed imaging of single cells using a high-throughput cyclic immunofluorescence method," Nat Commun. (2015) 6:8390.
Liu et al. Barcoded oligonucleotides ligated on RNA amplified for multiplexed and parallel in situ analyses. Nucleic Acids Res. (2021) 49(10):e58, 15 pages. doi: 10.1093/nar/gkab120.
Lizardi et al., "Mutation detection and single-molecule counting using isothermal rolling-circle amplification," Nat Genet. (1998) 19(3): 225-232.
Lundquist et al. "Parallel confocal detection of single molecules in real time." Optics letters 33.9 (2008): 1026-1028.
Maierhorfer et al., "Multicolor deconvolution microscopy of thick biological specimens," Am J Pathol. (2003) 162(2): 373-9.
McGinn et al., "New technologies for DNA analysis—a review of the READNA Project," N Biotechnol. (2016) 33(3): 311-30. doi: 10.1016/j.nbt.2015.10.003.
Meade et al. "Multiplexed DNA detection using spectrally encoded porous SiO2 photonic crystal particles," Anal Chem. (2009) 81(7): 2618-25.
Mitra et al., "Fluorescent in situ sequencing on polymerase colonies," Anal. Biochem. (2003) 320, 55-65.
Moffitt et al., "RNA Imaging with Multiplexed Error-Robust Fluorescence In Situ Hybridization (MERFISH)," Methods in Enzymology, (2016) 572; 1-49.
Mohsen et al., "The Discovery of Rolling Circle Amplification and Rolling Circle Transcription," Acc Chem Res. (2016) 49(11): 2540-2550.
Nallur et al., "Signal amplification by rolling circle amplification on DNA microarrays," Nucleic Acids Res. (2001) 29(23): e118.
Niu et al., "Fluorescence detection for DNA using hybridization chain reaction with enzyme-amplification," Chem Commun (Camb). (2010) 46(18): 3089-91.
Nudt China, "Development of A Novel Blood-MicroRNA Handy Detection System with CRISPR," (2016) https://2016.igem.org/Team:NUDT_CHINA/Design.
Payne et al. "In situ genome sequencing resolves DNA sequence and structure in intact biological samples," Science. (2021) 371(6532): eaay3446. doi: 10.1126/science.aay3446. Epub Dec. 31, 2020.
Pirici et al., "Antibody elution method for multiple immunohistochemistry on primary antibodies raised in the same species and of the same subtype," J Histochem Cytochem. (2009) 57(6); 567-75.
Raj et al., "Imaging individual mRNA molecules using multiple singly labeled probes," Nat Methods. (2008) 5(10): 877-879.
Rouhanifard et al. "ClampFISH detects individual nucleic acid molecules using click chemistry-based amplification," Nat Biotechnol. (2018) 17 pages. doi: 10.1038/nbt.4286.
Schweitzer et al. "Immunoassays with rolling circle DNA amplification: A versatile platform for ultrasensitive antigen detection," Proc. Natl Acad. Sci. USA (2000) 97:10113-119.
Schweitzer et al., "Multiplexed protein profiling on microarrays by rolling-circle amplification," Nature Biotech. (2002) 20:359-365.
Shendure et al., "Accurate multiplex polony sequencing of an evolved bacterial genome," Science (2005) 309(5741); 1728-1732.
Song et al., "Hybridization chain reaction-based aptameric system for the highly selective and sensitive detection of protein," Analyst. (2012) 137(6):1396-1401.
Sun et al., "Composite organic-inorganic nanoparticles as Raman labels for tissue analysis," Nano Lett. (2007) 7(2): 351-6.
Stougaard et al. "In situ detection of non-polyadenylated RNA molecules using Turtle Probes and target primed rolling circle PRINS." Bmc Biotechnol. (2007) 7:69.
Takahashi et al., "RNase H-assisted RNA-primed rolling circle amplification for targeted RNA sequence detection," Sci Rep. (2018) 8(1):7770.
Takei et al., (Feb. 2021, e-pub Jan. 27, 2021). "Integrated Spatial Genomics Reveals Global Architecture Of Single Nuclei," Nature 590(7845):344-350, 53 pages. doi: 10.1038/s41586-020-03126-2.
Vandernoot et al., "cDNA normalization by hydroxyapatite chromatography to enrich transcriptome diversity in RNA-seq applications," Biotechniques, (2012) 53(6) 373-80.
Wählby et al., "Sequential immunofluorescence staining and image analysis for detection of large Nos. of antigens in individual cell nuclei," Cytometry. (2002) 47(1): 32-41.
Wang et al., "Three-dimensional intact-tissue sequencing of single-cell transcriptional states," Science. (2018) 361(6400): eaat5691.
Weibrecht et al., "Simultaneous visualization of both signaling cascade activity and end-point gene expression in single cells," PLoS One. (2011) 6(5): e20148.

(56) References Cited

OTHER PUBLICATIONS

Wetmur, "DNA Probes: Applications of the Principles of Nucleic Acid Hybridization," Critical Reviews in Biochemistry and Molecular Biology, (1991) 26(91); 227-259.
Wilson et al., "Encoded microcarriers for high-throughput multiplexed detection," Angew Chem Int Ed Engl. (2006) 18;45(37): 6104-17.
Wu, C. et al. "RollFISh Achieves Robust Quantification Of Single-Molecule RNA Biomarkers In Paraffin-Embedded Tumor Tissue Samples," Commun Biol. (2018) 1:(209):1-8. doi: 10.1038/s42003-018-0218-0.
Xia et al. "Multiplexed detection of RNA using MERFISH and branched DNA amplification." Scientific reports 9.1 (2019): 1-13.
Zhao et al., "Advances of multiplex and high throughput biomolecular detection technologies based on encoding microparticles," Sci China Chem. (2011) 54(8):1185.
Chen et al., "Efficient in situ barcode sequencing using padlock probe-based BaristaSeq," Nucleic Acids Res. (2018) 46(4): e22.
Sun et al., "Integrating barcoded neuroanatomy with spatial transcriptional profiling enables identification of gene correlates of projections," Nat Neurosci. (2021) 24(6):873-885.

* cited by examiner

CIRCULAR PROBES AND METHODS FOR SAMPLE ANALYSIS

CROSS-REFERENCE TO RELATED APPLICATIONS

This application claims priority to U.S. Provisional Patent Application No. 63/283,213, filed on Nov. 25, 2021, entitled "CIRCULAR PROBES AND METHODS FOR SAMPLE ANALYSIS," which is herein incorporated by reference in its entirety for all purposes.

FIELD

The present disclosure generally relates to methods and compositions for in situ detection of analytes in a sample, such as in situ detection of a region of interest in a target nucleic acid or a reporter oligonucleotide in a cell or a cell or tissue sample.

BACKGROUND

Methods are available for analyzing nucleic acids present in a biological sample, such as a cell or a tissue. Current methods of oligonucleotide probe-based assay methods for in situ analysis may suffer from low sensitivity, specificity, and/or detection efficiency and may require careful and laborious optimization. Thus, improved methods for analyzing nucleic acids present in a biological sample are needed. Provided herein are methods, compositions, and kits that meet such and other needs.

BRIEF SUMMARY

Provided herein are methods of analyzing a biological sample. In some aspects, provided herein are circular probes and methods of using the circular probes for detecting a region of interest in a target nucleic acid molecule such as a target RNA molecule. In some embodiments, by pre-circularizing a probe before it is hybridized to a target nucleic acid molecule in a sample, there is no need for target-templated ligation (e.g., in situ RNA-templated probe ligation) in order to circularize the hybridized probe. In one aspect, probe ligation outside a biological sample such as a tissue section can be more efficient than in situ ligation. In another aspect, the circular probe can be pre-formed by assembling two or more shorter probe oligonucleotides. Since each probe oligonucleotide can be synthesized at a higher accuracy than the base-by-base synthesis of the longer full-length probe, the overall accuracy of the circular probe can be improved. In yet another aspect, in cases where probes are designed to hybridize to target RNA molecules directly, false positive signals associated with incorrectly ligated probes due to the low fidelity of RNA-templated ligases in situ may be reduced by pre-circularizing the probes using DNA-templated ligation.

Certain existing methods utilize in situ ligation to increase detection specificity, where specifically hybridized probes can be ligated and remain hybridized for subsequent in situ amplification, whereas under the same conditions non-specifically hybridized probes are either not ligated (e.g., due to discrimination by a ligase) and/or are less stably hybridized to the target sequence than a specifically hybridized and ligated probe. While in some aspects the methods disclosed herein avoid in situ ligation in order to improve direct-RNA detection sensitivity, the methods can still maintain high specificity. In some embodiments, the methods disclosed herein comprise cleaving and/or degrading unbound or non-specifically bound circular probes while leaving specifically hybridized circular probes intact for subsequent detection, e.g., by rolling circle amplification of the circular probes. In some embodiments, a circular probe disclosed herein comprises a duplex stem region comprising one or more ribonucleotides in the strand that hybridizes to a target RNA molecule. Upon probe hybridization to the target RNA molecule, the duplex stem region can be unwound (e.g., via branch migration and invasion of a target RNA sequence to displace the other strand of the duplex) such that the target RNA molecule hybridizes to the strand comprising the one or more ribonucleotides. The hybridization can be performed under stringent conditions, and non-specific or unbound probes can be removed by one or more stringent washes. Further, in cases where some non-specific or unbound probes remain in the sample, an enzymatic or chemical treatment (e.g., with an RNAse H) can be used to cleave and/or degrade the unbound or non-specifically bound circular probes but not the specifically hybridized circular probes. Thus, false positive signals due to unbound or non-specifically bound circular probes can be reduced.

In some aspects, provided herein is a method for analyzing a biological sample, comprising: (a) contacting the biological sample comprising a nucleic acid molecule with a circular probe, wherein: the circular probe comprises a stem region and a loop region, the stem region comprises (i) a first strand comprising one or more ribonucleotides and (ii) a second strand complementary to the first strand, and a sequence in the loop region hybridizes to a first sequence in the nucleic acid molecule; (b) hybridizing the nucleic acid molecule to the first strand of the stem region, wherein: if a second sequence in the nucleic acid molecule is complementary to the first strand, the second strand is displaced from the first strand, the circular probe hybridizes to at least the first and second sequences in the nucleic acid molecule, and the one or more ribonucleotides in the circular probe hybridize to complementary ribonucleotide(s) in the nucleic acid molecule; and (c) contacting the biological sample with an RNAse; (d) detecting a signal or absence thereof, wherein the signal is associated with the circular probe or a product thereof generated without de-circularizing the circular probe.

In some embodiments, if the second sequence in the nucleic acid molecule is not complementary to the first strand, the second strand may not be displaced from the first strand and the one or more ribonucleotides may be cleaved by the RNAse, thereby de-circularizing the circular probe. In any of the embodiments herein, the nucleic acid molecule may be an RNA.

In some embodiments, provided herein is a method for analyzing a biological sample, comprising: (a) contacting the biological sample comprising a plurality of nucleic acid molecules with a plurality of circular probes, wherein a circular probe of the plurality of circular probes comprises: (i) a stem region comprising (1) a first strand complementary to a nucleic acid molecule of the plurality of nucleic acid molecules, wherein the first strand comprises one or more ribonucleotides, and (2) a second strand complementary to the first strand; and (ii) a loop region comprising (1) a sequence complementary to a first sequence of the nucleic acid molecule; (b) hybridizing the loop region to the first sequence of the nucleic acid molecule; (c) displacing the second strand from the first strand and hybridizing the first strand to the nucleic acid molecule, thereby obtaining a hybridized circular probe; (d) contacting the biological sample with an RNAse, wherein the RNAse cleaves one or more ribonucleotides of a circular probe that is not hybridized to a nucleic acid molecule of the plurality of nucleic acid molecules; (e) performing a rolling circle amplification reaction on the hybridized circular probe to generate an amplified circular probe; and (f) detecting the amplified circular probe, thereby detecting the nucleic acid molecule in the biological sample.

In some embodiments, provided herein is a method for analyzing a biological sample, comprising: (a) contacting the biological sample comprising a first nucleic acid molecule and a second nucleic acid molecule with a circular probe, wherein the circular probe comprises: (i) a stem region comprising (1) a first strand complementary to the first nucleic acid molecule but not complementary to the second nucleic acid molecule, wherein the first strand comprises one or more ribonucleotides, and (2) a second strand complementary to the first strand; and (ii) a loop region comprising (1) a sequence complementary to a first sequence of the first and second nucleic acid molecules; (b) hybridizing the loop regions in molecules of the circular probe to the first sequences of the first and second nucleic acid molecules; (c) displacing the second strand from the first strand and hybridizing the first strand to the first nucleic acid molecule, thereby obtaining a first molecule of the circular probe with its first strand hybridized on the first nucleic acid molecule, wherein a second molecule of the circular probe hybridizes to the second nucleic acid molecule via its loop region and not via its first strand; (d) contacting the biological sample with an RNAse, wherein the RNAse cleaves one or more ribonucleotides of the first strand of the second molecule of the circular probe, whereas the first molecule of the circular probe remains circular; (e) performing a rolling circle amplification reaction on the first molecule of the circular probe to generate a rolling circle amplification product (RCP); and (f) detecting the RCP, thereby detecting the first nucleic acid molecule in the biological sample.

In some embodiments, the first and second nucleic acid molecules are not identical and may share about 10%, about 20%, about 30%, about 40%, about 50%, about 60%, about 70%, about 80%, about 90%, about 95%, or about 99% sequence homology. In some embodiments, the first strand of the circular probe forms a duplex with the first nucleic acid molecule without no unpaired base in the duplex region. In some embodiments, the first strand of the circular probe comprises one or more mismatches, one or more deletions, and/or one or more insertions, compared to the second nucleic acid molecule. In some embodiments, the one or more nucleotide differences are at nucleotide positions comprising the ribonucleotide(s) of the first strand of the circular probe. In some embodiments, the hybridization between the circular probe and the second nucleic acid molecule forms a complex comprising one or more unpaired bases, and this hybridization is disfavored over the hybridization between the complementary first and second strands in the stem region of the circular probe. In some embodiments, in the presence of the second nucleic acid molecule, the first strand of the circular probe remains hybridized to the complementary second strand (e.g., the ribonucleotide(s) of the first strand base-pairing with complementary deoxyribonucleotide(s) of the second strand) and is not hybridized to the second nucleic acid molecule. In some embodiments, the ribonucleotide(s) of the circular probe hybridized to the second nucleic acid molecule via the loop region is/are cleaved by the RNAse, whereas the ribonucleotide(s) of the circular probe hybridized to the first nucleic acid molecule via the loop region and the first strand of the stem region is/are not cleaved by the RNAse.

In some embodiments, the first sequence of the first nucleic acid molecule and the first sequence of the second nucleic acid molecule share about 10%, about 20%, about 30%, about 40%, about 50%, about 60%, about 70%, about 80%, about 90%, about 95%, or 100% sequence homology, whereas the second sequence of the first nucleic acid molecule and the second sequence of the second nucleic acid molecule comprise one or more nucleotide differences. In some embodiments, the first nucleic acid molecule is hybridized by the circular probe via the first strand as well as the loop region of the circular probe, whereas the second nucleic acid molecule is less specifically hybridized by the circular probe (e.g., via the loop region and not via the first strand of the circular probe). In some embodiments, the RNAse cleaves one or more ribonucleotides of the circular probe non-specifically (or less specifically) hybridized to the second nucleic acid molecule, whereas the circular probe specifically hybridized to the first nucleic acid molecule remains circular. Since the circular probe bound to the second nucleic acid molecule is linearized and cannot lead to the generation of an RCP, the first nucleic acid molecule can be detected in the biological sample while false positive signals associated with the second nucleic acid molecule are reduced or eliminated.

In some aspects, provided herein is a method for analyzing a biological sample, comprising: (a) contacting the biological sample comprising a plurality of nucleic acid molecules with a plurality of circular probes, wherein a first circular probe of the plurality of circular probes comprises: (i) a loop region comprising a sequence complementary to a first sequence of a first nucleic acid molecule of the plurality of nucleic acid molecules; and (ii) a stem region comprising (1) a first strand complementary to the first nucleic acid molecule, wherein the first strand comprises one or more ribonucleotides, and (2) a second strand complementary to the first strand; (b) hybridizing the loop region to the first sequence of the first nucleic acid molecule; (c) displacing the second strand from the first strand and hybridizing the first strand to the first nucleic acid molecule, thereby obtaining a hybridized circular probe; (d) contacting the biological sample with an RNAse, wherein the RNAse cleaves one or more ribonucleotides of a second circular probe of the plurality of circular probes that is not hybridized to a second nucleic acid molecule of the plurality of nucleic acid molecules; (e) performing a rolling circle amplification reaction on the hybridized circular probe to generate an amplification product; and (f) detecting the amplification product, thereby detecting the first nucleic acid molecule in the biological sample. In some embodiments, the second circular probe comprises a stem region comprising (1) a first strand complementary to the first nucleic acid molecule and not complementary to the second nucleic acid molecule, wherein the first strand comprises one or more ribonucleotides, and (2) a second strand complementary to the first strand.

In any of the embodiments herein, the second circular probe can comprise a loop region comprising a sequence complementary to the first sequence of the first nucleic acid molecule and/or complementary to a first sequence of the second nucleic acid molecule. In any of the embodiments herein, the first nucleic acid molecule may comprise a sequence of interest. In any of the embodiments herein, the second nucleic acid molecule may not comprise the sequence of interest, and the first strand of the second circular probe may not hybridize to the second nucleic acid molecule. In any of the embodiments herein, the sequence of interest can be of 1, 2, 3, 4, or 5 nucleotides in length or longer. In any of the embodiments herein, the sequence of interest or a portion thereof may be complementary to one or more of the ribonucleotide(s) in the first strand of the first circular probe. In any of the embodiments herein, the loop region of the first circular probe may comprise a first barcode sequence corresponding to the first nucleic acid molecule or a sequence of interest therein, and/or the loop region of the second circular probe may comprise a second barcode sequence corresponding to the second nucleic acid molecule or a sequence of interest therein. In any of the embodiments herein, the sequences of interest in the first and second nucleic acid molecules are different and the first and second barcode sequences may be different.

In any of the embodiments herein, the plurality of nucleic acid molecules are RNA molecules and the plurality of circular probes are composed primarily of DNA, optionally wherein the RNA molecules are mRNA molecules.

In any of the embodiments herein, the nucleic acid molecule or the plurality of nucleic acid molecules may be RNA. In any of the embodiments herein, the nucleic acid molecule or the plurality of nucleic acid molecules may be mRNA or non-coding RNA (ncRNA). In some embodiments the mRNA may be a nascent RNA, a pre-mRNA, a primary-transcript RNA, a processed RNA, a capped mRNA, a non-capped mRNA, a polyadenylated mRNA, a non-polyadenylated mRNA, a spliced mRNA, or a non-spliced mRNA. In some embodiments the ncRNA may be a tRNA, tsRNA, IRNA, srRNA, miRNA, siRNA, piRNA, snoRNA, snRNA, exRNA, scaRNA, gRNA, or long ncRNA (lncRNA). In some embodiments the lncRNA may be Xist or HOTAIR. In any of the embodiments herein, the nucleic acid molecule may be linear or circular. In some embodiments the nucleic acid molecule may be a circular RNA.

In any of the embodiments herein, the nucleic acid molecule may be a viral, bacterial, fungal, plant, mammalian, or synthetic nucleic acid. In any of the embodiments herein, the circular probe may be primarily composed of DNA. In any of the embodiments herein, the loop region may be a first loop region and the circular probe may further comprise a second loop region. In any of the embodiments herein the circular probe may be a dumbbell probe. In any of the embodiments herein, the sequence in the loop region may comprise or may be a toehold region, and upon hybridization of the first sequence in the nucleic acid molecule to the toehold region, the second sequence in the nucleic acid molecule invades into the stem region, wherein sequence complementarity between the second sequence and the first strand drives branch migration to displace the second strand from the first strand.

In any of the embodiments herein, the second sequence in the nucleic acid molecule may comprise the ribonucleotide(s) complementary to the one or more ribonucleotides in the circular probe. In any of the embodiments herein, the ribonucleotide(s) complementary to the one or more ribonucleotides may be internal in the second sequence. In some embodiments, the ribonucleotide(s) complementary to the one or more ribonucleotides may be of substantially equal distance to the 5' and 3' nucleotides of the second sequence, or wherein the one or more ribonucleotides may be of substantially equal distance to the 5' and 3' nucleotides of the first strand of the stem region.

In any of the embodiments herein, the second strand of the stem region may comprise one or more ribonucleotides. In some embodiments the one or more ribonucleotides in the second strand base pair with the one or more ribonucleotides in the first strand. In some embodiments the one or more ribonucleotides in the second strand do not base pair with the one or more ribonucleotides in the first strand.

In any of the embodiments herein, the method may further comprise, prior to the detecting step, a step of removing unbound and/or non-specifically bound molecules of the circular probe from the biological sample. In some embodiments the removing step may comprise one or more stringent washes. In any of the embodiments herein, step (c) may further comprise cleaving the one or more ribonucleotides that remain hybridized to the second strand of the stem region, wherein the one or more ribonucleotides not hybridized to the second strand of the stem region may not be cleaved. In some embodiments the cleaving step may be after the removing step. In some embodiments, the cleaving step may comprise treating the biological sample with an RNAse H.

In some embodiments, the biological sample may be treated with the RNAse H in the presence of one or more RNAse inhibitors that do not inhibit the RNAse H. In some embodiments the one or more RNAse inhibitors may comprise a ribonuclease inhibitor (RI) protein.

In any of the embodiments herein, the RNAse may comprise an RNAse H1 and/or an RNAse H2. In any of the embodiments herein, the first strand of the stem region may comprise no more than one ribonucleotide, no more than two contiguous ribonucleotides, or no more than three contiguous ribonucleotides, and the one or more ribonucleotides that remain hybridized to the second strand of the stem region may be cleaved by an RNAse H2.

In any of the embodiments herein, the first strand of the stem region may comprise four or more contiguous ribonucleotides, and the four or more contiguous ribonucleotides that remain hybridized to the second strand of the stem region may be cleaved by an RNAse H1 and/or an RNAse H2. In any of the embodiments herein, the RNAse may not cleave the nucleic acid molecule or a portion thereof hybridized to the circular probe. In any of the embodiments herein, the RNAse may cleave the nucleic acid molecule or a portion thereof hybridized to the circular probe.

In any of the embodiments herein, the method may further comprise, prior to the detecting step, a step of anchoring the circular probe directly or indirectly to a molecule in the biological sample or a matrix embedding the biological sample. In any of the embodiments herein, the loop region of the circular probe may comprise a barcode sequence corresponding to a sequence in the nucleic acid molecule. In any of the embodiments herein, the barcode sequence can comprise a nucleic acid sequence. In any of the embodiments herein, the product may be a rolling circle amplification (RCA) product of the circular probe. In some embodiments, the method may further comprise, prior to the detecting step, a step of generating the RCA product in the biological sample.

In any of the embodiments herein, the method may further comprise a step of inactivating the RNAse. Alternatively, in any of the embodiments herein, the method may not require a step of inactivating the RNAse. In any of the embodiments herein, the RNAse and/or one or more other enzymes such as other RNAse(s) can be used to process RNA hybridized to the circular probe. In some embodiments the processed RNA can be used as a primer for RCA of the circular probe.

In any of the embodiments herein, the method may further comprise: using the nucleic acid molecule hybridized to the circular probe as a primer for RCA of the circular probe. In some embodiments the nucleic acid molecule may be RNA and the RCA may be RNA-primed RCA; and/or providing a separate primer for RCA of the circular probe, wherein the separate primer may comprise DNA and/or RNA. In some embodiments, the separate primer may hybridize to a sequence in the loop region, or wherein the loop region may be a first loop region and the separate primer hybridizes to a sequence in a second loop region in the circular probe. In any of the embodiments herein, the separate primer may be DNA and may be optionally directly or indirectly anchored to a molecule in the biological sample or a matrix embedding the biological sample.

In any of the embodiments herein, the method may further comprise, prior to the detecting step, a step of anchoring the RCA product directly or indirectly to a molecule in the biological sample or a matrix embedding the biological sample. In any of the embodiments herein, the detecting step may comprise: contacting the RCA product with one or more detectable probes that hybridize to the RCA product; and/or contacting the RCA product with one or more intermediate probes that hybridize to the RCA product, wherein each intermediate probe may comprise a sequence that hybridizes to the RCA product and a sequence that hybridizes to one or more detectable probes. In some embodiments, the detecting step may comprise contacting the RCA product with detectable probes and/or intermediate probes in sequential cycles.

In any of the embodiments herein, the method may further comprise providing the circular probe prior to contacting it with the biological sample. In some embodiments the circular probe may be provided by connecting two or more probes. In some embodiments, the circular probe may be provided by ligating a first hairpin probe to a second hairpin probe, any one or both of which may comprise one or more ribonucleotides at the 5' and/or the 3' end. In some embodiments the ligation may be preceded by gap filling, thereby circularizing the first and second hairpin probes to provide the circular probe. In some embodiments, the first hairpin probe may comprise a first loop region, a first stem region, and a first 3' single-stranded region comprising one or more ribonucleotides. In some embodiments the 3' terminal nucleotide of the first hairpin may be a ribonucleotide; the second hairpin probe may comprise a second loop region, a second stem region, and a second 3' single-stranded region that may be DNA. In some embodiments the 5' end of the second hairpin may comprise one or more ribonucleotides; and the first 3' single-stranded region or a portion thereof may be complementary to the second 3' single-stranded region or a portion thereof.

In any of the embodiments herein, the providing step may comprise using a ligase having DNA-templated DNA ligase activity and/or an DNA-templated RNA ligase activity. In some embodiments the ligase may be a *Chlorella* virus DNA ligase (PBCV DNA ligase), a T4 RNA ligase, a T4 DNA ligase, or a single-stranded DNA (ssDNA) ligase. In some embodiments the T4 RNA ligase may be a T4 RNA ligase 2 (T4 Rnl2). In any of the embodiments herein, the providing step may comprise using an exonuclease to digest probe molecules that may not be circularized. In some embodiments the exonuclease may comprise Exonuclease I and/or Exonuclease I. In any of the embodiments herein, the providing step may comprise using an RNAse to digest probe molecules that may not be circularized. In some embodiments the RNAse may be RNAse R.

In some aspects, provided herein is a method for analyzing a biological sample, comprising: (a) contacting the biological sample comprising an RNA molecule with a circular probe, wherein: the circular probe comprises a first loop region, a stem region, and a second loop region, the stem region comprises (i) a first strand which is primarily composed of DNA and comprises no more than four consecutive ribonucleotides and (ii) a second strand which is DNA that is complementary to the first strand, and a sequence in the first loop region hybridizes to a first sequence in the RNA molecule; (b) hybridizing the RNA molecule to the first strand of the stem region, wherein: if a second sequence in the nucleic acid molecule is complementary to the first strand, the second strand is displaced from the first strand, the circular probe hybridizes to at least the first and second sequences in the RNA molecule, and the no more than four consecutive ribonucleotides in the circular probe hybridize to complementary ribonucleotides in the RNA molecule; (c) contacting the biological sample with an RNAse H2, wherein: if the first strand remains hybridized to the second strand, the RNAse H2 cleaves the no more than four consecutive ribonucleotides in the first strand, thereby de-circularizing the circular probe, and if the first strand is hybridized to the RNA molecule, the RNAse H2 does not cleave the no more than four consecutive ribonucleotides in the first strand, whereby the circular probe remains circular; (d) generating a rolling circle amplification (RCA) product of the circular probe, whereas no RCA product of a de-circularized probe is generated; and (e) detecting a signal or absence thereof, wherein the signal is associated with the RCA product.

In any of the embodiments herein, the nucleic acid molecule or the RNA molecule may be endogenous or generated in situ in the biological sample. In some embodiments, the nucleic acid molecule or the RNA molecule may be a product or derivative of an endogenous molecule in the biological sample. In any of the embodiments herein, the nucleic acid molecule or the RNA molecule may be immobilized in the biological sample. In some embodiments, the nucleic acid molecule or the RNA molecule may be cross-linked to one or more molecules in the biological sample, a matrix such as a hydrogel, and/or one or more functional groups on a substrate.

In any of the embodiments herein, the circular probe and/or the product thereof may be immobilized in the biological sample. In any of the embodiments herein, the circular probe and/or the product thereof may be cross-linked to one or more other molecules in the biological sample. In any of the embodiments herein, the method may comprise imaging the biological sample to detect the circular probe and/or the product thereof. In some embodiments, the imaging may comprise detecting a signal associated with a fluorescently labeled probe that directly or indirectly binds to the circular probe and/or the product thereof, or detecting a signal associated with a fluorescently labeled probe that directly or indirectly binds to a probe that hybridizes to the circular probe and/or the product thereof.

In any of the embodiments herein, a sequence of the circular probe and/or the product thereof may be analyzed in situ in the biological sample. In some embodiments, the sequence of the circular probe and/or the product thereof may be analyzed by sequential hybridization, sequencing by hybridization, sequencing by ligation, sequencing by synthesis, sequencing by binding, or a combination thereof. In any of the embodiments herein, the sequence of the circular probe and/or the product thereof may comprise a barcode sequence or complement thereof.

In any of the embodiments herein, the biological sample may comprise cells or cellular components. In any of the embodiments herein, the biological sample may be a tissue sample. In any of the embodiments herein, the biological sample may be fixed. In any of the embodiments herein, the biological sample may not be fixed. In any of the embodiments herein, the biological sample may be a formalin-fixed, paraffin-embedded (FFPE) sample, a frozen tissue sample, or a fresh tissue sample.

In any of the embodiments herein, the biological sample may be permeabilized. In any of the embodiments herein, the biological sample may be processed or cleared. In any of the embodiments herein, the biological sample may be embedded in a matrix. In some embodiments, the matrix may be a hydrogel. In any of the embodiments herein, the biological sample and/or the matrix may be cross-linked. In any of the embodiments herein, a signal associated with the circular probe and/or the product thereof may be amplified in situ in the biological sample.

In some embodiments, the signal amplification in situ may comprise rolling circle amplification (RCA) of the circular probe or a probe that directly or indirectly binds to the circular probe and/or the product thereof, hybridization chain reaction (HCR) directly or indirectly on the circular probe and/or the product thereof, linear oligonucleotide hybridization chain reaction (LO-HCR) directly or indirectly on the circular probe and/or the product thereof, primer exchange reaction (PER) directly or indirectly on the circular probe and/or the product thereof, assembly of branched structures directly or indirectly on the circular probe and/or the product thereof, hybridization of a plurality of detectable probes directly or indirectly on the circular probe and/or the product thereof, or any combination thereof.

In some aspects provided herein, is a kit for analyzing a biological sample, comprising a circular probe comprising a stem region and a loop region, wherein the stem region comprises (a) a first strand comprising one or more ribonucleotides, and (b) a second strand complementary to the first strand, wherein a sequence in the loop region is capable of hybridizing to a first sequence in a nucleic acid molecule in the biological sample. In some embodiments, a sequence in the first strand may be complementary to a second sequence in the nucleic acid molecule such that the second strand may be capable of being displaced from the first strand by the second sequence in the nucleic acid molecule.

In some embodiments, the circular probe may be capable of hybridizing to at least the first and second sequences in the nucleic acid molecule, and the one or more ribonucleotides in the circular probe may be capable of hybridizing to complementary ribonucleotide(s) in the nucleic acid molecule. In some embodiments, the kit may further comprise an RNAse H capable of cleaving the one or more ribonucleotides hybridized to the second strand of the stem region, but not capable of cleaving the one or more ribonucleotides when they may not be hybridized to the second strand of the stem region. In some embodiments, the kit may further comprise one or more RNAse inhibitors that do not inhibit the RNAse H.

In any of the embodiments herein, the RNAse H may comprise an RNAse H1 and/or an RNAse H2. In any of the embodiments herein, the RNAse H may be RNAse H2 and the first strand may comprise no more than three contiguous ribonucleotides. In any of the embodiments herein, the RNAse H may be RNAse H1 and the first strand may comprise four or more contiguous ribonucleotides. In any of the embodiments herein, the kit may further comprise instructions for performing the method any of the embodiments herein.

BRIEF DESCRIPTION OF THE DRAWINGS

The drawings illustrate certain embodiments of the features and advantages of this disclosure. These embodiments are not intended to limit the scope of the appended claims in any manner.

FIG. 1A shows a first sequence of an RNA molecule binding to a toehold region which is comprised in a sequence in the loop region of the circular probe. As shown in FIG. 1B, if the second sequence in the nucleic acid molecule is complementary to a sequence in the stem region of the circular probe, the second nucleic acid sequence can invade into the stem region, hybridizing to the first strand and displacing the second strand from the first strand. A rolling circle amplification (RCA) product of the circular probe can then be generated.

DETAILED DESCRIPTION

Figure 1A:
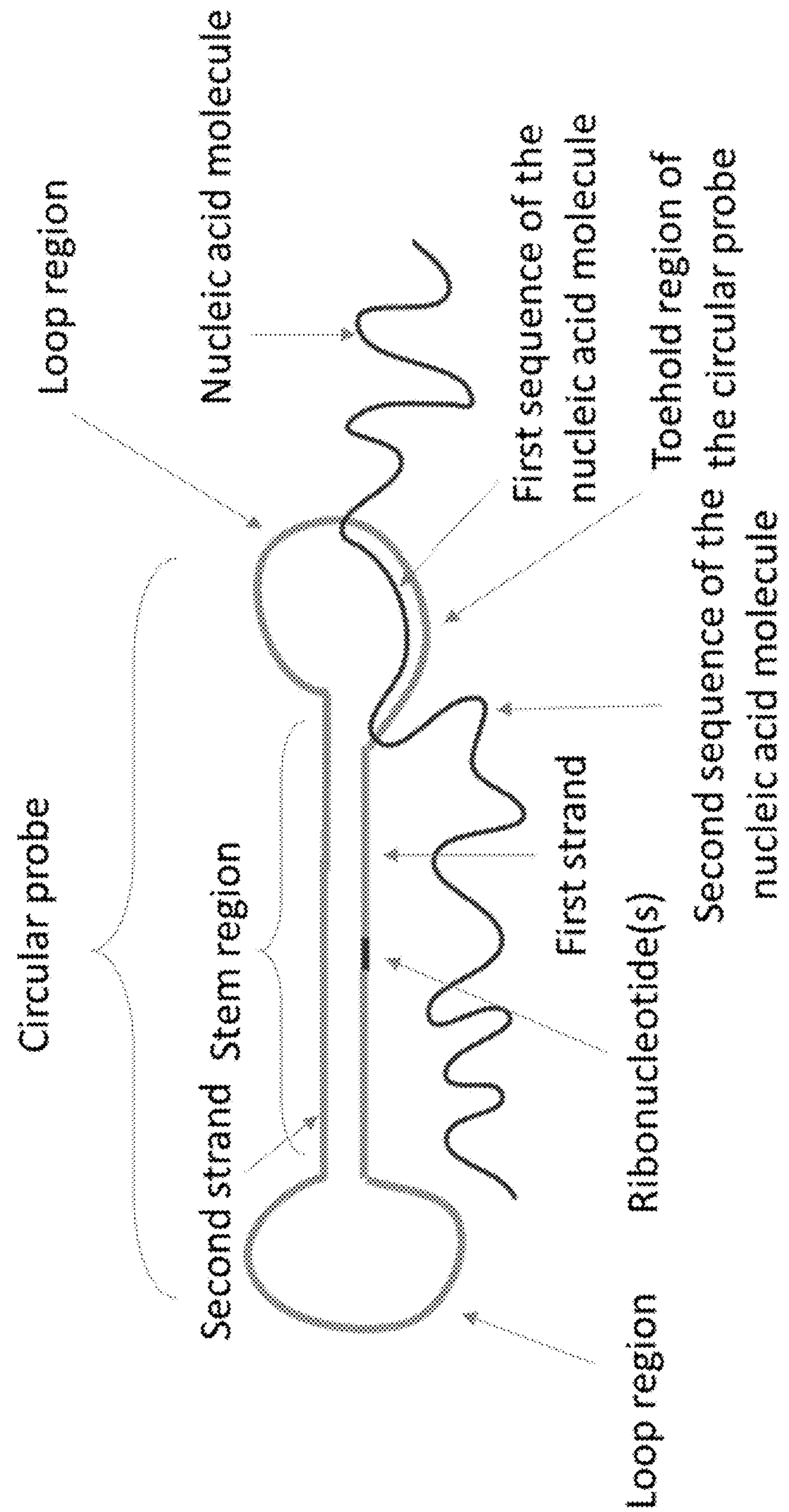
FIG. 1A and FIG. 1B depict an exemplary circular probe comprising two loop regions and a central stem region comprising a first strand and a second strand. The first strand may comprise one or more ribonucleotides while the second strand comprises deoxyribonucleotides.

All publications, comprising patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The section headings used herein are for organizational purposes only and are not to be construed as limiting the subject matter described.

I. Overview

Provided herein in some aspects are probes and methods of using the probes for analyzing molecules including nucleic acids present/generated in, introduced into, and/or from a biological sample, such as a cell or a tissue. Also provided are compositions, kits, systems, and devices for use in accordance with the provided methods. In some embodiments, provided herein are methods, kits, and compositions for analyzing a biological sample, such as for in situ analysis of one or more target nucleic acid(s) and/or one or more analyte(s), e.g., one or more target nucleic acids such as DNA molecules or RNA molecules, in a cell in an intact tissue sample.

Certain methods for in situ analysis based on rolling circle amplification (RCA) can have limited detection efficiency, sensitivity, and/or specificity, particularly those that require multiple steps to be performed in situ. For instance, a sample can be fixed, permeabilized, and contacted with probes for hybridization, followed by in situ probe ligation and in situ RCA of the ligated probe. Detection efficiency and sensitivity of these assays, especially workflow that depends on RNA-dependent in situ ligation of circularizable probes (e.g., padlock probes), can be compromised by oligonucleotide synthesis errors. For example, when a 100-nt padlock probe is synthesized using base-by-base synthesis, only ~60% of the synthesized probe oligonucleotides may be functionally ligatable, while the remaining 40% of in-correctly synthesized probes are available to competitively inhibit hybridization of full-length probes. In addition, only a fraction of the properly hybridized full-length probes will be correctly ligated in situ to generate a circular probe for subsequent in situ RCA. Assuming a base-by-base oligonucleotide synthesis efficiency of 99.5% per cycle, a ligation efficiency of 70%, and an RCA amplification efficiency of 90%, the probability that a given 100-nt padlock probe will successfully detect the transcript of interest would be (0.995^99)*(0.70)*(0.90)=38%, which is close to reported detection levels of direct RNA mediated probe ligation and RCA based methods. As such, there is a need to improve detection efficiency and sensitivity of existing methods. In some embodiments, provided herein are probes and methods that address one or more issues associated with existing methods.

In some embodiments, provided herein are probes that directly bind to RNA molecules. In some embodiments, the probe/RNA binding complex can be processed, e.g., by contacting the complex with an enzyme such as a ribonuclease, to de-circularize non-specific or unbound probes, thereby achieving high sensitivity and/or specificity for detecting the RNA molecules. In some embodiments, the probes and methods disclosed herein are particularly useful for direct-RNA detection (e.g., probes directly hybridize to RNA and not cDNA that is reversed transcribed from the RNA) in situ in a sample, such as a tissue sample or a substrate comprising RNA molecules deposited thereon. The RNA molecules can be endogenous in a biological sample, or can be generated in situ from a molecule that is endogenous or exogenously introduced in the biological sample.

In some embodiments, disclosed herein is a method for analyzing a biological sample, comprising: (a) contacting the biological sample comprising a nucleic acid molecule with a circular probe, wherein: the circular probe comprises one or more stem regions and one or more loop regions, wherein one of the stem regions comprises (i) a first strand comprising one or more ribonucleotides and (ii) a second strand complementary to the first strand, and wherein a sequence in one of the loop regions hybridizes to a first sequence in the nucleic acid molecule (e.g., the sequence in the loop region can be complementary to the first sequence in the nucleic acid molecule); (b) allowing the nucleic acid molecule to hybridize to the first strand of the stem region, wherein: if a second sequence in the nucleic acid molecule is complementary to the first strand, the second strand is displaced from the first strand (e.g., by the second sequence in the nucleic acid molecule), the circular probe hybridizes to at least the first and second sequences in the nucleic acid molecule, and the one or more ribonucleotides in the circular probe hybridize to complementary ribonucleotide(s) in the nucleic acid molecule; and (c) detecting a signal or absence thereof, wherein the signal is associated with the circular probe or a product thereof. In particular embodiments, the method further comprises providing conditions for de-circularizing circular probes that are unbound or non-specifically bound to the nucleic acid molecule. In some embodiments, the conditions comprise contacting the biological sample with an agent, such as an enzyme or a chemical, e.g., a ribonuclease such as an RNAse H. In particular embodiments, the product of the circular probe is generated without de-circularizing the circular probe. In particular embodiments, the product of the circular probe is generated while the circular probe remains circular. In particular embodiments, the circular probe is not cleaved or degraded (e.g., by an enzyme such as a ribonuclease) prior to and/or while the probe is being generated. In particular embodiments, the circular probe is not cleaved and subsequently re-circularized in order for the product to be generated; rather, the circular probe remains circular during the contacting step, during the allowing/hybridizing step, during the contact with a ribonuclease such as an RNAse, and during the generation of the product of the circular probe.

In some aspects, the provided methods involve the use of a circular probe molecule (e.g. a dumbbell probe) to hybridize to a target nucleic acid. In certain embodiments, the provided methods use rolling circle amplification (RCA) to detect target nucleic acids in situ. In some aspects, the circular probe comprises one or more stem regions and two or more loop regions. In some aspects, the stem region of the probe comprises a first strand and a second strand. In some aspects, the first strand of the stem region is complementary to the second strand of the stem region. In some aspects, RCA will only occur if the first strand is displaced from the second strand. In some aspects, the present disclosure provides methods and compositions that allow for increased specificity and/or sensitivity of a probe-based assay involving using a circular probe (e.g. a dumbbell probe) and RNAse treatment to prevent amplification of probes unbound or non-specifically hybridized to analytes in the sample.

In some aspects, the present disclosure provides methods for detecting a target nucleic acid using a circular probe, wherein a first sequence of a target nucleic acid (e.g., RNA) is capable of hybridizing to a toehold region in the loop region of the circular probe. In some embodiments, a second sequence of the target nucleic acid (e.g., adjacent to the first sequence of the target nucleic acid) is complementary to the first strand of the stem region of the circular probe and is capable of invading into the stem region. In certain embodiments, the second sequence can hybridize to the first strand of the stem region, e.g., via complementary hybridization regions, thereby displacing the second strand of the stem region from the first strand. In some aspects, if the second sequence in the target nucleic acid molecule is not complementary to the first strand of the stem region, the second strand of the stem region will not be displaced from the first strand. In some embodiments, the binding of the first sequence of the target nucleic acid to the toehold region (e.g., in the single-stranded "open" loop region) initiates further targeted hybridization of the first strand in the double-stranded stem region to the second sequence of the target nucleic acid. The targeted hybridization thus at least partially unzips the stem region of the circular probe (e.g., a dumbbell probe). In cases where the target nucleic acid is RNA and the circular probe is primarily composed of DNA, the predominantly DNA:RNA hybridization between the probe and the target nucleic acid is favored over the predominantly DNA:DNA hybridization in the stem region of the probe, since DNA:RNA hybrids are thermodynamically more stable than corresponding DNA:DNA duplexes.

In some aspects, the present disclosure provides methods for detecting a target nucleic acid using a circular probe, wherein the target nucleic acid molecule is an RNA molecule and wherein the circular probe is primarily composed of DNA. In some embodiments, the first strand of the stem region of the circular probe comprises one or more ribonucleotides. For instance, the first strand can comprise 4, 3, 2, or 1 ribonucleotide in a DNA backbone, where each ribonucleotide base pairs with the corresponding deoxyribonucleotide in the second strand of the stem region. In some embodiments, the second strand of the stem region does not contain any ribonucleotide and may contain only deoxyribonucleotides. In some embodiments, the ribonucleotide(s) of the second sequence in the nucleic acid molecule are complementary to the one or more ribonucleotides of the first strand of the stem region of the circular probe. In some aspects, once the second sequence of the target RNA invades into the stem region (e.g., via branch migration initiated by binding of the first sequence of the target RNA to the toehold region in the loop region) and displaces the second strand, each of the one or more ribonucleotides of the first strand base pairs with the corresponding ribonucleotide in the second sequence of the target RNA. In some embodiments, the sample can be contacted with a ribonuclease that cleaves the one or more ribonucleotides hybridized to DNA but not those hybridized to RNA. In some embodiments, if the second strand of the stem region is not displaced from the first strand, the one or more ribonucleotides in the first strand remain hybridized to the second strand which is DNA and are cleaved by the ribonuclease (e.g., an RNAse), thereby de-circularizing the circular probe. In some embodiments, if the second strand of the stem region is displaced such that the first strand hybridizes to the target RNA, the one or more ribonucleotides are hybridized to RNA and are not cleaved by the ribonuclease (e.g., an RNAse). As such, the circular probe is not cleaved and remains circular for subsequent RCA and detection. In some embodiments, the target RNA (or a portion thereof) hybridized to the circular probe can be used to prime RCA of the circular probe.

In some aspects, the biological sample is treated with an RNAse after the addition of the circular probe. In certain embodiments, the biological sample is treated with RNAse H (e.g. RNAse H1 or RNAse H2). In certain embodiments, the RNAse cleaves the one or more ribonucleotides which are hybridized to the second strand of the stem region of the circular probe. In embodiments where the circular probe comprises more than one ribonucleotide, the ribonucleotides can be contiguous in the circular probe. In one embodiment, the one or more ribonucleotides of the circular probe that are not bound to a target RNA are digested by the RNAse and the probe becomes de-circularized. In another embodiment, the circular probe has non-specifically hybridized to an RNA, wherein a first sequence of the RNA molecule has hybridized to the circular probe (e.g., in the loop region) but a second sequence of the RNA molecule is not complementary to the first strand of the stem region and thus does not hybridize and does not displace the second strand. In this example, the one or more ribonucleotides remain hybridized to the second strand which is DNA, and are digested by the RNAse to de-circularize the probe. In both embodiments, the circular probe is cleaved and therefore no RCA will take place. In contrast, specifically hybridized circular probes remain circular during and after RNAse treatment, since the one or more ribonucleotides in the probe are hybridized to the target RNA molecule. In some aspects, the removal of the unbound and/or nonspecifically bound probes by way of RNAse digestion may serve to increase the sensitivity and/or specificity of signal detection.

Provided herein are methods involving the use of a circularized probe (e.g. a dumbbell probe) wherein the probe comprises a stem region and a loop region wherein the stem region comprises a first strand comprising one or more ribonucleotides for analyzing one or more target nucleic acid(s), such as a target nucleic acid (e.g. a messenger RNA) present in a cell or a biological sample, such as a tissue sample. Also provided are probes, sets of probes, compositions, kits, systems and devices for use in accordance with the provided methods. In some aspects, the provided methods and systems can be applied to detect, image, quantitate, or determine the presence or absence of one or more target nucleic acid(s). In some aspects, the provided embodiments can be employed for in situ detection and/or sequencing of a target nucleic acid in a cell, e.g., in cells of a biological sample or a sample derived from a biological sample.

In some aspects, provided herein are in situ assays using microscopy as a readout, e.g., nucleic acid sequencing, hybridization, or other detection or determination methods involving an optical readout. In some aspects, detection or determination of a sequence of one, two, three, four, five, or more nucleotides of a target nucleic acid in a cell in an intact tissue is performed in situ. In some embodiments, a provided method is quantitative and preserves the spatial information within a tissue sample without physically isolating cells or using homogenates. In some aspects, detection or determination of a sequence is performed such that the localization of the target nucleic acid (or product or a derivative thereof associated with the target nucleic acid) in the originating sample is detected. In some embodiments, the assay comprises detecting the presence or absence of an amplification product or a portion thereof (e.g., RCA product). In some aspects, exemplary detection includes in situ sequencing and/or in situ sequential hybridization, including sequencing by hybridization, sequencing by ligation, sequencing by synthesis, sequencing by binding, and/or a method based on single molecule fluorescent in situ hybridization (smFISH). In some embodiments, a method for spatially profiling analytes such as the transcriptome or a subset thereof in a biological sample is provided. Methods, compositions, kits, devices, and systems for these in situ assays, comprising spatial genomics and transcriptomics assays, are provided.

II. Samples, Analytes, and Target Sequences

A. Samples

A sample disclosed herein can be obtained or derived from any biological sample. Methods and compositions disclosed herein may be used for analyzing a biological sample, which may be obtained from a subject using any of a variety of techniques including, but not limited to, biopsy, surgery, and laser capture microscopy (LCM), and generally includes cells and/or other biological material from the subject. In addition to the subjects described above, a biological sample can be obtained from a prokaryote such as a bacterium, an archaea, a virus, or a viroid. A biological sample can also be obtained from non-mammalian organisms (e.g., a plant, an insect, an arachnid, a nematode, a fungus, or an amphibian). A biological sample can also be obtained from a eukaryote, such as a tissue sample, a patient derived organoid (PDO) or patient derived xenograft (PDX). A biological sample from an organism may comprise one or more other organisms or components therefrom. For example, a mammalian tissue section may comprise a prion, a viroid, a virus, a bacterium, a fungus, or components from other organisms, in addition to mammalian cells and non-cellular tissue components. Subjects from which biological samples can be obtained can be healthy or asymptomatic individuals, individuals that have or are suspected of having a disease (e.g., a patient with a disease such as cancer) or a pre-disposition to a disease, and/or individuals in need of therapy or suspected of needing therapy.

The biological sample can include any number of macromolecules, for example, cellular macromolecules and organelles (e.g., mitochondria and nuclei). The biological sample can be a nucleic acid sample and/or protein sample. The biological sample can be a carbohydrate sample or a lipid sample. The biological sample can be obtained as a tissue sample, such as a tissue section, biopsy, a core biopsy, needle aspirate, or fine needle aspirate. The sample can be a fluid sample, such as a blood sample, urine sample, or saliva sample. The sample can be a skin sample, a colon sample, a cheek swab, a histology sample, a histopathology sample, a plasma or serum sample, a tumor sample, living cells, cultured cells, a clinical sample such as, for example, whole blood or blood-derived products, blood cells, or cultured tissues or cells, including cell suspensions. In some embodiments, the biological sample may comprise cells which are deposited on a surface.

Cell-free biological samples can include extracellular polynucleotides. Extracellular polynucleotides can be isolated from a bodily sample, e.g., blood, plasma, serum, urine, saliva, mucosal excretions, sputum, stool, and tears.

Biological samples can be derived from a homogeneous culture or population of the subjects or organisms mentioned herein or alternatively from a collection of several different organisms, for example, in a community or ecosystem.

Biological samples can include one or more diseased cells. A diseased cell can have altered metabolic properties, gene expression, protein expression, and/or morphologic features. Examples of diseases include inflammatory disorders, metabolic disorders, nervous system disorders, and cancer. Cancer cells can be derived from solid tumors, hematological malignancies, cell lines, or obtained as circulating tumor cells. Biological samples can also include fetal cells and immune cells.

Biological samples can include analytes (e.g., protein, RNA, and/or DNA) embedded in a 3D matrix. In some embodiments, amplicons (e.g., rolling circle amplification products) derived from or associated with analytes (e.g., protein, RNA, and/or DNA) can be embedded in a 3D matrix. In some embodiments, a 3D matrix may comprise a network of natural molecules and/or synthetic molecules that are chemically and/or enzymatically linked, e.g., by crosslinking. In some embodiments, a 3D matrix may comprise a synthetic polymer. In some embodiments, a 3D matrix comprises a hydrogel.

In some embodiments, a substrate herein can be any support that is insoluble in aqueous liquid and which allows for positioning of biological samples, analytes, features, and/or reagents (e.g., probes) on the support. In some embodiments, a biological sample can be attached to a substrate. Attachment of the biological sample can be irreversible or reversible, depending upon the nature of the sample and subsequent steps in the analytical method. In certain embodiments, the sample can be attached to the substrate reversibly by applying a suitable polymer coating to the substrate, and contacting the sample to the polymer coating. The sample can then be detached from the substrate, e.g., using an organic solvent that at least partially dissolves the polymer coating. Hydrogels are examples of polymers that are suitable for this purpose.

In some embodiments, the substrate can be coated or functionalized with one or more substances to facilitate attachment of the sample to the substrate. Suitable substances that can be used to coat or functionalize the substrate include, but are not limited to, lectins, poly-lysine, antibodies, and polysaccharides.

A variety of steps can be performed to prepare or process a biological sample for and/or during an assay. Except where indicated otherwise, the preparative or processing steps described below can generally be combined in any manner and in any order to appropriately prepare or process a particular sample for and/or analysis.

(i) Tissue Sectioning

A biological sample can be harvested from a subject (e.g., via surgical biopsy, whole subject sectioning) or grown in vitro on a growth substrate or culture dish as a population of cells, and prepared for analysis as a tissue slice or tissue section. Grown samples may be sufficiently thin for analysis without further processing steps. Alternatively, grown samples, and samples obtained via biopsy or sectioning, can be prepared as thin tissue sections using a mechanical cutting apparatus such as a vibrating blade microtome. As another alternative, in some embodiments, a thin tissue section can be prepared by applying a touch imprint of a biological sample to a suitable substrate material.

The thickness of the tissue section can be a fraction of (e.g., less than 0.9, 0.8, 0.7, 0.6, 0.5, 0.4, 0.3, 0.2, or 0.1) the maximum cross-sectional dimension of a cell. However, tissue sections having a thickness that is larger than the maximum cross-section cell dimension can also be used. For example, cryostat sections can be used, which can be, e.g., 10-20 μm thick.

More generally, the thickness of a tissue section typically depends on the method used to prepare the section and the physical characteristics of the tissue, and therefore sections having a wide variety of different thicknesses can be prepared and used. For example, the thickness of the tissue section can be at least 0.1, 0.2, 0.3, 0.4, 0.5, 0.7, 1.0, 1.5, 2, 3, 4, 5, 6, 7, 8, 9, 10, 12, 13, 14, 15, 20, 30, 40, or 50 μm. Thicker sections can also be used if desired or convenient, e.g., at least 70, 80, 90, or 100 μm or more. Typically, the thickness of a tissue section is between 1-100 μm, 1-50 μm, 1-30 μm, 1-25 μm, 1-20 μm, 1-15 μm, 1-10 μm, 2-8 μm, 3-7 μm, or 4-6 μm, but as mentioned above, sections with thicknesses larger or smaller than these ranges can also be analyzed.

Multiple sections can also be obtained from a single biological sample. For example, multiple tissue sections can be obtained from a surgical biopsy sample by performing serial sectioning of the biopsy sample using a sectioning blade. Spatial information among the serial sections can be preserved in this manner, and the sections can be analyzed successively to obtain three-dimensional information about the biological sample.

(ii) Freezing

In some embodiments, the biological sample (e.g., a tissue section as described above) can be prepared by deep freezing at a temperature suitable to maintain or preserve the integrity (e.g., the physical characteristics) of the tissue structure. The frozen tissue sample can be sectioned, e.g., thinly sliced, onto a substrate surface using any number of suitable methods. For example, a tissue sample can be prepared using a chilled microtome (e.g., a cryostat) set at a temperature suitable to maintain both the structural integrity of the tissue sample and the chemical properties of the nucleic acids in the sample. Such a temperature can be, e.g., less than −15° C., less than −20° C., or less than −25° C.

(iii) Fixation and Post Fixation

In some embodiments, the biological sample can be prepared using formalin-fixation and paraffin-embedding (FFPE), which are established methods. In some embodiments, cell suspensions and other non-tissue samples can be prepared using formalin-fixation and paraffin-embedding. Following fixation of the sample and embedding in a paraffin or resin block, the sample can be sectioned as described above. Prior to analysis, the paraffin-embedding material can be removed from the tissue section (e.g., deparaffinization) by incubating the tissue section in an appropriate solvent (e.g., xylene) followed by a rinse (e.g., 99.5% ethanol for 2 minutes, 96% ethanol for 2 minutes, and 70% ethanol for 2 minutes).

As an alternative to formalin fixation described above, a biological sample can be fixed in any of a variety of other fixatives to preserve the biological structure of the sample prior to analysis. For example, a sample can be fixed via immersion in ethanol, methanol, acetone, paraformaldehyde (PFA)-Triton, and combinations thereof.

In some embodiments, acetone fixation is used with fresh frozen samples, which can include, but are not limited to, cortex tissue, mouse olfactory bulb, human brain tumor, human post-mortem brain, and breast cancer samples. When acetone fixation is performed, pre-permeabilization steps (described below) may not be performed. Alternatively, acetone fixation can be performed in conjunction with permeabilization steps.

In some embodiments, the methods provided herein comprise one or more post-fixing (also referred to as post fixation) steps. In some embodiments, one or more post-fixing steps are performed after contacting a sample with a polynucleotide disclosed herein, e.g., one or more probes such as a circular probe disclosed herein. In some embodiments, one or more post-fixing steps are performed after a hybridization complex comprising a probe (e.g., a circular probe) and a target is formed in a sample.

In some embodiments, one or more post-fixing steps are performed after contacting a sample with a binding or labelling agent (e.g., an antibody or antigen binding fragment thereof) for a non-nucleic acid analyte such as a protein analyte. The labelling agent can comprise a nucleic acid molecule (e.g., reporter oligonucleotide) comprising a sequence corresponding to the labelling agent and therefore corresponds to (e.g., uniquely identifies) the analyte. In some embodiments, the labelling agent can comprise a reporter oligonucleotide comprising one or more barcode sequences.

A post-fixing step may be performed using any suitable fixation reagent disclosed herein, for example, 3% (w/v) paraformaldehyde in DEPC-PBS.

(iv) Embedding

As an alternative to paraffin embedding described above, a biological sample can be embedded in any of a variety of other embedding materials to provide structural substrate to the sample prior to sectioning and other handling steps. In some cases, the embedding material can be removed e.g., prior to analysis of tissue sections obtained from the sample. Suitable embedding materials include, but are not limited to, waxes, resins (e.g., methacrylate resins), epoxies, and agar.

In some embodiments, the biological sample can be embedded in a matrix (e.g., a hydrogel matrix). Embedding the sample in this manner typically involves contacting the biological sample with a hydrogel such that the biological sample becomes surrounded by the hydrogel. For example, the sample can be embedded by contacting the sample with a suitable polymer material, and activating the polymer material to form a hydrogel. In some embodiments, the hydrogel is formed such that the hydrogel is internalized within the biological sample.

In some embodiments, the biological sample is immobilized in the hydrogel via cross-linking of the polymer material that forms the hydrogel. Cross-linking can be performed chemically and/or photochemically, or alternatively by any other established hydrogel-formation method.

The composition and application of the hydrogel-matrix to a biological sample typically depends on the nature and preparation of the biological sample (e.g., sectioned, non-sectioned, type of fixation). As one example, where the biological sample is a tissue section, the hydrogel-matrix can include a monomer solution and an ammonium persulfate (APS) initiator/tetramethylethylenediamine (TEMED) accelerator solution. As another example, where the biological sample consists of cells (e.g., cultured cells or cells disassociated from a tissue sample), the cells can be incubated with the monomer solution and APS/TEMED solutions. For cells, hydrogel-matrix gels are formed in compartments, including but not limited to devices used to culture, maintain, or transport the cells. For example, hydrogel-matrices can be formed with monomer solution plus APS/TEMED added to the compartment to a depth ranging from about 0.1 μm to about 2 mm.

Additional methods and aspects of hydrogel embedding of biological samples are described for example in Chen et al., Science 347 (6221): 543-548, 2015, the entire contents of which are incorporated herein by reference.

(v) Staining and Immunohistochemistry (IHC)

To facilitate visualization, biological samples can be stained using a wide variety of stains and staining techniques. In some embodiments, for example, a sample can be stained using any number of stains and/or immunohistochemical reagents. One or more staining steps may be performed to prepare or process a biological sample for an assay described herein or may be performed during and/or after an assay. In some embodiments, the sample can be contacted with one or more nucleic acid stains, membrane stains (e.g., cellular or nuclear membrane), cytological stains, or combinations thereof. In some examples, the stain may be specific to proteins, phospholipids, DNA (e.g., dsDNA, ssDNA), RNA, an organelle or compartment of the cell. The sample may be contacted with one or more labeled antibodies (e.g., a primary antibody specific for the analyte of interest and a labeled secondary antibody specific for the primary antibody). In some embodiments, cells in the sample can be segmented using one or more images taken of the stained sample.

In some embodiments, the stain is performed using a lipophilic dye. In some examples, the staining is performed with a lipophilic carbocyanine or aminostyryl dye, or analogs thereof (e.g, DiI, DiO, DIR, DiD). Other cell membrane stains may include FM and RH dyes or immunohistochemical reagents specific for cell membrane proteins. In some examples, the stain may include but is not limited to, acridine orange, acid fuchsin, Bismarck brown, carmine, coomassie blue, cresyl violet, DAPI, eosin, ethidium bromide, acid fuchsine, haematoxylin, Hoechst stains, iodine, methyl green, methylene blue, neutral red, Nile blue, Nile red, osmium tetroxide, ruthenium red, propidium iodide, rhodamine (e.g., rhodamine B), or safranine, or derivatives thereof. In some embodiments, the sample may be stained with haematoxylin and eosin (H&E).

The sample can be stained using hematoxylin and eosin (H&E) staining techniques, using Papanicolaou staining techniques, Masson's trichrome staining techniques, silver staining techniques, Sudan staining techniques, and/or using Periodic Acid Schiff (PAS) staining techniques. PAS staining is typically performed after formalin or acetone fixation. In some embodiments, the sample can be stained using Romanowsky stain, including Wright's stain, Jenner's stain, Can-Grunwald stain, Leishman stain, and Giemsa stain.

In some embodiments, biological samples can be destained. Methods of destaining or discoloring a biological sample generally depend on the nature of the stain(s) applied to the sample. For example, in some embodiments, one or more immunofluorescent stains are applied to the sample via antibody coupling. Such stains can be removed using techniques such as cleavage of disulfide linkages via treatment with a reducing agent and detergent washing, chaotropic salt treatment, treatment with antigen retrieval solution, and treatment with an acidic glycine buffer. Methods for multiplexed staining and destaining are described, for example, in Bolognesi et al., *J. Histochem. Cytochem.* 2017; 65 (8): 431-444, Lin et al., *Nat Commun.* 2015; 6:8390, Pirici et al., *J. Histochem. Cytochem.* 2009; 57:567-75, and Glass et al., *J. Histochem. Cytochem.* 2009; 57:899-905, the entire contents of each of which are incorporated herein by reference.

(vi) Isometric Expansion

In some embodiments, a biological sample embedded in a matrix (e.g., a hydrogel) can be isometrically expanded. Isometric expansion methods that can be used include hydration, a preparative step in expansion microscopy, as described in Chen et al., *Science* 347 (6221): 543-548, 2015.

Isometric expansion can be performed by anchoring one or more components of a biological sample to a gel, followed by gel formation, proteolysis, and swelling. In some embodiments, analytes in the sample, products of the analytes, and/or probes associated with analytes in the sample can be anchored to the matrix (e.g., hydrogel). Isometric expansion of the biological sample can occur prior to immobilization of the biological sample on a substrate, or after the biological sample is immobilized to a substrate. In some embodiments, the isometrically expanded biological sample can be removed from the substrate prior to contacting the substrate with probes disclosed herein.

In general, the steps used to perform isometric expansion of the biological sample can depend on the characteristics of the sample (e.g., thickness of tissue section, fixation, cross-linking), and/or the analyte of interest (e.g., different conditions to anchor RNA, DNA, and protein to a gel).

In some embodiments, proteins in the biological sample are anchored to a swellable gel such as a polyelectrolyte gel. An antibody can be directed to the protein before, after, or in conjunction with being anchored to the swellable gel. DNA and/or RNA in a biological sample can also be anchored to the swellable gel via a suitable linker. Examples of such linkers include, but are not limited to, 6-((Acryloyl) amino) hexanoic acid (Acryloyl-X SE) (available from ThermoFisher, Waltham, MA), Label-IT Amine (available from MirusBio, Madison, WI) and Label X (described for example in Chen et al., Nat. Methods 13:679-684, 2016, the entire contents of which are incorporated herein by reference).

Isometric expansion of the sample can increase the spatial resolution of the subsequent analysis of the sample. The increased resolution in spatial profiling can be determined by comparison of an isometrically expanded sample with a sample that has not been isometrically expanded.

In some embodiments, a biological sample is isometrically expanded to a size at least 2×, 2.1×, 2.2×, 2.3×, 2.4×, 2.5×, 2.6×, 2.7×, 2.8×, 2.9×, 3×, 3.1×, 3.2×, 3.3×, 3.4×, 3.5×, 3.6×, 3.7×, 3.8×, 3.9×, 4×, 4.1×, 4.2×, 4.3×, 4.4×, 4.5×, 4.6×, 4.7×, 4.8×, or 4.9× its non-expanded size. In some embodiments, the sample is isometrically expanded to at least 2× and less than 20× of its non-expanded size.

(vii) Crosslinking and De-Crosslinking

In some embodiments, the biological sample is reversibly cross-linked prior to or during an in situ assay. In some aspects, the analytes, polynucleotides and/or amplification product (e.g., amplicon) of an analyte or a probe bound thereto can be anchored to a polymer matrix. For example, the polymer matrix can be a hydrogel. In some embodiments, one or more of the polynucleotide probe(s) and/or amplification product (e.g., amplicon) thereof can be modified to contain functional groups that can be used as an anchoring site to attach the polynucleotide probes and/or amplification product to a polymer matrix. In some embodiments, a modified probe comprising oligo dT may be used to bind to mRNA molecules of interest, followed by reversible crosslinking of the mRNA molecules.

In some embodiments, the biological sample is immobilized in a hydrogel via cross-linking of the polymer material that forms the hydrogel. Cross-linking can be performed chemically and/or photochemically, or alternatively by any other established hydrogel-formation method. A hydrogel may include a macromolecular polymer gel including a network. Within the network, some polymer chains can optionally be cross-linked, although cross-linking does not always occur.

In some embodiments, a hydrogel can include hydrogel subunits, such as, but not limited to, acrylamide, bis-acrylamide, polyacrylamide and derivatives thereof, poly(ethylene glycol) and derivatives thereof (e.g. PEG-acrylate (PEG-DA), PEG-RGD), gelatin-methacryloyl (GelMA), methacrylated hyaluronic acid (MeHA), polyaliphatic polyurethanes, polyether polyurethanes, polyester polyurethanes, polyethylene copolymers, polyamides, polyvinyl alcohols, polypropylene glycol, polytetramethylene oxide, polyvinyl pyrrolidone, polyacrylamide, poly(hydroxyethyl acrylate), and poly(hydroxyethyl methacrylate), collagen, hyaluronic acid, chitosan, dextran, agarose, gelatin, alginate, protein polymers, methylcellulose, and the like, and combinations thereof.

In some embodiments, a hydrogel includes a hybrid material, e.g., the hydrogel material includes elements of both synthetic and natural polymers. Examples of suitable hydrogels are described, for example, in U.S. Pat. Nos. 6,391,937, 9,512,422, and 9,889,422, and in U.S. Patent Application Publication Nos. 2017/0253918, 2018/0052081 and 2010/0055733, the entire contents of each of which are incorporated herein by reference.

In some embodiments, the hydrogel can form the substrate. In some embodiments, the substrate includes a hydrogel and one or more second materials. In some embodiments, the hydrogel is placed on top of one or more second materials. For example, the hydrogel can be pre-formed and then placed on top of, underneath, or in any other configuration with one or more second materials. In some embodiments, hydrogel formation occurs after contacting one or more second materials during formation of the substrate. Hydrogel formation can also occur within a structure (e.g., wells, ridges, projections, and/or markings) located on a substrate.

In some embodiments, hydrogel formation on a substrate occurs before, contemporaneously with, or after probes are provided to the sample. For example, hydrogel formation can be performed on the substrate already containing the probes.

In some embodiments, hydrogel formation occurs within a biological sample. In some embodiments, a biological sample (e.g., tissue section) is embedded in a hydrogel. In some embodiments, hydrogel subunits are infused into the biological sample, and polymerization of the hydrogel is initiated by an external or internal stimulus.

In embodiments in which a hydrogel is formed within a biological sample, functionalization chemistry can be used. In some embodiments, functionalization chemistry includes hydrogel-tissue chemistry (HTC). Any hydrogel-tissue backbone (e.g., synthetic or native) suitable for HTC can be used for anchoring biological macromolecules and modulating functionalization. Non-limiting examples of methods using HTC backbone variants include CLARITY, PACT, ExM, SWITCH and ePACT. In some embodiments, hydrogel formation within a biological sample is permanent. For example, biological macromolecules can permanently adhere to the hydrogel allowing multiple rounds of interrogation. In some embodiments, hydrogel formation within a biological sample is reversible.

In some embodiments, additional reagents are added to the hydrogel subunits before, contemporaneously with, and/or after polymerization. For example, additional reagents can include but are not limited to oligonucleotides (e.g., probes), endonucleases to fragment DNA, fragmentation buffer for DNA, DNA polymerase enzymes, dNTPs used to amplify the nucleic acid and to attach the barcode to the amplified fragments. Other enzymes can be used, including without limitation, RNA polymerase, ligase, proteinase K, and DNAse. Additional reagents can also include reverse transcriptase enzymes, including enzymes with terminal transferase activity, primers, and switch oligonucleotides. In some embodiments, optical labels are added to the hydrogel subunits before, contemporaneously with, and/or after polymerization.

In some embodiments, HTC reagents are added to the hydrogel before, contemporaneously with, and/or after polymerization. In some embodiments, a cell labelling agent is added to the hydrogel before, contemporaneously with, and/or after polymerization. In some embodiments, a cell-penetrating agent is added to the hydrogel before, contemporaneously with, and/or after polymerization.

Hydrogels embedded within biological samples can be cleared using any suitable method. For example, electrophoretic tissue clearing methods can be used to remove biological macromolecules from the hydrogel-embedded sample. In some embodiments, a hydrogel-embedded sample is stored before or after clearing of hydrogel, in a medium (e.g., a mounting medium, methylcellulose, or other semi-solid mediums).

In some embodiments, a method disclosed herein comprises de-crosslinking the reversibly cross-linked biological sample. The de-crosslinking does not need to be complete.

(viii) Tissue Permeabilization and Treatment

In some embodiments, a biological sample can be permeabilized to facilitate transfer of species (such as probes) into the sample. In general, a biological sample can be permeabilized by exposing the sample to one or more permeabilizing agents. Suitable agents for this purpose include, but are not limited to, organic solvents (e.g., acetone, ethanol, and methanol), cross-linking agents (e.g., paraformaldehyde), detergents (e.g., saponin, Triton X-100™ or Tween-20™), and enzymes (e.g., trypsin, proteases). In some embodiments, the biological sample can be incubated with a cellular permeabilizing agent to facilitate permeabilization of the sample. Additional methods for sample permeabilization are described, for example, in Jamur et al., Method Mol. Biol. 588:63-66, 2010, the entire contents of which are incorporated herein by reference. Any suitable method for sample permeabilization can generally be used in connection with the samples described herein.

In some embodiments, the biological sample can be permeabilized by adding one or more lysis reagents to the sample. Examples of suitable lysis agents include, but are not limited to, bioactive reagents such as lysis enzymes that are used for lysis of different cell types, e.g., gram positive or negative bacteria, plants, yeast, mammalian, such as lysozymes, achromopeptidase, lysostaphin, labiase, kitalase, lyticase, and a variety of other commercially available lysis enzymes.

Other lysis agents can additionally or alternatively be added to the biological sample to facilitate permeabilization. For example, surfactant-based lysis solutions can be used to lyse sample cells. Lysis solutions can include ionic surfactants such as, for example, sarcosyl and sodium dodecyl sulfate (SDS). More generally, chemical lysis agents can include, without limitation, organic solvents, chelating agents, detergents, surfactants, and chaotropic agents.

In some embodiments, the biological sample can be permeabilized by non-chemical permeabilization methods. For example, non-chemical permeabilization methods that can be used include, but are not limited to, physical lysis techniques such as electroporation, mechanical permeabilization methods (e.g., bead beating using a homogenizer and grinding balls to mechanically disrupt sample tissue structures), acoustic permeabilization (e.g., sonication), and thermal lysis techniques such as heating to induce thermal permeabilization of the sample.

Additional reagents can be added to a biological sample to perform various functions prior to analysis of the sample. In some embodiments, DNase and RNase inactivating agents or inhibitors such as proteinase K, and/or chelating agents such as EDTA, can be added to the sample. For example, a method disclosed herein may comprise a step for increasing accessibility of a nucleic acid for binding, e.g., a denaturation step to increase accessibility of DNA in a cell for hybridization by a probe. For example, proteinase K treatment may be used to free up DNA with proteins bound thereto.

(ix) Selective Enrichment of RNA Species

In some embodiments, where RNA is the analyte, one or more RNA analyte species of interest can be selectively enriched. For example, one or more species of RNA of interest can be selected by addition of one or more oligonucleotides to the sample. In some embodiments, the additional oligonucleotide is a sequence used for priming a reaction by an enzyme (e.g., a polymerase). For example, one or more primer sequences with sequence complementarity to one or more RNAs of interest can be used to amplify the one or more RNAs of interest, thereby selectively enriching these RNAs.

In some aspects, when two or more analytes are analyzed, a first and second probe that is specific for (e.g., specifically hybridizes to) each RNA or cDNA analyte are used. For example, in some embodiments of the methods provided herein, templated ligation is used to detect gene expression in a biological sample. An analyte of interest (such as a protein), bound by a labelling agent or binding agent (e.g., an antibody or epitope binding fragment thereof), wherein the binding agent is conjugated or otherwise associated with a reporter oligonucleotide comprising a reporter sequence that identifies the binding agent, can be targeted for analysis. Probes may be hybridized to the reporter oligonucleotide and ligated in a templated ligation reaction to generate a product for analysis. In some embodiments, gaps between the probe oligonucleotides may first be filled prior to ligation, using, for example, Mu polymerase, DNA polymerase, RNA polymerase, reverse transcriptase, VENT polymerase, Taq polymerase, and/or any combinations, derivatives, and variants (e.g., engineered mutants) thereof. In some embodiments, the assay can further include amplification of templated ligation products (e.g., by multiplex PCR).

Alternatively, one or more species of RNA can be down-selected (e.g., removed) using any of a variety of methods. For example, probes can be administered to a sample that selectively hybridize to ribosomal RNA (rRNA), thereby reducing the pool and concentration of rRNA in the sample. Additionally and alternatively, duplex-specific nuclease (DSN) treatment can remove rRNA (see, e.g., Archer, et al, Selective and flexible depletion of problematic sequences from RNA-seq libraries at the cDNA stage, *BMC Genomics,* 15 401, (2014), the entire contents of which are incorporated herein by reference). Furthermore, hydroxyapatite chromatography can remove abundant species (e.g., rRNA) (see, e.g., Vandernoot, V.A., cDNA normalization by hydroxyapatite chromatography to enrich transcriptome diversity in RNA-seq applications, *Biotechniques,* 53 (6) 373-80, (2012), the entire contents of which are incorporated herein by reference).

A biological sample may comprise one or a plurality of analytes of interest. Methods for performing multiplexed assays to analyze two or more different analytes in a single biological sample are provided.

B. Analytes

The methods and compositions disclosed herein can be used to detect and analyze a wide variety of different analytes. In some aspects, an analyte can include any biological substance, structure, moiety, or component to be analyzed. In some aspects, a target disclosed herein may similarly include any analyte of interest. In some examples, a target or analyte can be directly or indirectly detected. In some aspects, the analytes include one of more target nucleic acids. In some embodiments, an analyte can comprise a nucleic acid which hybridizes to a circular probe disclosed herein. In some embodiments, an analyte can comprise an RNA molecule which hybridizes to a circular probe disclosed herein. In some embodiments, an analyte can bind to a labelling agent comprising a nucleic acid which hybridizes to a circular probe disclosed herein. In some embodiments, an analyte can bind to a labelling agent comprising an RNA molecule which hybridizes to a circular probe disclosed herein.

Analytes can be derived from a specific type of cell and/or a specific sub-cellular region. For example, analytes can be derived from cytosol, from cell nuclei, from mitochondria, from microsomes, and more generally, from any other compartment, organelle, or portion of a cell. Permeabilizing agents that specifically target certain cell compartments and organelles can be used to selectively release analytes from cells for analysis, and/or allow access of one or more reagents (e.g., probes for analyte detection) to the analytes in the cell or cell compartment or organelle.

The analyte may include any biomolecule or chemical compound, including a macromolecule such as a protein or peptide, a lipid or a nucleic acid molecule, or a small molecule, including organic or inorganic molecules. The analyte may be a cell or a microorganism, including a virus, or a fragment or product thereof. An analyte can be any substance or entity for which a specific binding partner (e.g. an affinity binding partner) can be developed. Such a specific binding partner may be a nucleic acid probe (for a nucleic acid analyte) and may lead directly to the generation of a RCA template (e.g. a padlock or other circularizable probe). Alternatively, the specific binding partner may be coupled to a nucleic acid, which may be detected using an RCA strategy, e.g. in an assay which uses or generates a circular nucleic acid molecule which can be the RCA template.

Analytes of particular interest may include nucleic acid molecules, such as DNA (e.g. genomic DNA, mitochondrial DNA, plastid DNA, viral DNA, etc.) and RNA (e.g. mRNA, microRNA, rRNA, snRNA, viral RNA, etc.), and synthetic and/or modified nucleic acid molecules, (e.g. including nucleic acid domains comprising or consisting of synthetic or modified nucleotides such as LNA, PNA, morpholino, etc.), proteinaceous molecules such as peptides, polypeptides, proteins or prions or any molecule which includes a protein or polypeptide component, etc., or fragments thereof, or a lipid or carbohydrate molecule, or any molecule which comprise a lipid or carbohydrate component. The analyte may be a single molecule or a complex that contains two or more molecular subunits, e.g. including but not limited to protein-DNA complexes, which may or may not be covalently bound to one another, and which may be the same or different. Thus, in addition to cells or microorganisms, such a complex analyte may also be a protein complex or protein interaction. Such a complex interaction may thus be a homo- or hetero-multimer. Aggregates of molecules, e.g. proteins, may also be target analytes, for example aggregates of the same protein or different proteins. The analyte may also be a complex between proteins or peptides and nucleic acid molecules such as DNA or RNA, e.g. interactions between proteins and nucleic acids, e.g. regulatory factors, such as transcription factors, and DNA or RNA.

(i) Endogenous Analytes

In some embodiments, an analyte herein is endogenous to a biological sample and can include nucleic acid analytes and non-nucleic acid analytes. Methods and compositions disclosed herein can be used to analyze nucleic acid analytes (e.g., using a nucleic acid probe or probe set that directly or indirectly hybridizes to a nucleic acid analyte) and/or non-nucleic acid analytes (e.g., using a labelling agent that comprises a reporter oligonucleotide and binds directly or indirectly to a non-nucleic acid analyte) in any suitable combination.

Examples of non-nucleic acid analytes include, but are not limited to, lipids, carbohydrates, peptides, proteins, glycoproteins (N-linked or O-linked), lipoproteins, phosphoproteins, specific phosphorylated or acetylated variants of proteins, amidation variants of proteins, hydroxylation variants of proteins, methylation variants of proteins, ubiquitylation variants of proteins, sulfation variants of proteins, viral coat proteins, extracellular and intracellular proteins, antibodies, and antigen binding fragments. In some embodiments, the analyte is inside a cell or on a cell surface, such as a transmembrane analyte or one that is attached to the cell membrane. In some embodiments, the analyte can be an organelle (e.g., nuclei or mitochondria). In some embodiments, the analyte is an extracellular analyte, such as a secreted analyte. Exemplary analytes include, but are not limited to, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, an extracellular matrix protein, a posttranslational modification (e.g., phosphorylation, glycosylation, ubiquitination, nitrosylation, methylation, acetylation or lipidation) state of a cell surface protein, a gap junction, and an adherens junction.

Examples of nucleic acid analytes include DNA analytes such as single-stranded DNA (ssDNA), double-stranded DNA (dsDNA), genomic DNA, methylated DNA, specific methylated DNA sequences, fragmented DNA, mitochondrial DNA, in situ synthesized PCR products, and RNA/DNA hybrids. The DNA analyte can be a transcript of another nucleic acid molecule (e.g., DNA or RNA such as mRNA) present in a tissue sample.

Examples of nucleic acid analytes also include RNA analytes such as various types of coding and non-coding RNA. Examples of the different types of RNA analytes include messenger RNA (mRNA), including a nascent RNA, a pre-mRNA, a primary-transcript RNA, and a processed RNA, such as a capped mRNA (e.g., with a 5' 7-methyl guanosine cap), a polyadenylated mRNA (poly-A tail at the 3' end), and a spliced mRNA in which one or more introns have been removed. Also included in the analytes disclosed herein are non-capped mRNA, a non-polyadenylated mRNA, and a non-spliced mRNA. The RNA analyte can be a transcript of another nucleic acid molecule (e.g., DNA or RNA such as viral RNA) present in a tissue sample. Examples of a non-coding RNAs (ncRNA) that is not translated into a protein include transfer RNAs (tRNAs) and ribosomal RNAs (rRNAs), as well as small non-coding RNAs such as microRNA (miRNA), small interfering RNA (siRNA), Piwi-interacting RNA (piRNA), small nucleolar RNA (snoRNA), small nuclear RNA (snRNA), extracellular RNA (exRNA), small Cajal body-specific RNAs (scaRNAs), and the long ncRNAs such as Xist and HOTAIR. The RNA can be small (e.g., less than 200 nucleic acid bases in length) or large (e.g., RNA greater than 200 nucleic acid bases in length). Examples of small RNAs include 5.8S ribosomal RNA (rRNA), 5S rRNA, tRNA, miRNA, siRNA, snoRNAs, piRNA, tRNA-derived small RNA (tsRNA), and small rDNA-derived RNA (srRNA). The RNA can be double-stranded RNA or single-stranded RNA. The RNA can be circular RNA. The RNA can be a bacterial IRNA (e.g., 16s rRNA or 23s rRNA).

In some embodiments described herein, an analyte may be a denatured nucleic acid, wherein the resulting denatured nucleic acid is single-stranded. The nucleic acid may be denatured, for example, optionally using formamide, heat, or both formamide and heat. In some embodiments, the nucleic acid is not denatured for use in a method disclosed herein.

In certain embodiments, an analyte can be extracted from a live cell. Processing conditions can be adjusted to ensure that a biological sample remains live during analysis, and analytes are extracted from (or released from) live cells of the sample. Live cell-derived analytes can be obtained only once from the sample, or can be obtained at intervals from a sample that continues to remain in viable condition.

Methods and compositions disclosed herein can be used to analyze any number of analytes. For example, the number of analytes that are analyzed can be at least about 2, at least about 3, at least about 4, at least about 5, at least about 6, at least about 7, at least about 8, at least about 9, at least about 10, at least about 11, at least about 12, at least about 13, at least about 14, at least about 15, at least about 20, at least about 25, at least about 30, at least about 40, at least about 50, at least about 100, at least about 1,000, at least about 10,000, at least about 100,000 or more different analytes present in a region of the sample or within an individual feature of the substrate.

In any embodiment described herein, the analyte comprises a target sequence. In some embodiments, the target sequence may be endogenous to the sample, generated in the sample, added to the sample, or associated with an analyte in the sample. In some embodiments, the target sequence is a single-stranded target sequence (e.g., a sequence in a rolling circle amplification product). In some embodiments, the analytes comprise one or more single-stranded target sequences. In one aspect, a first single-stranded target sequence is not identical to a second single-stranded target sequence. In another aspect, a first single-stranded target sequence is identical to one or more second single-stranded target sequence. In some embodiments, the one or more second single-stranded target sequence is comprised in the same analyte (e.g., nucleic acid) as the first single-stranded target sequence. Alternatively, the one or more second single-stranded target sequence is comprised in a different analyte (e.g., nucleic acid) from the first single-stranded target sequence.

(ii) Labelling Agents

In some embodiments, provided herein are methods and compositions for analyzing endogenous analytes (e.g., RNA, ssDNA, and cell surface or intracellular proteins and/or metabolites) in a sample using one or more labelling agents. In some embodiments, an analyte labelling agent may include an agent that interacts with an analyte (e.g., an endogenous analyte in a sample). In some embodiments, the labelling agents can comprise a reporter oligonucleotide that is indicative of the analyte or portion thereof interacting with the labelling agent. For example, the reporter oligonucleotide may comprise a barcode sequence that permits identification of the labelling agent. In some cases, the sample contacted by the labelling agent can be further contacted with a probe (e.g., a single-stranded probe sequence), that hybridizes to a reporter oligonucleotide of the labelling agent, in order to identify the analyte associated with the labelling agent. In some embodiments, the analyte labelling agent comprises an analyte binding moiety and a labelling agent barcode domain comprising one or more barcode sequences, e.g., a barcode sequence that corresponds to the analyte binding moiety and/or the analyte. An analyte binding moiety barcode includes to a barcode that is associated with or otherwise identifies the analyte binding moiety. In some embodiments, by identifying an analyte binding moiety by identifying its associated analyte binding moiety barcode, the analyte to which the analyte binding moiety binds can also be identified. An analyte binding moiety barcode can be a nucleic acid sequence of a given length and/or sequence that is associated with the analyte binding moiety. An analyte binding moiety barcode can generally include any of the variety of aspects of barcodes described herein.

In some embodiments, the method comprises one or more post-fixing (also referred to as post-fixation) steps after contacting the sample with one or more labelling agents.

In the methods and systems described herein, one or more labelling agents capable of binding to or otherwise coupling to one or more features may be used to characterize analytes, cells and/or cell features. In some instances, cell features include cell surface features. Analytes may include, but are not limited to, a protein, a receptor, an antigen, a surface protein, a transmembrane protein, a cluster of differentiation protein, a protein channel, a protein pump, a carrier protein, a phospholipid, a glycoprotein, a glycolipid, a cell-cell interaction protein complex, an antigen-presenting complex, a major histocompatibility complex, an engineered T-cell receptor, a T-cell receptor, a B-cell receptor, a chimeric antigen receptor, a gap junction, an adherens junction, or any combination thereof. In some instances, cell features may include intracellular analytes, such as proteins, protein modifications (e.g., phosphorylation status or other post-translational modifications), nuclear proteins, nuclear membrane proteins, or any combination thereof.

In some embodiments, an analyte binding moiety may include any molecule or moiety capable of binding to an analyte (e.g., a biological analyte, e.g., a macromolecular constituent). A labelling agent may include, but is not limited to, a protein, a peptide, an antibody (or an epitope binding fragment thereof), a lipophilic moiety (such as cholesterol), a cell surface receptor binding molecule, a receptor ligand, a small molecule, a bi-specific antibody, a bi-specific T-cell engager, a T-cell receptor engager, a B-cell receptor engager, a pro-body, an aptamer, a monobody, an affimer, a darpin, and a protein scaffold, or any combination thereof. The labelling agents can include (e.g., are attached to) a reporter oligonucleotide that is indicative of the cell surface feature to which the binding group binds. For example, the reporter oligonucleotide may comprise a barcode sequence that permits identification of the labelling agent. For example, a labelling agent that is specific to one type of cell feature (e.g., a first cell surface feature) may have coupled thereto a first reporter oligonucleotide, while a labelling agent that is specific to a different cell feature (e.g., a second cell surface feature) may have a different reporter oligonucleotide coupled thereto. For a description of exemplary labelling agents, reporter oligonucleotides, and methods of use, see, e.g., U.S. Pat. No. 10,550,429; U.S. Pat. Pub. 20190177800; and U.S. Pat. Pub. 20190367969, which are each incorporated by reference herein in their entirety.

In some embodiments, an analyte binding moiety includes one or more antibodies or antigen binding fragments thereof. The antibodies or antigen binding fragments including the analyte binding moiety can specifically bind to a target analyte. In some embodiments, the analyte is a protein (e.g., a protein on a surface of the biological sample (e.g., a cell) or an intracellular protein). In some embodiments, a plurality of analyte labelling agents comprising a plurality of analyte binding moieties bind a plurality of analytes present in a biological sample. In some embodiments, the plurality of analytes includes a single species of analyte (e.g., a single species of polypeptide). In some embodiments in which the plurality of analytes includes a single species of analyte, the analyte binding moieties of the plurality of analyte labelling agents are the same. In some embodiments in which the plurality of analytes includes a single species of analyte, the analyte binding moieties of the plurality of analyte labelling agents are the different (e.g., members of the plurality of analyte labelling agents can have two or more species of analyte binding moieties, wherein each of the two or more species of analyte binding moieties binds a single species of analyte, e.g., at different binding sites). In some embodiments, the plurality of analytes includes multiple different species of analyte (e.g., multiple different species of polypeptides).

In other instances, e.g., to facilitate sample multiplexing, a labelling agent that is specific to a particular cell feature may have a first plurality of the labelling agent (e.g., an antibody or lipophilic moiety) coupled to a first reporter oligonucleotide and a second plurality of the labelling agent coupled to a second reporter oligonucleotide.

In some aspects, these reporter oligonucleotides may comprise nucleic acid barcode sequences that permit identification of the labelling agent which the reporter oligonucleotide is coupled to. The selection of oligonucleotides as the reporter may provide advantages of being able to generate significant diversity in terms of sequence, while also being readily attachable to most biomolecules, e.g., antibodies, etc., as well as being readily detected, e.g., using sequencing.

Attachment (coupling) of the reporter oligonucleotides to the labelling agents may be achieved through any of a variety of direct or indirect, covalent or non-covalent associations or attachments. For example, oligonucleotides may be covalently attached to a portion of a labelling agent (such a protein, e.g., an antibody or antibody fragment) using chemical conjugation techniques (e.g., Lightning-Link® antibody labelling kits available from Innova Biosciences), as well as other non-covalent attachment mechanisms, e.g., using biotinylated antibodies and oligonucleotides (or beads that include one or more biotinylated linker, coupled to oligonucleotides) with an avidin or streptavidin linker. Antibody and oligonucleotide biotinylation techniques are available. See, e.g., Fang, et al., "Fluoride-Cleavable Biotinylation Phosphoramidite for 5'-end-Labelling and Affinity Purification of Synthetic Oligonucleotides," Nucleic Acids Res. Jan. 15, 2003; 31 (2): 708-715, which is entirely incorporated herein by reference for all purposes. Likewise, protein and peptide biotinylation techniques have been developed and are readily available. See, e.g., U.S. Pat. No. 6,265,552, which is entirely incorporated herein by reference for all purposes. Furthermore, click reaction chemistry may be used to couple reporter oligonucleotides to labelling agents. Commercially available kits, such as those from Thunderlink and Abcam, and techniques common in the art may be used to couple reporter oligonucleotides to labelling agents as appropriate. In another example, a labelling agent is indirectly (e.g., via hybridization) coupled to a reporter oligonucleotide comprising a barcode sequence that identifies the label agent. For instance, the labelling agent may be directly coupled (e.g., covalently bound) to a hybridization oligonucleotide that comprises a sequence that hybridizes with a sequence of the reporter oligonucleotide. Hybridization of the hybridization oligonucleotide to the reporter oligonucleotide couples the labelling agent to the reporter oligonucleotide. In some embodiments, the reporter oligonucleotides are releasable from the labelling agent, such as upon application of a stimulus. For example, the reporter oligonucleotide may be attached to the labeling agent through a labile bond (e.g., chemically labile, photolabile, thermally labile, etc.) as generally described for releasing molecules from supports elsewhere herein. In some instances, the reporter oligonucleotides described herein may include one or more functional sequences that can be used in subsequent processing.

In some cases, the labelling agent can comprise a reporter oligonucleotide and a label. A label can be fluorophore, a radioisotope, a molecule capable of a colorimetric reaction, a magnetic particle, or any other suitable molecule or compound capable of detection. The label can be conjugated to a labelling agent (or reporter oligonucleotide) either directly or indirectly (e.g., the label can be conjugated to a molecule that can bind to the labelling agent or reporter oligonucleotide). In some cases, a label is conjugated to a first oligonucleotide that is complementary (e.g., hybridizes) to a sequence of the reporter oligonucleotide.

In some embodiments, multiple different species of analytes (e.g., polypeptides) from the biological sample can be subsequently associated with the one or more physical properties of the biological sample. For example, the multiple different species of analytes can be associated with locations of the analytes in the biological sample. Such information (e.g., proteomic information when the analyte binding moiety(ies) recognizes a polypeptide(s)) can be used in association with other spatial information (e.g., genetic information from the biological sample, such as DNA sequence information, transcriptome information (i.e., sequences of transcripts), or both). For example, a cell surface protein of a cell can be associated with one or more physical properties of the cell (e.g., a shape, size, activity, or a type of the cell). The one or more physical properties can be characterized by imaging the cell. The cell can be bound by an analyte labelling agent comprising an analyte binding moiety that binds to the cell surface protein and an analyte binding moiety barcode that identifies that analyte binding moiety. Results of protein analysis in a sample (e.g., a tissue sample or a cell) can be associated with DNA and/or RNA analysis in the sample.

(iii) Products of Endogenous Analyte and/or Labelling Agent

In some embodiments, provided herein are methods and compositions for analyzing one or more products of an endogenous analyte and/or a labelling agent in a biological sample. In some embodiments, an endogenous analyte (e.g., a viral or cellular DNA or RNA) or a product (e.g., a hybridization product, a ligation product, an extension product (e.g., by a DNA or RNA polymerase), a replication product, a transcription/reverse transcription product, and/or an amplification product such as a rolling circle amplification (RCA) product) thereof is analyzed. In some embodiments, a labelling agent that directly or indirectly binds to an analyte in the biological sample is analyzed. In some embodiments, a product (e.g., a hybridization product, a ligation product, an extension product (e.g., by a DNA or RNA polymerase), a replication product, a transcription/reverse transcription product, and/or an amplification product such as a rolling circle amplification (RCA) product) of a labelling agent that directly or indirectly binds to an analyte in the biological sample is analyzed.

(a) Hybridization

In some embodiments, a product of an endogenous analyte and/or a labelling agent is a hybridization product comprising the pairing of substantially complementary or complementary nucleic acid sequences within two different molecules, one of which is the endogenous analyte or the labelling agent (e.g., reporter oligonucleotide attached thereto). The other molecule can be another endogenous molecule or another labelling agent such as a probe. Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another.

Various probes and probe sets can be hybridized to an endogenous analyte and/or a labelling agent and each probe may comprise one or more barcode sequences. Exemplary barcoded probes or probe sets may be based on a padlock probe, a gapped padlock probe, a SNAIL (Splint Nucleotide Assisted Intramolecular Ligation) probe set, a PLAYR (Proximity Ligation Assay for RNA) probe set, a PLISH (Proximity Ligation in situ Hybridization) probe set, and RNA-templated ligation probes. The specific probe or probe set design can vary.

(b) Ligation

In some embodiments, a product of an endogenous analyte and/or a labelling agent is a ligation product. In some embodiments, the ligation product is formed between two or more endogenous analytes. In some embodiments, the ligation product is formed between an endogenous analyte and a labelling agent. In some embodiments, the ligation product is formed between two or more labelling agents. In some embodiments, the ligation product is an intramolecular ligation of an endogenous analyte. In some embodiments, the ligation product is an intramolecular ligation of a labelling agent. The target sequence can be comprised in an endogenous analyte (e.g., nucleic acid such as a genomic DNA or mRNA) or a product thereof (e.g., cDNA from a cellular mRNA transcript), or in a labelling agent (e.g., the reporter oligonucleotide) or a product thereof.

In some embodiments, provided herein is a probe or probe set capable of DNA-templated ligation, such as from a cDNA molecule. See, e.g., U.S. Pat. No. 8,551,710, which is hereby incorporated by reference in its entirety. In some embodiments, provided herein is a probe or probe set capable of RNA-templated ligation. See, e.g., U.S. Pat. Pub. 2020/0224244 which is hereby incorporated by reference in its entirety. In some embodiments, the probe set is a SNAIL probe set. See, e.g., U.S. Pat. Pub. 20190055594, which is hereby incorporated by reference in its entirety. In some embodiments, provided herein is a multiplexed proximity ligation assay. See, e.g., U.S. Pat. Pub. 20140194311 which is hereby incorporated by reference in its entirety. In some embodiments, provided herein is a probe or probe set capable of proximity ligation.

In some embodiments, the ligation involves chemical ligation. In some embodiments, the ligation involves template dependent ligation. In some embodiments, the ligation involves template independent ligation. In some embodiments, the ligation involves enzymatic ligation.

In some embodiments, the enzymatic ligation involves use of a ligase. In some aspects, the ligase used herein comprises an enzyme that is commonly used to join polynucleotides together or to join the ends of a single polynucleotide. An RNA ligase, a DNA ligase, or another variety of ligase can be used to ligate two nucleotide sequences together. Ligases comprise ATP-dependent double-strand polynucleotide ligases, NAD-i-dependent double-strand DNA or RNA ligases and single-strand polynucleotide ligases, for example any of the ligases described in EC 6.5.1.1 (ATP-dependent ligases), EC 6.5.1.2 (NAD+-dependent ligases), EC 6.5.1.3 (RNA ligases). Specific examples of ligases comprise bacterial ligases such as *E. coli* DNA ligase, Tth DNA ligase, *Thermococcus* sp. (strain 9° N) DNA ligase (9° N™ DNA ligase, New England Biolabs), Taq DNA ligase, Ampligase™ (Epicentre Biotechnologies) and phage ligases such as T3 DNA ligase, T4 DNA ligase and T7 DNA ligase and mutants thereof. In some embodiments, the ligase is a T4 RNA ligase. In some embodiments, the ligase is a splintR ligase. In some embodiments, the ligase is a single stranded DNA ligase. In some embodiments, the ligase is a T4 DNA ligase. In some embodiments, the ligase is a ligase that has an DNA-splinted DNA ligase activity. In some embodiments, the ligase is a ligase that has an RNA-splinted DNA ligase activity.

In some embodiments, the ligation herein is a direct ligation. In some embodiments, the ligation herein is an indirect ligation. "Direct ligation" means that the ends of the polynucleotides hybridize immediately adjacently to one another to form a substrate for a ligase enzyme resulting in their ligation to each other (intramolecular ligation). Alternatively, "indirect" means that the ends of the polynucleotides hybridize non-adjacently to one another, e.g., separated by one or more intervening nucleotides or "gaps". In some embodiments, said ends are not ligated directly to each other, but instead occurs either via the intermediacy of one or more intervening (so-called "gap" or "gap-filling" (oligo) nucleotides) or by the extension of the 3' end of a probe to "fill" the "gap" corresponding to said intervening nucleotides (intermolecular ligation). In some cases, the gap of one or more nucleotides between the hybridized ends of the polynucleotides may be "filled" by one or more "gap" (oligo)nucleotide(s) which are complementary to a splint, circularizable probe, or target nucleic acid. The gap may be a gap of 1 to 60 nucleotides or a gap of 1 to 40 nucleotides or a gap of 3 to 40 nucleotides. In specific embodiments, the gap may be a gap of about 1, 2, 3, 4, 5, 6, 7, 8, 9 or 10 or more nucleotides, of any integer (or range of integers) of nucleotides in between the indicated values. In some embodiments, the gap between said terminal regions may be filled by a gap oligonucleotide or by extending the 3' end of a polynucleotide. In some cases, ligation involves ligating the ends of the probe to at least one gap (oligo)nucleotide, such that the gap (oligo)nucleotide becomes incorporated into the resulting polynucleotide. In some embodiments, the ligation herein is preceded by gap filling. In other embodiments, the ligation herein does not require gap filling.

In some embodiments, ligation of the polynucleotides produces polynucleotides with melting temperature higher than that of unligated polynucleotides. Thus, in some aspects, ligation stabilizes the hybridization complex containing the ligated polynucleotides prior to subsequent steps, comprising amplification and detection.

In some aspects, a high fidelity ligase, such as a thermostable DNA ligase (e.g., a Taq DNA ligase), is used, for example, for ligating two or more probes to form a circular probe disclosed herein. Thermostable DNA ligases are active at elevated temperatures, allowing further discrimination by incubating the ligation at a temperature near the melting temperature ($T_m$) of the DNA strands. This selectively reduces the concentration of annealed mismatched substrates (expected to have a slightly lower $T_m$ around the mismatch) over annealed fully base-paired substrates. Thus, high-fidelity ligation can be achieved through a combination of the intrinsic selectivity of the ligase active site and balanced conditions to reduce the incidence of annealed mismatched dsDNA.

In some embodiments, the ligation herein is a proximity ligation of ligating two (or more) nucleic acid sequences that are in proximity with each other, e.g., through enzymatic means (e.g., a ligase). In some embodiments, proximity ligation can include a "gap-filling" step that involves incorporation of one or more nucleic acids by a polymerase, based on the nucleic acid sequence of a template nucleic acid molecule, spanning a distance between the two nucleic acid molecules of interest (see, e.g., U.S. Pat. No. 7,264,929, the entire contents of which are incorporated herein by reference). A wide variety of different methods can be used for proximity ligating nucleic acid molecules, including (but not limited to) "sticky-end" and "blunt-end" ligations. Additionally, single-stranded ligation can be used to perform proximity ligation on a single-stranded nucleic acid molecule. Sticky-end proximity ligations involve the hybridization of complementary single-stranded sequences between the two nucleic acid molecules to be joined, prior to the ligation event itself. Blunt-end proximity ligations generally do not include hybridization of complementary regions from each nucleic acid molecule because both nucleic acid molecules lack a single-stranded overhang at the site of ligation.

(c) Primer Extension and Amplification

In some embodiments, a product is a primer extension product of an analyte, a labelling agent, a probe or probe set bound to the analyte (e.g., a dumbbell probe bound to genomic DNA, mRNA, or cDNA), or a probe or probe set bound to the labelling agent (e.g., a dumbbell probe bound to one or more reporter oligonucleotides from the same or different labelling agents).

A primer is generally a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases. A primer, may in some cases, refer to a primer binding sequence. A primer extension reaction generally refers to any method where two nucleic acid sequences become linked (e.g., hybridized) by an overlap of their respective terminal complementary nucleic acid sequences (e.g., 3' termini). Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

In some embodiments, a product of an endogenous analyte and/or a labelling agent is an amplification product of one or more polynucleotides, for instance, a circular probe or circularizable probe or probe set. In some embodiments, the amplifying is achieved by performing rolling circle amplification (RCA). In other embodiments, a primer that hybridizes to the circular probe or circularized probe is added and used as such for amplification. In some embodiments, the RCA comprises a linear RCA, a branched RCA, a dendritic RCA, or any combination thereof.

In some embodiments, the amplification is performed at a temperature between or between about 20° C. and about 60° C. In some embodiments, the amplification is performed at a temperature between or between about 30° C. and about 40° C. In some aspects, the amplification step, such as the rolling circle amplification (RCA) is performed at a temperature between at or about 25° C. and at or about 50° C., such as at or about 25° C., 27° C., 29° C., 31° C., 33° C., 35° C., 37° C., 39° C., 41° C., 43° C., 45° C., 47° C., or 49° C.

In some embodiments, upon addition of a DNA polymerase in the presence of appropriate dNTP precursors and other cofactors, a primer is elongated to produce multiple copies of the circular template. This amplification step can utilize isothermal amplification or non-isothermal amplification. In some embodiments, after the formation of the hybridization complex and association of the amplification probe, the hybridization complex is rolling-circle amplified to generate a cDNA nanoball (i.e., amplicon) containing multiple copies of the cDNA. Techniques for rolling circle amplification (RCA) include linear RCA, a branched RCA, a dendritic RCA, or any combination thereof. (See, e.g., Baner et al, Nucleic Acids Research, 26:5073-5078, 1998; Lizardi et al, Nature Genetics 19:226, 1998; Mohsen et al., Acc Chem Res. 2016 Nov. 15; 49 (11): 2540-2550; Schweitzer et al. Proc. Natl Acad. Sci. USA 97:101 13-1 19, 2000; Faruqi et al, BMC Genomics 2:4, 2000; Nallur et al, Nucl. Acids Res. 29: el 18, 2001; Dean et al. Genome Res. 1 1:1095-1099, 2001; Schweitzer et al, Nature Biotech. 20:359-365, 2002; U.S. Pat. Nos. 6,054,274, 6,291,187, 6,323,009, 6,344,329 and 6,368,801). Exemplary polymerases for use in RCA comprise DNA polymerase such phi29 (φ29) polymerase, Klenow fragment, *Bacillus stearothermophilus* DNA polymerase (BST), T4 DNA polymerase, T7 DNA polymerase, or DNA polymerase I. In some aspects, DNA polymerases that have been engineered or mutated to have desirable characteristics can be employed. In some embodiments, the polymerase is phi29 DNA polymerase.

In some aspects, during the amplification step, modified nucleotides can be added to the reaction to incorporate the modified nucleotides in the amplification product (e.g., nanoball). Exemplary of the modified nucleotides comprise amine-modified nucleotides. In some aspects of the methods, for example, for anchoring or cross-linking of the generated amplification product (e.g., nanoball) to a scaffold, to cellular structures and/or to other amplification products (e.g., other nanoballs). In some aspects, the amplification products comprises a modified nucleotide, such as an amine-modified nucleotide. In some embodiments, the amine-modified nucleotide comprises an acrylic acid N-hydroxysuccinimide moiety modification. Examples of other amine-modified nucleotides comprise, but are not limited to, a 5-Aminoallyl-dUTP moiety modification, a 5-Propargylamino-dCTP moiety modification, a N6-6-Aminohexyl-dATP moiety modification, or a 7-Deaza-7-Propargylamino-dATP moiety modification.

In some embodiments, the method comprises using a circular construct hybridized to the nucleic acid of interest as a template for rolling circle amplification (RCA). In some embodiments, the RCA comprises a linear RCA. In some embodiments, the RCA comprises a branched RCA. In some embodiments, the RCA comprises a dendritic RCA. In some embodiments, the RCA comprises any combination of the foregoing. In some embodiments, the circular nucleic acid is a construct formed using ligation. In some embodiments, the circular construct is formed using template primer extension followed by ligation. In some embodiments, the circular construct is formed by providing an insert between ends to be ligated. In some embodiments, the circular construct is formed using a combination of any of the foregoing. In some embodiments, the ligation is a DNA-DNA templated ligation. In some embodiments, the ligation is an RNA-RNA templated ligation. Exemplary RNA-templated ligation probes and methods are described in US 2020/0224244 which is incorporated herein by reference in its entirety. In some embodiments, the ligation is an RNA-DNA templated ligation. In some embodiments, a splint is provided as a template for ligation.

In some embodiments, the method comprises contacting the biological sample with an amplification primer for RCA of the circular probe. In some instances, the amplification primer may also be complementary to the target nucleic acid and the circular probe. In some embodiments, a washing step is performed to remove any unbound probes, primers, etc. In some embodiments, the wash is a stringency wash. Washing steps can be performed at any point during the process to remove non-specifically bound probes, probes that have ligated, etc.

In some instances, upon addition of a DNA polymerase in the presence of appropriate dNTP precursors and other cofactors, the amplification primer is elongated by replication of multiple copies of the template. The amplification step can utilize isothermal amplification or non-isothermal amplification. In some embodiments, after the formation of the hybridization complex and RNase digestion to decircularize any circular probes not hybridized to the target nucleic acid, the circular probe is rolling-circle amplified to generate a RCA product (e.g., amplicon) containing multiple copies of the circular.

Suitable examples of DNA polymerases that can be used include, but are not limited to: *E. coli* DNA polymerase I, Bsu DNA polymerase, Bst DNA polymerase, Taq DNA polymerase, VENT™ DNA polymerase, DEEPVENT™ DNA polymerase, LongAmp® Taq DNA polymerase, LongAmp® Hot Start Taq DNA polymerase, Crimson LongAmp® Taq DNA polymerase, Crimson Taq DNA polymerase, OneTaq® DNA polymerase, OneTaq® Quick-Load® DNA polymerase, Hemo KlenTaq® DNA polymerase, REDTaq® DNA polymerase, Phusion® DNA polymerase, Phusion® High-Fidelity DNA polymerase, Platinum Pfx DNA polymerase, AccuPrime Pfx DNA polymerase, Phi29 DNA polymerase, Klenow fragment, Pwo DNA polymerase, Pfu DNA polymerase, T4 DNA polymerase and T7 DNA polymerase enzymes.

In some embodiments, rolling circle amplification products are generated using a polymerase selected from the group consisting of Phi29 DNA polymerase, Phi29-like DNA polymerase, M2 DNA polymerase, B103 DNA polymerase, GA-1 DNA polymerase, phi-PRD1 polymerase, Vent DNA polymerase, Deep Vent DNA polymerase, Vent (exo-) DNA polymerase, KlenTaq DNA polymerase, DNA polymerase I, Klenow fragment of DNA polymerase I, DNA polymerase III, T3 DNA polymerase, T4 DNA polymerase, T5 DNA polymerase, T7 DNA polymerase, Bst polymerase, rBST DNA polymerase, N29 DNA polymerase, TopoTaq DNA polymerase, T7 RNA polymerase, SP6 RNA polymerase, T3 RNA polymerase, and a variant or derivative thereof.

In some embodiments, the one or more polymerases can be employed in the provided methods, for example, for primer extension and/or amplification, e.g., RCA. In some embodiments, the polymerase comprises a modified recombinant Phi29-type polymerase. In some embodiments, the polymerase comprises a modified recombinant Phi29, B103, GA-1, PZA, Phi15, BS32, M2Y, Nf, G1, Cp-1, PRD1, PZE, SF5, Cp-5, Cp-7, PR4, PR5, PR722, or L17 polymerase. In some embodiments, the polymerase comprises a modified recombinant DNA polymerase having at least one amino acid substitution or combination of substitutions as compared to a wildtype Phi29 polymerase. Exemplary polymerases are described in U.S. Pat. Nos. 8,257,954; 8,133,672; 8,343,746; 8,658,365; 8,921,086; and 9,279,155, all of which are herein incorporated by reference. In some embodiments, the polymerase is not directly or indirectly immobilized to a substrate, such as a bead or planar substrate (e.g., glass slide), prior to contacting a sample, although the sample may be immobilized on a substrate. In some embodiments, the polymerase is not attached to a nanopore, a nanopore membrane or an insulating support thereof. In some embodiments, the polymerase is diffusible in the binding mixture and/or in the biological sample. In some embodiments, a preformed complex comprising the polymerase and the RCA primer can be diffusible in the binding mixture and/or in the biological sample.

In some embodiments, the method can further comprise a step of removing molecules of the polymerase and/or the polynucleotide that are not bound to the circular nucleic acid from the biological sample. In some embodiments, the method can further comprise one or more stringency washes between the contacting steps.

In some embodiments, the primer extension reaction mixture can comprise a deoxynucleoside triphosphate (dNTP) or derivative, variant, or analogue thereof. In some embodiments, the primer extension reaction mixture can comprise a catalytic cofactor of the polymerase. In any of the preceding embodiments, the primer extension reaction mixture can comprise a catalytic di-cation, such as $Mg^{2+}$ and/or $Mn^{2+}$. In some embodiments, the primer extension reaction mixture is substantially free of a non-catalytic cation, such as $Ca^{2+}$, $Zn^{2+}$, $Co^{2+}$, $Ni^{2+}$, $Eu^{2+}$, $Sr^{2+}$, $Ba^{2+}$, $Fe^{2+}$, $Eu^{2+}$ and mixtures thereof. In some embodiments, a catalytic cation in the primer extension reaction mixture can replace a non-catalytic cation in complex with the polymerase that is bound to the circular nucleic acid or the RCA primer, thus turning on the polymerase activity of the polymerase. In some embodiments, when the sample is contacted with a primer extension reaction mixture comprising a catalytic di-cation (such as $Mg^{2+}$ and/or $Mn^{2+}$), a non-catalytic cation (such as $Ca^{2+}$, $Zn^{2+}$, $Co^{2+}$, $Ni^{2+}$, $Eu^{2+}$, $Sr^{2+}$, $Ba^{2+}$, $Fe^{2+}$, and/or $Eu^{2+}$) bound to Phi29 is displaced, thereby activating the 5'→3' polymerase activity and the 3'→5' exonuclease (proofreading) activity of Phi29.

In some aspects, the polynucleotides and/or amplification product (e.g., amplicon) can be anchored to a polymer matrix. For example, the polymer matrix can be a hydrogel. In some embodiments, one or more of the polynucleotide probe(s) can be modified to contain functional groups that can be used as an anchoring site to attach the polynucleotide probes and/or amplification product to a polymer matrix. Exemplary modification and polymer matrix that can be employed in accordance with the provided embodiments comprise those described in, for example, WO 2014/163886, WO 2017/079406, US 2016/0024555, US 2018/0251833 and US 2017/0219465. In some examples, the scaffold also contains modifications or functional groups that can react with or incorporate the modifications or functional groups of the probe set or amplification product. In some examples, the scaffold can comprise oligonucleotides, polymers or chemical groups, to provide a matrix and/or support structures.

The amplification products may be immobilized within the matrix generally at the location of the nucleic acid being amplified, thereby creating a localized colony of amplicons. The amplification products may be immobilized within the matrix by steric factors. The amplification products may also be immobilized within the matrix by covalent or noncovalent bonding. In this manner, the amplification products may be considered to be attached to the matrix. By being immobilized to the matrix, such as by covalent bonding or cross-linking, the size and spatial relationship of the original amplicons is maintained. By being immobilized to the matrix, such as by covalent bonding or cross-linking, the amplification products are resistant to movement or unraveling under mechanical stress.

In some aspects, the amplification products are copolymerized and/or covalently attached to the surrounding matrix thereby preserving their spatial relationship and any information inherent thereto. For example, if the amplification products are those generated from DNA or RNA within a cell embedded in the matrix, the amplification products can also be functionalized to form covalent attachment to the matrix preserving their spatial information within the cell thereby providing a subcellular localization distribution pattern. In some embodiments, the provided methods involve embedding the one or more polynucleotide probe sets and/or the amplification products in the presence of hydrogel subunits to form one or more hydrogel-embedded amplification products. In some embodiments, the hydrogel-tissue chemistry described comprises covalently attaching nucleic acids to in situ synthesized hydrogel for tissue clearing, enzyme diffusion, and multiple-cycle sequencing while an existing hydrogel-tissue chemistry method cannot. In some embodiments, to enable amplification product embedding in the tissue-hydrogel setting, amine-modified nucleotides are comprised in the amplification step (e.g., RCA), functionalized with an acrylamide moiety using acrylic acid N-hydroxysuccinimide esters, and copolymerized with acrylamide monomers to form a hydrogel.

In some embodiments, the RCA template may comprise the target analyte, or a part thereof, where the target analyte is a nucleic acid, or it may be provided or generated as a proxy, or a marker, for the analyte. As noted above, many assays are known for the detection of numerous different analytes, which use a RCA-based detection system, e.g., where the signal is provided by generating a RCP from a circular RCA template which is provided or generated in the assay, and the RCP is detected to detect the analyte. The RCP may thus be regarded as a reporter which is detected to detect the target analyte. However, the RCA template may also be regarded as a reporter for the target analyte; the RCP is generated based on the RCA template, and comprises complementary copies of the RCA template. The RCA template determines the signal which is detected, and is thus indicative of the target analyte. As will be described in more detail below, the RCA template may be a probe, or a part or component of a probe, or may be generated from a probe, or it may be a component of a detection assay (e.g., a reagent in a detection assay), which is used as a reporter for the assay, or a part of a reporter, or signal-generation system.

The RCA template used to generate the RCP may thus be a circular (e.g. circularized) reporter nucleic acid molecule, namely from any RCA-based detection assay which uses or generates a circular nucleic acid molecule as a reporter for the assay. Since the RCA template generates the RCP reporter, it may be viewed as part of the reporter system for the assay.

In some embodiments, a product herein includes a molecule or a complex generated in a series of reactions, e.g., hybridization, ligation, extension, replication, transcription/reverse transcription, and/or amplification (e.g., rolling circle amplification), in any suitable combination. For example, a product comprising a target sequence for a probe disclosed herein may be a hybridization complex formed of a cellular nucleic acid in a sample and an exogenously added nucleic acid probe. The exogenously added nucleic acid probe may comprise an overhang that does not hybridize to the cellular nucleic acid but hybridizes to another probe. The exogenously added nucleic acid probe may be optionally ligated to a cellular nucleic acid molecule or another exogenous nucleic acid molecule. In other examples, a product comprising a target sequence for a probe disclosed herein may be an RCP of a circularizable probe or probe set which hybridizes to a cellular nucleic acid molecule (e.g., genomic DNA or mRNA) or product thereof (e.g., a transcript such as cDNA, a DNA-templated ligation product of two probes, or an RNA-templated ligation product of two probes). In other examples, a product comprising a target sequence for a probe disclosed herein may a probe hybridizing to an RCP. The probe may comprise an overhang that does not hybridize to the RCP but hybridizes to another probe. The probe may be optionally ligated to a cellular nucleic acid molecule or another probe, e.g., an anchor probe that hybridize to the RCP.

C. Target Sequences

A target sequence for a probe disclosed herein may be comprised in any analyte disclose herein, including an endogenous analyte (e.g., a viral or cellular nucleic acid), a labelling agent, or a product of an endogenous analyte and/or a labelling agent. In some embodiments, a target sequence for a probe disclosed herein comprises one or more ribonucleotides.

In some aspects, one or more of the target sequences includes one or more barcode(s), e.g., at least two, three, four, five, six, seven, eight, nine, ten, or more barcodes. Barcodes can spatially-resolve molecular components found in biological samples, for example, within a cell or a tissue sample. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI"). In some aspects, a barcode comprises about 4, 5, 6, 7, 8, 9, 10, 11, 12, 13, 14, 15, 16, 17, 18, 19, 20, 21, 22, 23, 24, 25, 26, 27, 28, 29, 30, or more than 30 nucleotides.

In some embodiments, a barcode includes two or more sub-barcodes that together function as a single barcode. For example, a polynucleotide barcode can include two or more polynucleotide sequences (e.g., sub-barcodes) that are separated by one or more non-barcode sequences. In some embodiments, the one or more barcode(s) can also provide a platform for targeting functionalities, such as oligonucleotides, oligonucleotide-antibody conjugates, oligonucleotide-streptavidin conjugates, modified oligonucleotides, affinity purification, detectable moieties, enzymes, enzymes for detection assays or other functionalities, and/or for detection and identification of the polynucleotide.

In any of the preceding embodiments, barcodes (e.g., primary and/or secondary barcode sequences) can be analyzed (e.g., detected or sequenced) using any suitable methods or techniques, including those described herein, such as RNA sequential probing of targets (RNA SPOTs), sequential fluorescent in situ hybridization (seqFISH), single-molecule fluorescent in situ hybridization (smFISH), multiplexed error-robust fluorescence in situ hybridization (MERFISH), in situ sequencing, hybridization-based in situ sequencing (HybISS), targeted in situ sequencing, fluorescent in situ sequencing (FISSEQ), sequencing by synthesis (SBS), sequencing by ligation (SBL), sequencing by hybridization (SBH), or spatially-resolved transcript amplicon readout mapping (STARmap). In any of the preceding embodiments, the methods provided herein can include analyzing the barcodes by sequential hybridization and detection with a plurality of labelled probes (e.g., detection oligos).

In some embodiments, in a barcode sequencing method, barcode sequences are detected for identification of other molecules including nucleic acid molecules (DNA or RNA) longer than the barcode sequences themselves, as opposed to direct sequencing of the longer nucleic acid molecules. In some embodiments, a N-mer barcode sequence comprises $4^N$ complexity given a sequencing read of N bases, and a much shorter sequencing read may be required for molecular identification compared to non-barcode sequencing methods such as direct sequencing. For example, 1024 molecular species may be identified using a 5-nucleotide barcode sequence ($4^5$=1024), whereas 8 nucleotide barcodes can be used to identify up to 65,536 molecular species, a number greater than the total number of distinct genes in the human genome. In some embodiments, the barcode sequences contained in the probes or RCPs are detected, rather than endogenous sequences, which can be an efficient read-out in terms of information per cycle of sequencing. Because the barcode sequences are pre-determined, they can also be designed to feature error detection and correction mechanisms, see, e.g., U.S. Pat. Pub. 20190055594 and U.S. Pat. Pub. 20210164039, which are hereby incorporated by reference in their entirety.

III. Circular Probes with Ribonucleotides and Methods of Use

In some embodiments, described herein are exemplary probe design, compositions and methods for analyzing a biological sample that involves using a circular probe or a plurality of circular probes. Among the provided embodiments include those exemplified in the Examples or those illustrated in the drawings or those described below.

A. Generation of Circular Probes

Figure 1B:
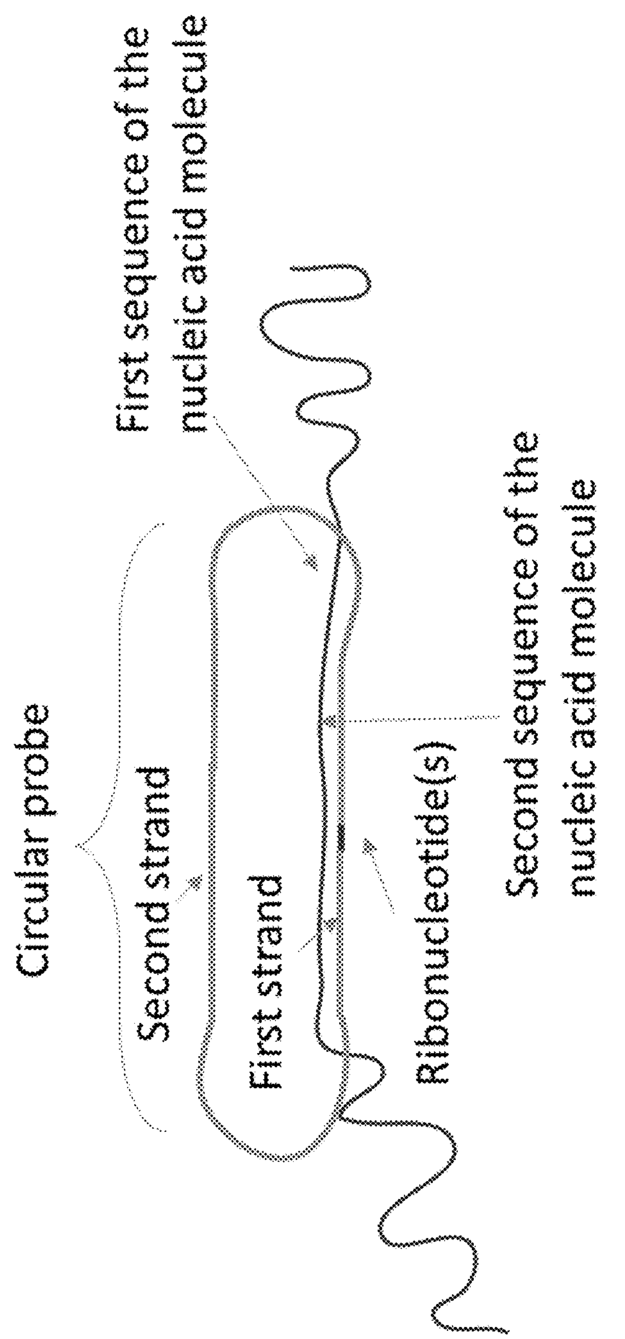

Disclosed herein in some aspects are circular probes that are introduced into a cell or used to otherwise contact a biological sample such as a tissue sample (FIG. 1A, 1B). In certain embodiments, the circular probe is preformed from two or more probes prior to contacting the circular probe with a sample. In certain embodiments, the circular probe is preformed from two or more linear probes (e.g. hairpin probes). In a specific embodiment, two or more linear probes can be connected together to form the circular probe. In certain embodiments, two or more linear probes can be ligated together to form the circular probe. In certain embodiments, the circular probe is constructed by the ligation of at least two hairpin probes, each of which comprise a loop region and a stem region comprising a first strand and a second strand.

Figure 3:
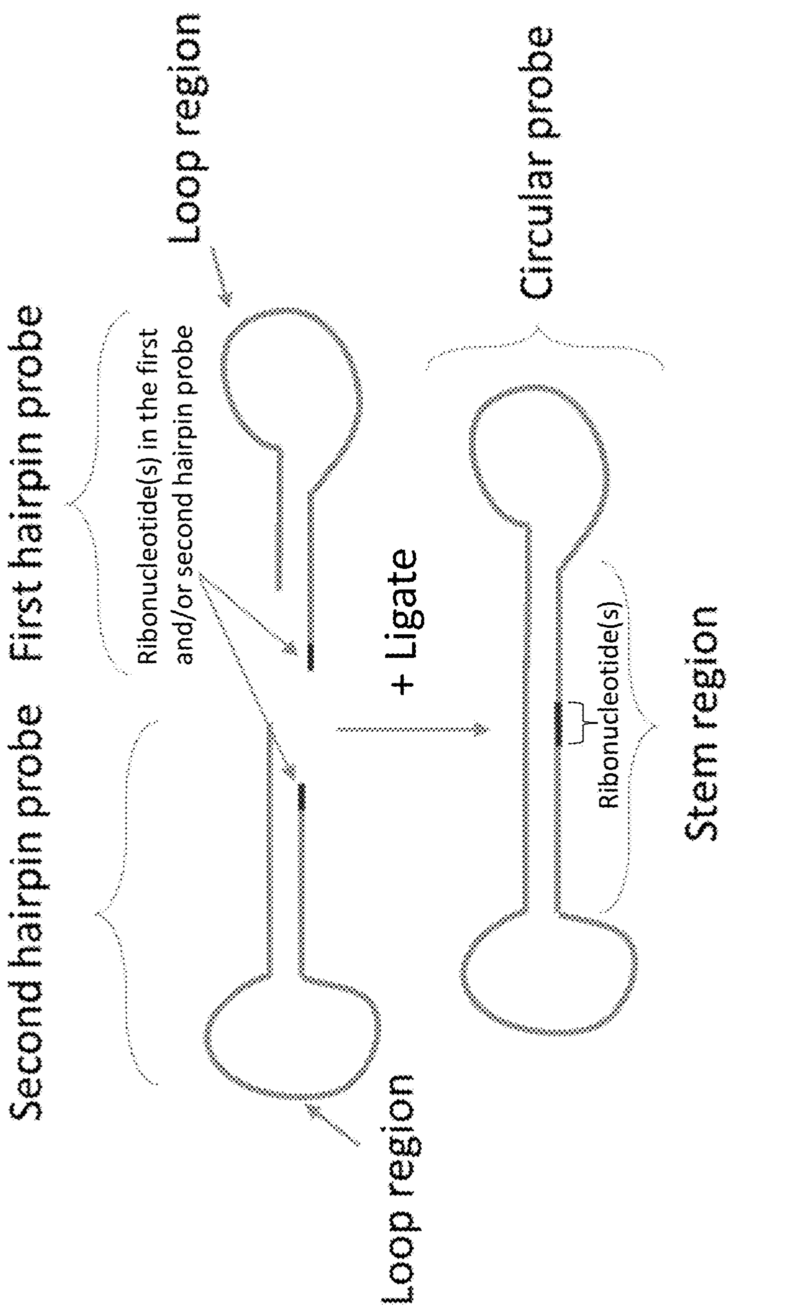
FIG. 3 depicts exemplary circular probe design, where an exemplary first hairpin probe is ligated to an exemplary second hairpin probe. The hairpin probes, composed primarily of DNA, each comprises a loop region and stem region comprised of a complementary first and second strand. This first hairpin comprises a first single-stranded region comprising one or more ribonucleotides. The first single-stranded region can be at the 3' or 5' of the first hairpin probe. The second hairpin comprises a second single-stranded region which can be at the 3' or 5' of the second hairpin probe. The terminal one, two, three, or more nucleotides of the first hairpin probe and/or the second hairpin probe can be ribonucleotides. For instance, a 3' terminal nucleotide of the first hairpin probe and/or a 5' terminal nucleotide of the second hairpin probe can be a ribonucleotide. The first single-stranded region of the first hairpin is complementary to the second single-stranded region of the second hairpin. The first hairpin probe is ligated to the second hairpin probe to produce the exemplary circular probe comprising a stem region and two loop regions.

In some embodiments, a circular probe disclosed herein is a dumbbell probe comprising a central duplex stem region and two loop regions, e.g., as shown in FIG. 3. The lengths of the two loop regions can be the same or different. The two loop regions can be independently of any suitable length, such as about 2, about 5, about 10, about 15, about 20, about 25, about 30, or more nucleotides. The duplex stem region can also be of any suitable length, such as about 5, about 10, about 15, about 20, about 25, about 30, or more base pairs. In some embodiments, the duplex stem region does not contain any single-stranded region. In some embodiments, the duplex stem region comprises one or more single-stranded regions, e.g., in the form of a loop or bulge, that is separate from the two loop regions of the dumbbell probe. In some embodiments, the two loop regions of the dumbbell probe are both single-stranded. In some embodiments, the loop regions are free of any secondary structure. In other embodiments, one or both of the loop regions comprise one or more secondary structures, such as a stem-loop within the loop region.

In some embodiments, a circular probe disclosed herein comprises only one loop region and one stem region. In some embodiments, a circular probe disclosed herein comprises more than two loop regions. In some embodiments, a circular probe disclosed herein comprises more than two stem regions. In some embodiments, a circular probe disclosed herein comprises more loop regions than stem regions. In some embodiments, a circular probe disclosed herein comprises more stem regions than loop regions. In some embodiments, a circular probe disclosed herein comprises equal number of loop regions and stem regions. The circular probe can comprise any suitable number of loop region(s) and stem region(s), as long as a target nucleic acid can hybridize to a sequence (e.g., a toehold region) in one loop region and invade into an adjacent stem region to displace a strand of the stem region from the other strand.

In some embodiments, a stem region of the circular probe comprises a DNA backbone and one or more ribonucleotides. In some embodiments, one or both strands of the stem region can independently comprise one or more ribonucleotides. In some embodiments, a first strand of the stem region comprises one, two, three, four or more ribonucleotides. The two or more ribonucleotides can be contiguous. Alternatively, any two of the ribonucleotides can be separated by one or more intervening deoxyribonucleotides. In some embodiments, a first strand of the stem region comprises one ribonucleotide, two consecutive ribonucleotides, or three consecutive ribonucleotides, and the ribonucleotide(s) can be of substantially equal distance to the 5' and 3' nucleotides of the first strand of the stem region.

The hairpin probes may comprise any of a variety of entities that can hybridize to a nucleic acid, typically by Watson-Crick base pairing, such as DNA, RNA, LNA, PNA, etc. In certain embodiments, the hairpin probes disclosed herein are primarily composed of DNA. In certain embodiments, any one of or both of the first and second hairpin probes that comprise the circular probe comprise one or more ribonucleotides at the 5' and/or the 3'end. In certain embodiments, the first hairpin probe comprises a first 3' single-stranded region comprising one or more ribonucleotides and the second hairpin probe comprises a second 3' single-stranded region that is DNA. In other embodiments, the first hairpin probe comprises a first 3' single-stranded region comprising one or more ribonucleotides, wherein the 3' terminal nucleotide of the first hairpin is a ribonucleotide. In certain embodiments, the second hairpin probe comprises a second 5' end wherein the 5' end of the second hairpin comprises one or more ribonucleotides. In certain embodiments, the first hairpin probe comprises a first 3' single-stranded region, wherein the first 3' single-stranded region or a portion thereof is complementary to the second 3' single-stranded region or a portion thereof of the second hairpin probe. In certain embodiments, the first strand of the stem region comprises no more than one ribonucleotide, no more than two contiguous ribonucleotides, no more than three contiguous ribonucleotides, or no more than four contiguous ribonucleotides.

In some aspects, the provided methods involve a step comprising the use of a ligase to join the 3' single-stranded end of the first hairpin probe with the 5' end of the second probe and the 5' end of the first probe with the 3' single-stranded region of the second hairpin probe. In some aspects, the ligase used in this step can comprise a ligase having an DNA-templated DNA ligase activity and/or an DNA-templated RNA ligase activity. In a further embodiment, the ligase can comprise, but is not limited to, *Chlorella* virus DNA ligase (PBCV DNA ligase), a T4 RNA ligase, a T4 DNA ligase, or a single-stranded DNA (ssDNA) ligase. In a specific embodiment, the T4 RNA ligase is a T4 RNA ligase 2 (T4 Rn12). In some aspects, the ligation results in the circularizing of the first and second hairpin probes to provide the circular probe. In some embodiments, the ligation herein is preceded by gap filling. In other embodiments, the ligation herein does not require gap filling.

In certain embodiments, upon ligation of the two or more hairpin probes, the resulting exemplary circular probe comprises at least one stem region and at least two loop regions (e.g. a dumbbell probe). In a further embodiment, the stem region of the circular probe comprises a first strand and a second strand. In a specific embodiment, the second strand is complementary to the first strand. In some embodiments, the first strand of the stem region comprises no more than one, no more than two, no more than three, or no more than four consecutive ribonucleotides.

In some aspects, the provided methods involve a step comprising the use of an exonuclease to digest probe molecules that are not circularized. In some aspects, the exonuclease can include, but is not limited to, Exonuclease I, Exonuclease II, Exonuclease III, Exonuclease IV, Exonuclease V, or Exonuclease VIII. In a specific embodiment, the exonuclease comprises Exonuclease I (3'→5' exonuclease degradation) and/or Exonuclease II (5'→3' exonuclease degradation). In some aspects, the provided methods involve a step comprising the use of an RNAse to digest hairpin probe molecules that are not circularized. In a specific embodiment, the methods provided herein comprise a digestion step comprising the use of RNAse R to digest probe molecules that are not circularized.

B. Targeted Detection In Situ

Provided herein are methods involving the use of one or more probes for analyzing one or more target nucleic acid(s), such as a target nucleic acid (e.g., a messenger RNA) present in a cell or a biological sample, such as a tissue sample. Also provided are probes, sets of probes, compositions, kits, systems, and devices for use in accordance with the provided methods. In some aspects, the provided methods and systems can be applied to detect, image, quantitate, or determine the presence or absence of one or more target nucleic acid(s) or portions thereof (e.g., presence or absence of sequence variants such as point mutations and SNPs). In some aspects, the provided methods can be applied to detect, image, quantitate, or determine the sequence of one or more target nucleic acid(s), comprising sequence variants such as point mutations and SNPs.

In some aspects, the provided embodiments can be employed for in situ detection and/or sequencing of a target nucleic acid in a cell, e.g., in cells of a biological sample or a sample derived from a biological sample, such as a tissue section on a solid support, such as on a transparent slide. In some aspects, the target nucleic acid molecule is an RNA. In some aspects, the nucleic acid molecule is linear or circular (e.g. a linear RNA or a circular RNA). In further aspects, the target nucleic acid molecule is an mRNA, which can include, but is not limited to, a nascent RNA, a pre-mRNA, a primary-transcript RNA, a processed RNA, a capped mRNA, a non-capped mRNA, a polyadenylated mRNA, a non-polyadenylated mRNA, a spliced mRNA, or a non-spliced mRNA. In a further aspect, the target nucleic acid is non-coding RNA (ncRNA), which can include, but is not limited to a tRNA, tsRNA, rRNA, srRNA, miRNA, siRNA, piRNA, snoRNA, snRNA, exRNA, scaRNA, gRNA, or long ncRNA (lncRNA), optionally wherein the lncRNA is Xist or HOTAIR. In some aspects, the target nucleic acid molecule is a viral, bacterial, fungal, plant, mammalian, or synthetic nucleic acid.

In some aspects, the provided methods involve a step of contacting, or hybridizing, one or more polynucleotides, such as the probe described herein, to a cell or a sample containing the target nucleic acid molecule with a region of interest in order to form a hybridization complex. A nucleic acid probe typically contains a targeting sequence that is able to directly or indirectly bind to at least a portion of a target nucleic acid molecule. The nucleic acid probe may be able to bind to a specific target nucleic acid (e.g., an mRNA or a ncRNA). In some aspects, the provided methods involve a circular probe that is introduced into a cell or used to otherwise contact a biological sample such as a tissue sample. In some aspects, the circular probe comprises a sequence in the loop region which comprises or is a toehold region. In certain embodiments, a first sequence of a target nucleic acid molecule hybridizes to the toehold region of the loop region of the circular probe. In some aspects, if the second sequence of the nucleic acid molecule is complementary to the stem region of the circular probe, the second nucleic acid sequence invades into the stem region, hybridizing to the first strand and displacing the second strand from the first strand. In some aspects, the sequence complementarity between the second sequence and the first strand of the circular probe drives branch migration to displace the second strand from the first strand. In some embodiments, the target nucleic acid molecule will continue to hybridize to the first strand of the circular probe, including hybridizing to the one or more ribonucleotides present in the first strand.

In some aspects, the methods provided herein comprise one or more stringent wash steps in order to remove the unbound and/or nonspecifically-bound circular probes from the sample. In some aspects, the removal of the unbound and/or nonspecifically bound probes may serve to increase the sensitivity and specificity of signal detection. In some aspects, the signal detected is associated with the circular probe or a product thereof generated without de-circularizing the circular probe.

C. RNAse Digestion

As detailed above, in some aspects, the circular probe in the biological sample can be (1) unbound to a target nucleic acid molecule (e.g. an mRNA), (2) bound to an incorrect molecule (non-specific binding), or (3) bound to the correct target molecule (specific binding). In some aspects, the provided methods may involve a step of treating the biological sample with an RNAse in order to improve detection specificity. In some aspects, the RNAse is RNAse H1 or RNAse H2. In some aspects, the biological sample is treated with the RNAse H in the presence of one or more RNAse inhibitors that do not inhibit the RNAse H. In a specific embodiment, the RNAse inhibitor comprises a ribonuclease inhibitor (RI) protein. In some aspects, the RNAse H targets RNA bound to DNA and thus cleaves the circular probes which are either unbound to a target molecule or are non-specifically bound to an incorrect molecule. In some embodiments, an RNAse H used herein cleaves a region where there is a DNA-RNA hybrid and does not cleave DNA-DNA or RNA-RNA duplex.

Figure 2:
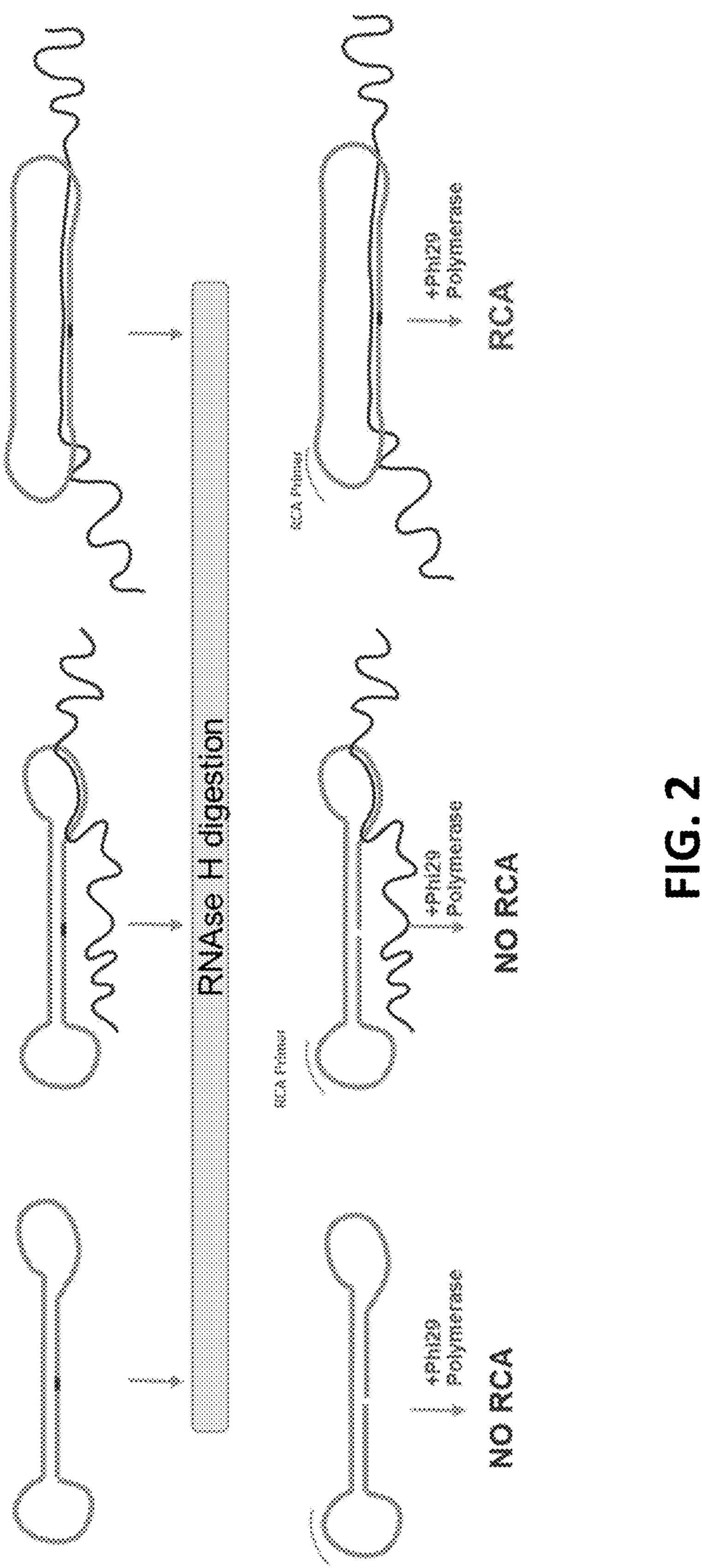
FIG. 2 depicts exemplary circular probes that can be cleaved by RNAse H digestion, an endonuclease that can hydrolyzes RNA in an RNA/DNA hybrid. When the circular probe does not bind to any target RNA in situ, the ribonucleotides in the stem region of the circular probe will be digested (left panel). No RCA will occur with this cleaved probe that is no longer circular. The center panel depicts a first sequence in the RNA molecule binding to a sequence in a loop region. If a second sequence in the RNA molecule adjacent to the first sequence is not complementary to the first strand of the circular probe, the second strand is not displaced from the first strand. Upon addition of RNAse H, the one or more ribonucleotides in the duplex stem region are cleaved, thereby de-circularizing the circular probe and no RCA will take place. In contrast, if the second sequence in the RNA molecule is complementary to the first strand of the stem region, the second strand of the stem region will be displaced from the first strand, allowing continued hybridization of the RNA molecule to the circular probe (right panel), forming a duplex in which the one or more ribonucleotides of the first strand are hybridized to the RNA molecule. RNAse H addition will not cleave the circular probe at the ribonucleotide(s), now part of an RNA/RNA duplex. Because no digestion of ribonucleotides takes place, the circular probe is not cleaved and thus RCA can occur. The RNA molecule or a part thereof can be used to prime the RCA or a separate RCA primer can be provided as shown in FIG. 2. The RCA primer can hybridize to a sequence in either one of the loop regions of the circular probe or to a sequence in the displaced second strand of the stem region.

In a first embodiment, the circular probe in the biological sample is unbound to a target nucleic acid molecule. Upon RNAse H incubation, the RNAse H will digest the one or more ribonucleotides of the first strand of the stem region of the circular probe that remain hybridized to the second strand of the stem region (FIG. 2, left panel). The digestion of the one or more ribonucleotides will cleave the circular probe, thus preventing any RCA from occurring.

In a second embodiment, the circular probe in the biological sample is non-specifically bound to a nucleic acid molecule besides the target molecule. In this embodiment, the first sequence of the nucleic acid molecule has hybridized to the toehold region in the loop region of the circular probe. In this embodiment, the second sequence of the nucleic acid molecule is not complementary to the first strand, thus the nucleic acid molecule will not invade into the stem region and displace the second strand of the circular probe from the first strand (FIG. 2, center panel). Upon RNAse H treatment, the one or more ribonucleotides of the circular probe will be digested since they remain hybridized to DNA in a DNA/RNA hybrid (as opposed to RNA/RNA duplex). In this embodiment, the circularized probe is cleaved and therefore no RCA takes place.

In a third embodiment, the circular probe in the biological sample is specifically bound to the correct target nucleic acid molecule. In some embodiments, the first sequence of the nucleic acid molecule hybridizes to the toehold region in the loop region of the circular probe. In some embodiments, the second sequence of the nucleic acid molecule is complementary to the first strand of the circular probe and thus will hybridize to the first strand, the one or more ribonucleotides in the circular probe hybridizing to the complementary ribonucleotide(s) in the nucleic acid molecule (FIG. 2, right panel).

In this third embodiment, treatment with RNAse H does not cleave the ribonucleotides of the circular probe since they are now bound to the ribonucleotides of the target nucleic acid molecule and not the DNA of the circular probe. In some embodiments, ribonucleotides that are not hybridized to the second strand of the stem region are not cleaved. In some embodiments, the methods described herein comprising the use of a circular probe comprising ribonucleotides and treatment with an RNAse may serve to increase the sensitivity and specificity of signal detection by removing unbound and/or nonspecifically bound probes.

In some embodiments, the second strand of the stem region comprises one or more ribonucleotides.

In some aspects, wherein the circular probe comprises no more than four consecutive ribonucleotides, the methods described herein can comprise contacting the biological sample with an RNAse H2 to digest the ribonucleotides and de-circularize the probe. In some aspects, wherein the circular probe comprises four or more consecutive ribonucleotides, the methods described herein comprise contacting the biological sample with an RNAse H1.

D. Detection of Amplification Product

In some aspects, the provided methods are employed for in situ analysis of target nucleic acids, for example for in situ sequencing or multiplexed analysis in intact tissues or a sample with preserved cellular or tissue structure. In some aspects, the provided methods can be used to detect or determine the identity or amount in situ of single nucleotides of interest in target nucleic acids, for instance of single nucleotide polymorphisms of genes of interest.

In some embodiments, the circular probe may be detected using a detectable label, and/or by using secondary probes able to bind to the circular probe. In some embodiments, the circular probes or secondary probes are compatible with one or more biological and/or chemical reactions. For instance, a circular probe disclosed herein can serve as a template or primer for a polymerase, a template or substrate for a ligase, a substrate for a click chemistry reaction, and/or a substrate for a nuclease (e.g., endonuclease or exonuclease for cleavage or digestion).

In some aspects, the provided methods comprise one or more steps of displacing the first strand from the second strand in order to form a circular probe. In some aspects, the provided methods involve a step of amplifying one of the polynucleotides (e.g., a circular probe), to generate an amplification product. In some aspects, the provided methods involve a step of detecting and/or determining the sequence of all or a portion of the amplification product (for example, of one or more barcodes contained in the amplification product) and/or one or more of the polynucleotides, for instance the circular probe, with or without amplification, for instance any barcodes contained therein. In some aspects, the provided methods involve performing one or more of the steps described herein, simultaneously and/or sequentially.

In some embodiments, the circular probe disclosed herein includes a barcode sequence. The barcode sequences, if present, may be of any length. If more than one barcode sequence is used, the barcode sequences may independently have the same or different lengths, such as at least 5, at least 10, at least 15, at least 20, at least 25, at least 30, at least 35, at least 40, at least 50 nucleotides in length. In some embodiments, the barcode sequence may be no more than 120, no more than 112, no more than 104, no more than 96, no more than 88, no more than 80, no more than 72, no more than 64, no more than 56, no more than 48, no more than 40, no more than 32, no more than 24, no more than 16, or no more than 8 nucleotides in length. Combinations of any of these are also possible, e.g., the barcode sequence may be between 5 and 10 nucleotides, between 8 and 15 nucleotides, etc.

The barcode sequence may be arbitrary or random. In certain cases, the barcode sequences are chosen so as to reduce or minimize homology with other components in a sample, e.g., such that the barcode sequences do not themselves bind to or hybridize with other nucleic acids suspected of being within the cell or other sample. In some embodiments, between a particular barcode sequence and another sequence (e.g., a cellular nucleic acid sequence in a sample or other barcode sequences in probes added to the sample), the homology may be less than 10%, less than 8%, less than 7%, less than 6%, less than 5%, less than 4%, less than 3%, less than 2%, or less than 1%. In some embodiments, the homology may be less than 20, 19, 18, 17, 16, 15, 14, 13, 12, 11, 10, 9, 8, 7, 6, 5, 4, 3, or 2 bases, and in some embodiments, the bases are consecutive bases.

In some aspects, provided herein are in situ assays using microscopy as a readout, e.g., nucleic acid sequencing, hybridization, or other detection or determination methods involving an optical readout. In some aspects, detection or determination of a sequence of one, two, three, four, five, or more nucleotides of a target nucleic acid is performed in situ in a cell in an intact tissue. In some aspects, detection or determination of a sequence is performed such that the localization of the target nucleic acid (or product or a derivative thereof associated with the target nucleic acid) in the originating sample is detected. In some embodiments, the assay comprises detecting the presence or absence of an amplification product or a portion thereof (e.g., RCA product). In some embodiments, a method for spatially profiling analytes such as the transcriptome or a subset thereof in a biological sample is provided. Methods, compositions, kits, devices, and systems for these in situ assays, comprising spatial genomics and transcriptomics assays, are provided. In some embodiments, a provided method is quantitative and preserves the spatial information within a tissue sample without physically isolating cells or using homogenates. In some embodiments, the present disclosure provides methods for high-throughput profiling one or more single nucleotides of interest in a large number of targets in situ, such as transcripts and/or DNA loci, for detecting and/or quantifying nucleic acids in cells, tissues, organs or organisms.

IV. Detection and Analysis

In some aspects, after formation of a hybridization complex comprising nucleic acid probes and/or probe sets described in Section III and further processing (e.g., ligation, extension, amplification, or any combination thereof) as described in Section II, the method further includes detection of the probe or probe set hybridized to the target nucleic acid or any products generated therefrom or a derivative thereof. In any of the embodiments herein, the method can further comprise imaging the biological sample to detect a ligation product or a circularized probe or product thereof. In any of the embodiments herein, a sequence of the ligation product, rolling circle amplification product, or other generated product can be analyzed in situ in the biological sample. In any of the embodiments herein, the imaging can comprise detecting a signal associated with a fluorescently labeled probe that directly or indirectly binds to a rolling circle amplification product of the circularized probe. In any of the embodiments herein, the sequence of the sequence of the ligation product, rolling circle amplification product, or other generated product can be analyzed by sequential hybridization, sequencing by hybridization, sequencing by ligation, sequencing by synthesis, sequencing by binding, or a combination thereof. In some cases, a barcoded analyte (or a product or derivative thereof) can be released from a sample prior to analysis.

In any of the embodiments herein, a sequence associated with the target nucleic acid or the circular probe(s) can comprise one or more barcode sequences or complements thereof. In any of the embodiments herein, the sequence of the rolling circle amplification product can comprise one or more barcode sequences or complements thereof. In any of the embodiments herein, a ligated first-second probe can comprise one or more barcode sequences or complements thereof. In any of the embodiments herein, the one or more barcode sequences can comprise a barcode sequence corresponding to the target nucleic acid. In any of the embodiments herein, the one or more barcode sequences can comprise a barcode sequence corresponding to the sequence of interest, such as variant(s) of a single nucleotide of interest.

In any of the embodiments herein, the detecting step can comprise contacting the biological sample with one or more detectably-labeled probes that directly or indirectly hybridize to the rolling circle amplification product, and dehybridizing the one or more detectably-labeled probes from the rolling circle amplification product. In any of the embodiments herein, the contacting and dehybridizing steps can be repeated with the one or more detectably-labeled probes and/or one or more other detectably-labeled probes that directly or indirectly hybridize to the rolling circle amplification product.

In any of the embodiments herein, the detecting step can comprise contacting the biological sample with one or more intermediate probes that directly or indirectly hybridize to the rolling circle amplification product, wherein the one or more intermediate probes are detectable using one or more detectably-labeled probes. In any of the embodiments herein, the detecting step can further comprise dehybridizing the one or more intermediate probes and/or the one or more detectably-labeled probes from the rolling circle amplification product. In any of the embodiments herein, the contacting and dehybridizing steps can be repeated with the one or more intermediate probes, the one or more detectably-labeled probes, one or more other intermediate probes, and/or one or more other detectably-labeled probes.

In some embodiments, the detection may be spatial, e.g., in two or three dimensions. In some embodiments, the detection may be quantitative, e.g., the amount or concentration of a primary nucleic acid probe (and of a target nucleic acid) may be determined. In some embodiments, the primary probes, intermediate probes, higher order probes, and/or detectably labeled probes may comprise any of a variety of entities able to hybridize a nucleic acid, e.g., DNA, RNA, LNA, and/or PNA, etc., depending on the application.

In some embodiments, a method disclosed herein may also comprise one or more signal amplification components. In some embodiments, the present disclosure relates to the detection of nucleic acids sequences in situ using probe hybridization and generation of amplified signals associated with the probes, wherein background signal is reduced and sensitivity is increased. In some embodiments, the RCA product generated using a method disclosed herein can be detected in with a method that comprises signal amplification.

Exemplary signal amplification methods include targeted deposition of detectable reactive molecules around the site of probe hybridization, targeted assembly of branched structures (e.g., bDNA or branched assay using locked nucleic acid (LNA)), programmed in situ growth of concatemers by enzymatic rolling circle amplification (RCA) (e.g., as described in US 2019/0055594 incorporated herein by reference), hybridization chain reaction, assembly of topologically catenated DNA structures using serial rounds of chemical ligation (clampFISH), signal amplification via hairpin-mediated concatemerization (e.g., as described in US 2020/0362398 incorporated herein by reference), e.g., primer exchange reactions such as signal amplification by exchange reaction (SABER) or SABER with DNA-Exchange (Exchange-SABER). In some embodiments, a non-enzymatic signal amplification method may be used.

The detectable reactive molecules may comprise tyramide, such as used in tyramide signal amplification (TSA) or multiplexed catalyzed reporter deposition (CARD)-FISH. In some embodiments, the detectable reactive molecule may be releasable and/or cleavable from a detectable label such as a fluorophore. In some embodiments, a method disclosed herein comprises multiplexed analysis of a biological sample comprising consecutive cycles of probe hybridization, fluorescence imaging, and signal removal, where the signal removal comprises removing the fluorophore from a fluorophore-labeled reactive molecule (e.g., tyramide). Exemplary detectable reactive reagents and methods are described in U.S. Pat. No. 6,828,109, US 2019/0376956, WO 2019/236841, US 2022/0026433, US 2022/0128565, and US 2021/0222234, all of which are incorporated herein by reference in their entireties.

In some embodiments, hybridization chain reaction (HCR) can be used for signal amplification. HCR is an enzyme-free nucleic acid amplification based on a triggered chain of hybridization of nucleic acid molecules starting from HCR monomers, which hybridize to one another to form a nicked nucleic acid polymer. This polymer is the product of the HCR reaction which is ultimately detected in order to indicate the presence of the target analyte. HCR is described in detail in Dirks and Pierce, 2004, PNAS, 101 (43), 15275-15278 and in U.S. Pat. Nos. 7,632,641 and 7,721,721 (see also US 2006/00234261; Chemeris et al, 2008 Doklady Biochemistry and Biophysics, 419, 53-55; Niu et al, 2010, 46, 3089-3091; Choi et al, 2010, Nat. Biotechnol. 28 (11), 1208-1212; and Song et al, 2012, Analyst, 137, 1396-1401). HCR monomers typically comprise a hairpin, or other metastable nucleic acid structure. In the simplest form of HCR, two different types of stable hairpin monomer, referred to here as first and second HCR monomers, undergo a chain reaction of hybridization events to form a long nicked double-stranded DNA molecule when an "initiator" nucleic acid molecule is introduced. The HCR monomers have a hairpin structure comprising a double stranded stem region, a loop region connecting the two strands of the stem region, and a single stranded region at one end of the double stranded stem region. The single stranded region which is exposed (and which is thus available for hybridization to another molecule, e.g. initiator or other HCR monomer) when the monomers are in the hairpin structure may be known as the "toehold region" (or "input domain"). The first HCR monomers each further comprise a sequence which is complementary to a sequence in the exposed toehold region of the second HCR monomers. This sequence of complementarity in the first HCR monomers may be known as the "interacting region" (or "output domain"). Similarly, the second HCR monomers each comprise an interacting region (output domain), e.g. a sequence which is complementary to the exposed toehold region (input domain) of the first HCR monomers. In the absence of the HCR initiator, these interacting regions are protected by the secondary structure (e.g. they are not exposed), and thus the hairpin monomers are stable or kinetically trapped (also referred to as "metastable"), and remain as monomers (e.g. preventing the system from rapidly equilibrating), because the first and second sets of HCR monomers cannot hybridize to each other. However, once the initiator is introduced, it is able to hybridize to the exposed toehold region of a first HCR monomer, and invade it, causing it to open up. This exposes the interacting region of the first HCR monomer (e.g. the sequence of complementarity to the toehold region of the second HCR monomers), allowing it to hybridize to and invade a second HCR monomer at the toehold region. This hybridization and invasion in turn opens up the second HCR monomer, exposing its interacting region (which is complementary to the toehold region of the first HCR monomers), and allowing it to hybridize to and invade another first HCR monomer. The reaction continues in this manner until all of the HCR monomers are exhausted (e.g. all of the HCR monomers are incorporated into a polymeric chain). Ultimately, this chain reaction leads to the formation of a nicked chain of alternating units of the first and second monomer species. The presence of the HCR initiator is thus required in order to trigger the HCR reaction by hybridization to and invasion of a first HCR monomer. The first and second HCR monomers are designed to hybridize to one another are thus may be defined as cognate to one another. They are also cognate to a given HCR initiator sequence. HCR monomers which interact with one another (hybridize) may be described as a set of HCR monomers or an HCR monomer, or hairpin, system.

An HCR reaction could be carried out with more than two species or types of HCR monomers. For example, a system involving three HCR monomers could be used. In such a system, each first HCR monomer may comprise an interacting region which binds to the toehold region of a second HCR monomer; each second HCR may comprise an interacting region which binds to the toehold region of a third HCR monomer; and each third HCR monomer may comprise an interacting region which binds to the toehold region of a first HCR monomer. The HCR polymerization reaction would then proceed as described above, except that the resulting product would be a polymer having a repeating unit of first, second and third monomers consecutively. Corresponding systems with larger numbers of sets of HCR monomers could readily be conceived. Branching HCR systems have also been devised and described (see, e.g., US 2022/0064697, the content of which is incorporated herein by reference in its entirety), and may be used in the methods herein.

In some embodiments, similar to HCR reactions that use hairpin monomers, linear oligo hybridization chain reaction (LO-HCR) can also be used for signal amplification. In some embodiments, provided herein is a method of detecting an analyte in a sample comprising: (i) performing a linear oligo hybridization chain reaction (LO-HCR), wherein an initiator is contacted with a plurality of LO-HCR monomers of at least a first and a second species to generate a polymeric LO-HCR product hybridized to a target nucleic acid molecule, wherein the first species comprises a first hybridization region complementary to the initiator and a second hybridization region complementary to the second species, wherein the first species and the second species are linear, single-stranded nucleic acid molecules; wherein the initiator is provided in one or more parts, and hybridizes directly or indirectly to or is comprised in the target nucleic acid molecule; and (ii) detecting the polymeric product, thereby detecting the analyte. In some embodiments, the first species and/or the second species may not comprise a hairpin structure. In some embodiments, the plurality of LO-HCR monomers may not comprise a metastable secondary structure. In some embodiments, the LO-HCR polymer may not comprise a branched structure. In some embodiments, performing the linear oligo hybridization chain reaction comprises contacting the target nucleic acid molecule with the initiator to provide the initiator hybridized to the target nucleic acid molecule. In any of the embodiments herein, the target nucleic acid molecule and/or the analyte can be an RCA product.

In some embodiments, detection of nucleic acids sequences in situ includes combination of RCA with an assembly for branched signal amplification. In some embodiments, the assembly complex comprises an amplifier hybridized directly or indirectly (via one or more oligonucleotides) to a sequence of the RCA product. In some embodiments, the assembly includes one or more amplifiers each including an amplifier repeating sequence. In some aspects, the one or more amplifiers is labeled. Described herein is a method of using the aforementioned assembly, including for example, using the assembly in multiplexed error-robust fluorescent in situ hybridization (MERFISH) applications, with branched DNA amplification for signal readout. In some embodiments, the amplifier repeating sequence is about 5-30 nucleotides, and is repeated N times in the amplifier. In some embodiments, the amplifier repeating sequence is about 20 nucleotides, and is repeated at least two times in the amplifier. In some aspects, the one or more amplifier repeating sequence is labeled. For exemplary branched signal amplification, see e.g., U.S. Pat. Pub. No. US20200399689A1 and Xia et al., Multiplexed Detection of RNA using MERFISH and branched DNA amplification. Scientific Reports (2019), each of which is fully incorporated by reference herein.

In some embodiments, the RCA product can be detected in with a method that comprises signal amplification by performing a primer exchange reaction (PER). In various embodiments, a primer with domain on its 3' end binds to a catalytic hairpin, and is extended with a new domain by a strand displacing polymerase. For example, a primer with domain 1 on its 3' ends binds to a catalytic hairpin, and is extended with a new domain 1 by a strand displacing polymerase, with repeated cycles generating a concatemer of repeated domain 1 sequences. In various embodiments, the strand displacing polymerase is Bst. In various embodiments, the catalytic hairpin includes a stopper which releases the strand displacing polymerase. In various embodiments, branch migration displaces the extended primer, which can then dissociate. In various embodiments, the primer undergoes repeated cycles to form a concatemer primer. In various embodiments, a plurality of concatemer primers is contacted with a sample comprising RCA products generated using methods described herein. In various embodiments, the RCA product may be contacted with a plurality of concatemer primers and a plurality of labeled probes. see e.g., U.S. Pat. Pub. No. US20190106733, which is incorporated herein by reference, for exemplary molecules and PER reaction components.

In some embodiments, the methods comprise sequencing all or a portion of the amplification product, such as one or more barcode sequences present in the amplification product.

In some embodiments, the product or derivative of a first and second probe ligated together after hybridizing to the target nucleic acid can be analyzed by sequencing. In some embodiments, the analysis and/or sequence determination comprises sequencing all or a portion of the amplification product or the probe(s) and/or in situ hybridization to the amplification product or the probe(s). In some embodiments, the sequencing step involves sequencing by hybridization, sequencing by ligation, and/or fluorescent in situ sequencing, hybridization-based in situ sequencing and/or wherein the in situ hybridization comprises sequential fluorescent in situ hybridization. In some embodiments, the analysis and/or sequence determination comprises detecting a polymer generated by a hybridization chain reaction (HCR) reaction, see e.g., US 2017/0009278, which is incorporated herein by reference, for exemplary probes and HCR reaction components. In some embodiments, the detection or determination comprises hybridizing to the amplification product a detection oligonucleotide labeled with a fluorophore, an isotope, a mass tag, or a combination thereof. In some embodiments, the detection or determination comprises imaging the amplification product. In some embodiments, the target nucleic acid is an mRNA in a tissue sample, and the detection or determination is performed when the target nucleic acid and/or the amplification product is in situ in the tissue sample.

In some aspects, the provided methods comprise imaging the amplification product (e.g., amplicon) and/or one or more portions of the polynucleotides, for example, via binding of the detection probe and detecting the detectable label. In some embodiments, the detection probe comprises a detectable label that can be measured and quantitated. The terms "label" and "detectable label" comprise a directly or indirectly detectable moiety that is associated with (e.g., conjugated to) a molecule to be detected, e.g., a detectable probe, comprising, but not limited to, fluorophores, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like.

The term "fluorophore" comprises a substance or a portion thereof that is capable of exhibiting fluorescence in the detectable range. Particular examples of labels that may be used in accordance with the provided embodiments comprise, but are not limited to phycoerythrin, Alexa Fluor® dyes, fluorescein, YPet, CyPet, Cascade Blue™, allophycocyanin, Cy®3, Cy®5, Cy®7, rhodamine, dansyl, umbelliferone, Texas Red®, luminol, acradimum esters, biotin, green fluorescent protein (GFP), enhanced green fluorescent protein (EGFP), yellow fluorescent protein (YFP), enhanced yellow fluorescent protein (EYFP), blue fluorescent protein (BFP), red fluorescent protein (RFP), firefly luciferase, *Renilla* luciferase, NADPH, beta-galactosidase, horseradish peroxidase, glucose oxidase, alkaline phosphatase, chloramphenical acetyl transferase, and urease.

Fluorescence detection in tissue samples can often be hindered by the presence of strong background fluorescence. "Autofluorescence" is the general term used to distinguish background fluorescence (that can arise from a variety of sources, including aldehyde fixation, extracellular matrix components, red blood cells, lipofuscin, and the like) from the desired immunofluorescence from the fluorescently labeled antibodies or probes. Tissue autofluorescence can lead to difficulties in distinguishing the signals due to fluorescent antibodies or probes from the general background. In some embodiments, a method disclosed herein utilizes one or more agents to reduce tissue autofluorescence, for example, Autofluorescence Eliminator (Sigma/EMD Millipore), TrueBlack Lipofuscin Autofluorescence Quencher (Biotium), MaxBlock Autofluorescence Reducing Reagent Kit (Max Vision Biosciences), and/or a very intense black dye (e.g., Sudan Black, or comparable dark chromophore).

In some embodiments, a detectable probe containing a detectable label can be used to detect one or more polynucleotide(s) and/or amplification products (e.g., amplicon) described herein. In some embodiments, the methods involve incubating the detectable probe containing the detectable label with the sample, washing unbound detectable probe, and detecting the label, e.g., by imaging.

Examples of detectable labels comprise but are not limited to various radioactive moieties, enzymes, prosthetic groups, fluorescent markers, luminescent markers, bioluminescent markers, metal particles, protein-protein binding pairs and protein-antibody binding pairs. Examples of fluorescent proteins comprise, but are not limited to, yellow fluorescent protein (YFP), green fluorescence protein (GFP), cyan fluorescence protein (CFP), umbelliferone, fluorescein, fluorescein isothiocyanate, rhodamine, dichlorotriazinylamine fluorescein, dansyl chloride and phycoerythrin.

Examples of bioluminescent markers comprise, but are not limited to, luciferase (e.g., bacterial, firefly and click beetle), luciferin, aequorin and the like. Examples of enzyme systems having visually detectable signals comprise, but are not limited to, galactosidases, glucorimidases, phosphatases, peroxidases and cholinesterases. Identifiable markers also comprise radioactive compounds such as $^{125}$I, $^{35}$S, $^{14}$C, or $^{3}$H. Identifiable markers are commercially available from a variety of sources.

Examples of fluorescent labels and nucleotides and/or polynucleotides conjugated to such fluorescent labels comprise those described in, for example, Hoagland, Handbook of Fluorescent Probes and Research Chemicals, Ninth Edition (Molecular Probes, Inc., Eugene, 2002); Keller and Manak, DNA Probes, 2nd Edition (Stockton Press, New York, 1993); Eckstein, editor, Oligonucleotides and Analogues: A Practical Approach (IRL Press, Oxford, 1991); and Wetmur, Critical Reviews in Biochemistry and Molecular Biology, 26:227-259 (1991). In some embodiments, exemplary techniques and methods methodologies applicable to the provided embodiments comprise those described in, for example, U.S. Pat. Nos. 4,757,141, 5,151,507 and 5,091,519. In some embodiments, one or more fluorescent dyes are used as labels for labeled target sequences, for example, as described in U.S. Pat. No. 5,188,934 (4,7-dichlorofluorescein dyes); U.S. Pat. No. 5,366,860 (spectrally resolvable rhodamine dyes); U.S. Pat. No. 5,847,162 (4,7-dichlororhodamine dyes); U.S. Pat. No. 4,318,846 (ether-substituted fluorescein dyes); U.S. Pat. No. 5,800,996 (energy transfer dyes); U.S. Pat. No. 5,066,580 (xanthine dyes); and U.S. Pat. No. 5,688,648 (energy transfer dyes). Labelling can also be carried out with quantum dots, as described in U.S. Pat. Nos. 6,322,901, 6,576,291, 6,423,551, 6,251,303, 6,319,426, 6,426,513, 6,444,143, 5,990,479, 6,207,392, US 2002/0045045 and US 2003/0017264. As used herein, the term "fluorescent label" comprises a signaling moiety that conveys information through the fluorescent absorption and/or emission properties of one or more molecules. Exemplary fluorescent properties comprise fluorescence intensity, fluorescence lifetime, emission spectrum characteristics and energy transfer.

Examples of commercially available fluorescent nucleotide analogues readily incorporated into nucleotide and/or polynucleotide sequences comprise, but are not limited to, Cy®3-dCTP, Cy®3-dUTP, Cy®5-dCTP, Cy®5-dUTP (Amersham Biosciences, Piscataway, N.J.), fluorescein-12-dUTP, tetramethylrhodamine-6-dUTP, Texas Red®-5-dUTP, Cascade Blue™-7-dUTP, BODIPY® TMFL-14-dUTP, BODIPY® TMR-14-dUTP, BODIPY® TMTR-14-dUTP, Rhodamine Green™-5-dUTP, Oregon Green® 488-5-dUTP, Texas Red®-12-dUTP, BODIPY® 630/650-14-dUTP, BODIPY® 650/665-14-dUTP, Alexa Fluor® 488-5-dUTP, Alexa Fluor® 532-5-dUTP, Alexa Fluor® 568-5-dUTP, Alexa Fluor® 594-5-dUTP, Alexa Fluor® 546-14-dUTP, fluorescein-12-UTP, tetramethylrhodamine-6-UTP, Texas Red®-5-UTP, mCherry, Cascade Blue™-7-UTP, BODIPY® FL-14-UTP, BODIPY® TMR-14-UTP, BODIPY® TR-14-UTP, Rhodamine Green™-5-UTP, Alexa Fluor® 488-5-UTP, and Alexa Fluor® 546-14-UTP (Molecular Probes, Inc. Eugene, Oreg.). Methods are known for custom synthesis of nucleotides having other fluorophores (See, Henegariu et al. (2000) Nature Biotechnol. 18:345).

Other examples of fluorophores available for post-synthetic attachment comprise, but are not limited to, Alexa Fluor® 350, Alexa Fluor® 532, Alexa Fluor® 546, Alexa Fluor® 568, Alexa Fluor® 594, Alexa Fluor® 647, BODIPY® 493/503, BODIPY® FL, BODIPY® R6G, BODIPY® 530/550, BODIPY® TMR, BODIPY® 558/568, BODIPY® 558/568, BODIPY® 564/570, BODIPY® 576/589, BODIPY® 581/591, BODIPY® 630/650, BODIPY® 650/665, Cascade Blue™, Cascade Yellow™, Dansyl, Lissamine™ Rhodamine B, Marina Blue®, Oregon Green® 488, Oregon Green® 514, Pacific Blue™, rhodamine 6G, Rhodamine Green™, Rhodamine Red™, tetramethyl rhodamine, Texas Red® (available from Molecular Probes, Inc., Eugene, Oreg.), Cy®2, Cy®3.5, Cy®5.5, and Cy®7 (Amersham Biosciences, Piscataway, N.J.). FRET tandem fluorophores may also be used, comprising, but not limited to, PerCP-Cy®5.5, PE-Cy®5, PE-Cy®5.5, PE-Cy®7, PE-Texas Red®, APC-Cy®7, PE-Alexa Fluor® dyes (610, 647, 680), and APC-Alexa Fluor® dyes.

In some cases, metallic silver or gold particles may be used to enhance signal from fluorescently labeled nucleotide and/or polynucleotide sequences (Lakowicz et al. (2003) Bio Techniques 34:62).

Biotin, or a derivative thereof, may also be used as a label on a nucleotide and/or a polynucleotide sequence, and subsequently bound by a detectably labeled avidin/streptavidin derivative (e.g., phycoerythrin-conjugated streptavidin), or a detectably labeled anti-biotin antibody. Digoxigenin may be incorporated as a label and subsequently bound by a detectably labeled anti-digoxigenin antibody (e.g., fluoresceinated anti-digoxigenin). An aminoallyl-dUTP residue may be incorporated into a polynucleotide sequence and subsequently coupled to an N-hydroxy succinimide (NHS) derivatized fluorescent dye. In general, any member of a conjugate pair may be incorporated into a detection polynucleotide provided that a detectably labeled conjugate partner can be bound to permit detection. As used herein, the term antibody refers to an antibody molecule of any class, or any sub-fragment thereof, such as a Fab.

Other suitable labels for a polynucleotide sequence may comprise fluorescein (FAM), digoxigenin, dinitrophenol (DNP), dansyl, biotin, bromodeoxyuridine (BrdU), hexahistidine (6×His), and phosphor-amino acids (e.g., P-tyr, P-ser, P-thr). In some embodiments the following hapten/antibody pairs are used for detection, in which each of the antibodies is derivatized with a detectable label: biotin/a-biotin, digoxigenin/a-digoxigenin, dinitrophenol (DNP)/a-DNP, 5-Carboxyfluorescein (FAM)/a-FAM.

In some embodiments, a nucleotide and/or an polynucleotide sequence can be indirectly labeled, especially with a hapten that is then bound by a capture agent, e.g., as disclosed in U.S. Pat. Nos. 5,344,757, 5,702,888, 5,354,657, 5,198,537 and 4,849,336, and PCT publication WO 91/17160. Many different hapten-capture agent pairs are available for use. Exemplary haptens comprise, but are not limited to, biotin, des-biotin and other derivatives, dinitrophenol, dansyl, fluorescein, Cy®5, and digoxigenin. For biotin, a capture agent may be avidin, streptavidin, or antibodies. Antibodies may be used as capture agents for the other haptens (many dye-antibody pairs being commercially available, e.g., Molecular Probes, Eugene, Oreg.).

In some aspects, the detecting involves using detection methods such as flow cytometry; sequencing; probe binding and electrochemical detection; pH alteration; catalysis induced by enzymes bound to DNA tags; quantum entanglement; Raman spectroscopy; terahertz wave technology; and/or scanning electron microscopy. In some aspects, the flow cytometry is mass cytometry or fluorescence-activated flow cytometry. In some aspects, the detecting comprises performing microscopy, scanning mass spectrometry or other imaging techniques described herein. In such aspects, the detecting comprises determining a signal, e.g., a fluorescent signal.

In some aspects, the detection (comprising imaging) is carried out using any of a number of different types of microscopy, e.g., confocal microscopy, two-photon microscopy, light-field microscopy, intact tissue expansion microscopy, and/or CLARITY™-optimized light sheet microscopy (COLM).

In some embodiments, fluorescence microscopy is used for detection and imaging of the detection probe. In some aspects, a fluorescence microscope is an optical microscope that uses fluorescence and phosphorescence instead of, or in addition to, reflection and absorption to study properties of organic or inorganic substances. In fluorescence microscopy, a sample is illuminated with light of a wavelength which excites fluorescence in the sample. The fluoresced light, which is usually at a longer wavelength than the illumination, is then imaged through a microscope objective. Two filters may be used in this technique; an illumination (or excitation) filter which ensures the illumination is near monochromatic and at the correct wavelength, and a second emission (or barrier) filter which ensures none of the excitation light source reaches the detector. Alternatively, these functions may both be accomplished by a single dichroic filter. The "fluorescence microscope" comprises any microscope that uses fluorescence to generate an image, whether it is a more simple set up like an epifluorescence microscope, or a more complicated design such as a confocal microscope, which uses optical sectioning to get better resolution of the fluorescent image.

In some embodiments, confocal microscopy is used for detection and imaging of the detection probe. Confocal microscopy uses point illumination and a pinhole in an optically conjugate plane in front of the detector to eliminate out-of-focus signal. As only light produced by fluorescence very close to the focal plane can be detected, the image's optical resolution, particularly in the sample depth direction, is much better than that of wide-field microscopes. However, as much of the light from sample fluorescence is blocked at the pinhole, this increased resolution is at the cost of decreased signal intensity-so long exposures are often required. As only one point in the sample is illuminated at a time, 2D or 3D imaging requires scanning over a regular raster (i.e., a rectangular pattern of parallel scanning lines) in the specimen. The achievable thickness of the focal plane is defined mostly by the wavelength of the used light divided by the numerical aperture of the objective lens, but also by the optical properties of the specimen. The thin optical sectioning makes these types of microscopes particularly good at 3D imaging and surface profiling of samples. CLARITY™-optimized light sheet microscopy (COLM) provides an alternative microscopy for fast 3D imaging of large clarified samples. COLM interrogates large immunolabeled tissues, permits increased speed of acquisition and results in a higher quality of generated data.

Other types of microscopy that can be employed comprise bright field microscopy, oblique illumination microscopy, dark field microscopy, phase contrast, differential interference contrast (DIC) microscopy, interference reflection microscopy (also known as reflected interference contrast, or RIC), single plane illumination microscopy (SPIM), super-resolution microscopy, laser microscopy, electron microscopy (EM), Transmission electron microscopy (TEM), Scanning electron microscopy (SEM), reflection electron microscopy (REM), Scanning transmission electron microscopy (STEM) and low-voltage electron microscopy (LVEM), scanning probe microscopy (SPM), atomic force microscopy (ATM), ballistic electron emission microscopy (BEEM), chemical force microscopy (CFM), conductive atomic force microscopy (C-AFM), electrochemical scanning tunneling microscope (ECSTM), electrostatic force microscopy (EFM), fluidic force microscope (FluidFM), force modulation microscopy (FMM), feature-oriented scanning probe microscopy (FOSPM), kelvin probe force microscopy (KPFM), magnetic force microscopy (MFM), magnetic resonance force microscopy (MRFM), near-field scanning optical microscopy (NSOM) (or SNOM, scanning near-field optical microscopy, SNOM, Piezoresponse Force Microscopy (PFM), PSYM, photon scanning tunneling microscopy (PSTM), PTMS, photothermal microspectroscopy/microscopy (PTMS), SCM, scanning capacitance microscopy (SCM), SECM, scanning electrochemical microscopy (SECM), SGM, scanning gate microscopy (SGM), SHPM, scanning Hall probe microscopy (SHPM), SICM, scanning ion-conductance microscopy (SICM), SPSM spin polarized scanning tunneling microscopy (SPSM), SSRM, scanning spreading resistance microscopy (SSRM), SThM, scanning thermal microscopy (SThM), STM, scanning tunneling microscopy (STM), STP, scanning tunneling potentiometry (STP), SVM, scanning voltage microscopy (SVM), and synchrotron x-ray scanning tunneling microscopy (SXSTM), and intact tissue expansion microscopy (exM).

In some embodiments, sequencing can be performed in situ. In situ sequencing typically involves incorporation of a labeled nucleotide (e.g., fluorescently labeled mononucleotides or dinucleotides) in a sequential, template-dependent manner or hybridization of a labeled primer (e.g., a labeled random hexamer) to a nucleic acid template such that the identities (i.e., nucleotide sequence) of the incorporated nucleotides or labeled primer extension products can be determined, and consequently, the nucleotide sequence of the corresponding template nucleic acid. Aspects of in situ sequencing are described, for example, in Mitra et al., (2003) *Anal. Biochem.* 320, 55-65, and Lee et al., (2014) *Science,* 343 (6177), 1360-1363. In addition, examples of methods and systems for performing in situ sequencing are described in US 2016/0024555, US 2019/0194709, and in U.S. Pat. Nos. 10,138,509, 10,494,662 and 10,179,932. Exemplary techniques for in situ sequencing comprise, but are not limited to, STARmap (described for example in Wang et al., (2018) *Science,* 361 (6499) 5691), MERFISH (described for example in Moffitt, (2016) *Methods in Enzymology,* 572, 1-49), hybridization-based in situ sequencing (HybISS) (described for example in Gyllborg et al., *Nucleic Acids Res* (2020) 48 (19): e112, and FISSEQ (described for example in US 2019/0032121). In some cases, sequencing can be performed after the analytes are released from the biological sample.

In some embodiments, sequencing can be performed by sequencing-by-synthesis (SBS). In some embodiments, a sequencing primer is complementary to sequences at or near the one or more barcode(s). In such embodiments, sequencing-by-synthesis can comprise reverse transcription and/or amplification in order to generate a template sequence from which a primer sequence can bind. Exemplary SBS methods comprise those described for example, but not limited to, US 2007/0166705, US 2006/0188901, U.S. Pat. No. 7,057,026, US 2006/0240439, US 2006/0281109, US 2011/005986, US 2005/0100900, U.S. Pat. No. 9,217,178, US 2009/0118128, US 2012/0270305, US 2013/0260372, and US 2013/0079232.

In some embodiments, sequencing can be performed by sequential fluorescence hybridization (e.g., sequencing by hybridization). Sequential fluorescence hybridization can involve sequential hybridization of detection probes comprising an oligonucleotide and a detectable label.

In some embodiments, sequencing can be performed using single molecule sequencing by ligation. Such techniques utilize DNA ligase to incorporate oligonucleotides and identify the incorporation of such oligonucleotides. The oligonucleotides typically have different labels that are correlated with the identity of a particular nucleotide in a sequence to which the oligonucleotides hybridize. Aspects and features involved in sequencing by ligation are described, for example, in Shendure et al. *Science* (2005), 309:1728-1732, and in U.S. Pat. Nos. 5,599,675; 5,750,341; 6,969,488; 6,172,218; and 6,306,597.

In some embodiments, the barcodes of the circular probes or complements or products thereof are targeted by detectably labeled detection oligonucleotides, such as fluorescently labeled oligonucleotides. In some embodiments, one or more decoding schemes are used to decode the signals, such as fluorescence, for sequence determination. In any of the embodiments herein, barcodes (e.g., primary and/or secondary barcode sequences) can be analyzed (e.g., detected or sequenced) using any suitable methods or techniques, comprising those described herein, such as RNA sequential probing of targets (RNA SPOTs), sequential fluorescent in situ hybridization (seqFISH), single-molecule fluorescent in situ hybridization (smFISH), multiplexed error-robust fluorescence in situ hybridization (MERFISH), hybridization-based in situ sequencing (HybISS), in situ sequencing, targeted in situ sequencing, fluorescent in situ sequencing (FISSEQ), or spatially-resolved transcript amplicon readout mapping (STARmap). In some embodiments, the methods provided herein comprise analyzing the barcodes by sequential hybridization and detection with a plurality of labelled probes (e.g., detection oligonucleotides). Exemplary decoding schemes are described in Eng et al., "Transcriptome-scale Super-Resolved Imaging in Tissues by RNA SeqFISH+," *Nature* 568 (7751): 235-239 (2019); Chen et al., *Science;* 348 (6233): aaa6090 (2015); Gyllborg et al., Nucleic Acids Res (2020) 48 (19): e112; U.S. Pat. No. 10,457,980 B2; US 2016/0369329 A1; WO 2018/026873 A1; and US 2017/0220733 A1, all of which are incorporated by reference in their entirety. In some embodiments, these assays enable signal amplification, combinatorial decoding, and error correction schemes at the same time.

In some embodiments, nucleic acid hybridization can be used for sequencing. These methods utilize labeled nucleic acid decoder probes that are complementary to at least a portion of a barcode sequence. Multiplex decoding can be performed with pools of many different probes with distinguishable labels. Non-limiting examples of nucleic acid hybridization sequencing are described for example in U.S. Pat. No. 8,460,865, and in Gunderson et al., *Genome Research* 14:870-877 (2004).

In some embodiments, real-time monitoring of DNA polymerase activity can be used during sequencing. For example, nucleotide incorporations can be detected through fluorescence resonance energy transfer (FRET), as described for example in Levene et al., *Science* (2003), 299, 682-686, Lundquist et al., *Opt. Lett.* (2008), 33, 1026-1028, and Korlach et al., *Proc. Natl. Acad. Sci. USA* (2008), 105, 1176-1181.

In some aspects, the analysis and/or sequence determination can be carried out at room temperature for best preservation of tissue morphology with low background noise and error reduction. In some embodiments, the analysis and/or sequence determination comprises eliminating error accumulation as sequencing proceeds.

In some embodiments, the analysis and/or sequence determination involves washing to remove unbound polynucleotides, thereafter revealing a fluorescent product for imaging.

V. Compositions and Kits

Also provided herein are kits, for example comprising one or more oligonucleotides disclosed herein, and reagents for performing the methods provided herein, for example reagents required for one or more steps comprising hybridization, ligation, amplification, detection, sequencing, and/or sample preparation as described herein. In some embodiments, the kit further comprises a target nucleic acid. In some embodiments, any or all of the polynucleotides are DNA molecules. In some embodiments, the target nucleic acid is a messenger RNA molecule.

The various components of the kit may be present in separate containers or certain compatible components may be pre-combined into a single container. In some embodiments, the kits further contain instructions for using the components of the kit to practice the provided methods.

In some embodiments, the kits can contain reagents and/or consumables required for performing one or more steps of the provided methods. In some embodiments, the kits contain reagents for fixing, embedding, and/or permeabilizing the biological sample. In some embodiments, the kits contain reagents, such as enzymes and buffers for ligation and/or amplification, such as ligases and/or polymerases. In some aspects, the kit can also comprise any of the reagents described herein, e.g., wash buffer and ligation buffer. In some embodiments, the kits contain reagents for detection and/or sequencing, such as barcode detection probes or detectable labels. In some embodiments, the kits optionally contain other components, for example nucleic acid primers, enzymes and reagents, buffers, nucleotides, modified nucleotides, reagents for additional assays.

In some aspects, the provided embodiments can be applied in an in situ method of analyzing nucleic acid sequences, such as an in situ transcriptomic analysis or in situ sequencing, for example from intact tissues or samples in which the spatial information has been preserved. In some aspects, the embodiments can be applied in an imaging or detection method for multiplexed nucleic acid analysis. In some aspects, the provided embodiments can be used to identify or detect regions of interest in target nucleic acids.

In some aspects, the embodiments can be applied in investigative and/or diagnostic applications, for example, for characterization or assessment of particular cell or a tissue from a subject. Applications of the provided method can comprise biomedical research and clinical diagnostics. For example, in biomedical research, applications comprise, but are not limited to, spatially resolved gene expression analysis for biological investigation or drug screening. In clinical diagnostics, applications comprise, but are not limited to, detecting gene markers such as disease, immune responses, bacterial or viral DNA/RNA for patient samples.

VI. Terminology

Specific terminology is used throughout this disclosure to explain various aspects of the apparatus, systems, methods, and compositions that are described.

Having described some illustrative embodiments of the present disclosure, it should be apparent to those skilled in the art that the foregoing is merely illustrative and not limiting, having been presented by way of example only. Numerous modifications and other illustrative embodiments are within the scope of one of ordinary skill in the art and are contemplated as falling within the scope of the present disclosure. In particular, although many of the examples presented herein involve specific combinations of method acts or system elements, it should be understood that those acts and those elements may be combined in other ways to accomplish the same objectives.

As used herein, the singular forms "a," "an," and "the" include plural referents unless the context clearly dictates otherwise. For example, "a" or "an" means "at least one" or "one or more."

The term "about" as used herein refers to the usual error range for the respective value readily known to the skilled person in this technical field. Reference to "about" a value or parameter herein includes (and describes) embodiments that are directed to that value or parameter per se.

Throughout this disclosure, various aspects of the claimed subject matter are presented in a range format. It should be understood that the description in range format is merely for convenience and brevity and should not be construed as an inflexible limitation on the scope of the claimed subject matter. Accordingly, the description of a range should be considered to have specifically disclosed all the possible sub-ranges as well as individual numerical values within that range. For example, where a range of values is provided, it is understood that each intervening value, between the upper and lower limit of that range and any other stated or intervening value in that stated range is encompassed within the claimed subject matter. The upper and lower limits of these smaller ranges may independently be included in the smaller ranges, and are also encompassed within the claimed subject matter, subject to any specifically excluded limit in the stated range. Where the stated range includes one or both of the limits, ranges excluding either or both of those included limits are also included in the claimed subject matter. This applies regardless of the breadth of the range.

Use of ordinal terms such as "first", "second", "third", etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements. Similarly, use of a), b), etc., or i), ii), etc. does not by itself connote any priority, precedence, or order of steps in the claims. Similarly, the use of these terms in the specification does not by itself connote any required priority, precedence, or order.

(i) Barcode

A "barcode" is a label, or identifier, that conveys or is capable of conveying information (e.g., information about an analyte in a sample). A barcode can be part of an analyte, or independent of an analyte. A barcode can be attached to an analyte. A particular barcode can be unique relative to other barcodes.

Barcodes can have a variety of different formats. For example, barcodes can include polynucleotide barcodes, random nucleic acid and/or amino acid sequences, and synthetic nucleic acid and/or amino acid sequences. A barcode can be attached to an analyte or to another moiety or structure in a reversible or irreversible manner. A barcode can be added to, for example, a fragment of a deoxyribonucleic acid (DNA) or ribonucleic acid (RNA) sample before or during sequencing of the sample. Barcodes can allow for identification and/or quantification of individual sequencing-reads (e.g., a barcode can be or can include a unique molecular identifier or "UMI").

Barcodes can spatially-resolve molecular components found in biological samples, for example, at single-cell resolution. In some embodiments, a barcode includes two or more sub-barcodes that together function as a single barcode. For example, a polynucleotide barcode can include two or more polynucleotide sequences (e.g., sub-barcodes) that are separated by one or more non-barcode sequences.

(ii) Nucleic Acid and Nucleotide

The terms "nucleic acid" and "nucleotide" are intended to be consistent with their use in the art and to include naturally-occurring species or functional analogs thereof. Particularly useful functional analogs of nucleic acids are capable of hybridizing to a nucleic acid in a sequence-specific fashion (e.g., capable of hybridizing to two nucleic acids such that ligation can occur between the two hybridized nucleic acids) or are capable of being used as a template for replication of a particular nucleotide sequence. Naturally-occurring nucleic acids generally have a backbone containing phosphodiester bonds. An analog structure can have an alternate backbone linkage including any established variety. Naturally-occurring nucleic acids generally have a deoxyribose sugar (e.g., found in deoxyribonucleic acid (DNA)) or a ribose sugar (e.g. found in ribonucleic acid (RNA)).

A nucleic acid can contain nucleotides having any of a variety of analogs of these sugar moieties. A nucleic acid can include native or non-native nucleotides. In this regard, a native deoxyribonucleic acid can have one or more bases selected from the group consisting of adenine (A), thymine (T), cytosine (C), or guanine (G), and a ribonucleic acid can have one or more bases selected from the group consisting of uracil (U), adenine (A), cytosine (C), or guanine (G).

(iii) Probe and Target

A "probe" or a "target," when used in reference to a nucleic acid or sequence of a nucleic acids, is intended as a semantic identifier for the nucleic acid or sequence in the context of a method or composition, and does not limit the structure or function of the nucleic acid or sequence beyond what is expressly indicated.

(iv) Oligonucleotide and Polynucleotide

The terms "oligonucleotide" and "polynucleotide" are used interchangeably to refer to a single-stranded multimer of nucleotides from about 2 to about 500 nucleotides in length. Oligonucleotides can be synthetic, made enzymatically (e.g., via polymerization), or using a "split-pool" method. Oligonucleotides can include ribonucleotide monomers (e.g., oligoribonucleotides) and/or deoxyribonucleotide monomers (e.g., oligodeoxyribonucleotides). In some examples, oligonucleotides can include a combination of both deoxyribonucleotide monomers and ribonucleotide monomers in the oligonucleotide (e.g., random or ordered combination of deoxyribonucleotide monomers and ribonucleotide monomers). An oligonucleotide can be 4 to 10, 10 to 20, 21 to 30, 31 to 40, 41 to 50, 51 to 60, 61 to 70, 71 to 80, 80 to 100, 100 to 150, 150 to 200, 200 to 250, 250 to 300, 300 to 350, 350 to 400, or 400-500 nucleotides in length, for example. Oligonucleotides can include one or more functional moieties that are attached (e.g., covalently or non-covalently) to the multimer structure. For example, an oligonucleotide can include one or more detectable labels (e.g., a radioisotope or fluorophore).

(v) Hybridizing, Hybridize, Annealing, and Anneal

The terms "hybridizing," "hybridize," "annealing," and "anneal" are used interchangeably in this disclosure, and refer to the pairing of substantially complementary or complementary nucleic acid sequences within two different molecules. Pairing can be achieved by any process in which a nucleic acid sequence joins with a substantially or fully complementary sequence through base pairing to form a hybridization complex. For purposes of hybridization, two nucleic acid sequences are "substantially complementary" if at least 60% (e.g., at least 70%, at least 80%, or at least 90%) of their individual bases are complementary to one another.

(vi) Primer

A "primer" is a single-stranded nucleic acid sequence having a 3' end that can be used as a substrate for a nucleic acid polymerase in a nucleic acid extension reaction. RNA primers are formed of RNA nucleotides, and are used in RNA synthesis, while DNA primers are formed of DNA nucleotides and used in DNA synthesis. Primers can also include both RNA nucleotides and DNA nucleotides (e.g., in a random or designed pattern). Primers can also include other natural or synthetic nucleotides described herein that can have additional functionality. In some examples, DNA primers can be used to prime RNA synthesis and vice versa (e.g., RNA primers can be used to prime DNA synthesis). Primers can vary in length. For example, primers can be about 6 bases to about 120 bases. For example, primers can include up to about 25 bases. A primer, may in some cases, refer to a primer binding sequence.

(vii) Primer Extension

A "primer extension" refers to any method where two nucleic acid sequences become linked (e.g., hybridized) by an overlap of their respective terminal complementary nucleic acid sequences (e.g., 3' termini). Such linking can be followed by nucleic acid extension (e.g., an enzymatic extension) of one, or both termini using the other nucleic acid sequence as a template for extension. Enzymatic extension can be performed by an enzyme including, but not limited to, a polymerase and/or a reverse transcriptase.

(viii) Nucleic Acid Extension

A "nucleic acid extension" generally involves incorporation of one or more nucleic acids (e.g., A, G, C, T, U, nucleotide analogs, or derivatives thereof) into a molecule (such as, but not limited to, a nucleic acid sequence) in a template-dependent manner, such that consecutive nucleic acids are incorporated by an enzyme (such as a polymerase or reverse transcriptase), thereby generating a newly synthesized nucleic acid molecule. For example, a primer that hybridizes to a complementary nucleic acid sequence can be used to synthesize a new nucleic acid molecule by using the complementary nucleic acid sequence as a template for nucleic acid synthesis. Similarly, a 3' polyadenylated tail of an mRNA transcript that hybridizes to a poly (dT) sequence (e.g., capture domain) can be used as a template for single-strand synthesis of a corresponding cDNA molecule.

(ix) PCR Amplification

A "PCR amplification" refers to the use of a polymerase chain reaction (PCR) to generate copies of genetic material, including DNA and RNA sequences. Suitable reagents and conditions for implementing PCR are described, for example, in U.S. Pat. Nos. 4,683,202, 4,683,195, 4,800,159, 4,965,188, and 5,512,462, the entire contents of each of which are incorporated herein by reference. In a typical PCR amplification, the reaction mixture includes the genetic material to be amplified, an enzyme, one or more primers that are employed in a primer extension reaction, and reagents for the reaction. The oligonucleotide primers are of sufficient length to provide for hybridization to complementary genetic material under annealing conditions. The length of the primers generally depends on the length of the amplification domains, but will typically be at least 4 bases, at least 5 bases, at least 6 bases, at least 8 bases, at least 9 bases, at least 10 base pairs (bp), at least 11 bp, at least 12 bp, at least 13 bp, at least 14 bp, at least 15 bp, at least 16 bp, at least 17 bp, at least 18 bp, at least 19 bp, at least 20 bp, at least 25 bp, at least 30 bp, at least 35 bp, and can be as long as 40 bp or longer, where the length of the primers will generally range from 18 to 50 bp. The genetic material can be contacted with a single primer or a set of two primers (forward and reverse primers), depending upon whether primer extension, linear or exponential amplification of the genetic material is desired.

In some embodiments, the PCR amplification process uses a DNA polymerase enzyme. The DNA polymerase activity can be provided by one or more distinct DNA polymerase enzymes. In certain embodiments, the DNA polymerase enzyme is from a bacterium, e.g., the DNA polymerase enzyme is a bacterial DNA polymerase enzyme. For instance, the DNA polymerase can be from a bacterium of the genus *Escherichia, Bacillus, Thermophilus*, or *Pyrococcus*.

Suitable examples of DNA polymerases that can be used include, but are not limited to: *E. coli* DNA polymerase I, Bsu DNA polymerase, Bst DNA polymerase, Taq DNA polymerase, VENT™ DNA polymerase, DEEPVENT™ DNA polymerase, LongAmp® Taq DNA polymerase, LongAmp® Hot Start Taq DNA polymerase, Crimson LongAmp® Taq DNA polymerase, Crimson Taq DNA polymerase, OneTaq® DNA polymerase, OneTaq® Quick-Load® DNA polymerase, Hemo KlenTaq® DNA polymerase, REDTaq® DNA polymerase, Phusion® DNA polymerase, Phusion® High-Fidelity DNA polymerase, Platinum Pfx DNA polymerase, AccuPrime Pfx DNA polymerase, Phi29 DNA polymerase, Klenow fragment, Pwo DNA polymerase, Pfu DNA polymerase, T4 DNA polymerase and T7 DNA polymerase enzymes.

The term "DNA polymerase" includes not only naturally-occurring enzymes but also all modified derivatives thereof, including also derivatives of naturally-occurring DNA polymerase enzymes. For instance, in some embodiments, the DNA polymerase can have been modified to remove 5'-3' exonuclease activity. Sequence-modified derivatives or mutants of DNA polymerase enzymes that can be used include, but are not limited to, mutants that retain at least some of the functional, e.g. DNA polymerase activity of the wild-type sequence. Mutations can affect the activity profile of the enzymes, e.g. enhance or reduce the rate of polymerization, under different reaction conditions, e.g. temperature, template concentration, primer concentration, etc. Mutations or sequence-modifications can also affect the exonuclease activity and/or thermostability of the enzyme.

In some embodiments, PCR amplification can include reactions such as, but not limited to, a strand-displacement amplification reaction, a rolling circle amplification reaction, a ligase chain reaction, a transcription-mediated amplification reaction, an isothermal amplification reaction, and/or a loop-mediated amplification reaction.

In some embodiments, PCR amplification uses a single primer that is complementary to the 3' tag of target DNA fragments. In some embodiments, PCR amplification uses a first and a second primer, where at least a 3' end portion of the first primer is complementary to at least a portion of the 3' tag of the target nucleic acid fragments, and where at least a 3' end portion of the second primer exhibits the sequence of at least a portion of the 5' tag of the target nucleic acid fragments. In some embodiments, a 5' end portion of the first primer is non-complementary to the 3' tag of the target nucleic acid fragments, and a 5' end portion of the second primer does not exhibit the sequence of at least a portion of the 5' tag of the target nucleic acid fragments. In some embodiments, the first primer includes a first universal sequence and/or the second primer includes a second universal sequence.

In some embodiments, the PCR amplification products can be ligated to additional sequences using a DNA ligase enzyme. The DNA ligase activity can be provided by one or more distinct DNA ligase enzymes. In some embodiments, the DNA ligase enzyme is from a bacterium, e.g., the DNA ligase enzyme is a bacterial DNA ligase enzyme. In some embodiments, the DNA ligase enzyme is from a virus (e.g., a bacteriophage). For instance, the DNA ligase can be T4 DNA ligase. Other enzymes appropriate for the ligation step include, but are not limited to, Tth DNA ligase, Taq DNA ligase, *Thermococcus* sp. (strain 90N) DNA ligase (90NTM DNA ligase, available from New England Biolabs, Ipswich, MA), and Ampligase™ (available from Epicentre Biotechnologies, Madison, WI). Derivatives, e.g. sequence-modified derivatives, and/or mutants thereof, can also be used.

In some embodiments, genetic material is amplified by reverse transcription polymerase chain reaction (RT-PCR). The desired reverse transcriptase activity can be provided by one or more distinct reverse transcriptase enzymes, suitable examples of which include, but are not limited to: M-MLV, MuLV, AMV, HIV, ArrayScript™, MultiScribe™, ThermoScript™, and SuperScript® I, II, III, and IV enzymes. "Reverse transcriptase" includes not only naturally occurring enzymes, but all such modified derivatives thereof, including also derivatives of naturally-occurring reverse transcriptase enzymes.

In addition, reverse transcription can be performed using sequence-modified derivatives or mutants of M-MLV, MuLV, AMV, and HIV reverse transcriptase enzymes, including mutants that retain at least some of the functional, e.g. reverse transcriptase, activity of the wild-type sequence. The reverse transcriptase enzyme can be provided as part of a composition that includes other components, e.g. stabilizing components that enhance or improve the activity of the reverse transcriptase enzyme, such as RNase inhibitor(s), inhibitors of DNA-dependent DNA synthesis, e.g. actinomycin D. Many sequence-modified derivative or mutants of reverse transcriptase enzymes, e.g. M-MLV, and compositions including unmodified and modified enzymes are commercially available, e.g. ArrayScript™, MultiScribe™, ThermoScript™, and SuperScript® I, II, III, and IV enzymes.

Certain reverse transcriptase enzymes (e.g. Avian Myeloblastosis Virus (AMV) Reverse Transcriptase and Moloney Murine Leukemia Virus (M-MuLV, MMLV) Reverse Transcriptase) can synthesize a complementary DNA strand using both RNA (cDNA synthesis) and single-stranded DNA (ssDNA) as a template. Thus, in some embodiments, the reverse transcription reaction can use an enzyme (reverse transcriptase) that is capable of using both RNA and ssDNA as the template for an extension reaction, e.g. an AMV or MMLV reverse transcriptase.

In some embodiments, the quantification of RNA and/or DNA is carried out by real-time PCR (also known as quantitative PCR or qPCR), using established techniques such as, but not limited to, "TAQMAN™" or "SYBR®", or on capillaries ("LightCycler® Capillaries"). In some embodiments, the quantification of genetic material is determined by optical absorbance and with real-time PCR. In some embodiments, the quantification of genetic material is determined by digital PCR. In some embodiments, the genes analyzed can be compared to a reference nucleic acid extract (DNA and RNA) corresponding to the expression (mRNA) and quantity (DNA) in order to compare expression levels of the target nucleic acids.

(xi) Label, Detectable Label, and Optical Label

The terms "detectable label," "optical label," and "label" are used interchangeably herein to refer to a directly or indirectly detectable moiety that is associated with (e.g., conjugated to) a molecule to be detected, e.g., a probe for in situ assay or an analyte. The detectable label can be directly detectable by itself (e.g., radioisotope labels or fluorescent labels) or, in the case of an enzymatic label, can be indirectly detectable, e.g., by catalyzing chemical alterations of a substrate compound or composition, which substrate compound or composition is directly detectable. Detectable labels can be suitable for small scale detection and/or suitable for high-throughput screening. As such, suitable detectable labels include, but are not limited to, radioisotopes, fluorophores, chemiluminescent compounds, bioluminescent compounds, and dyes.

The detectable label can be qualitatively detected (e.g., optically or spectrally), or it can be quantified. Qualitative detection generally includes a detection method in which the existence or presence of the detectable label is confirmed, whereas quantifiable detection generally includes a detection method having a quantifiable (e.g., numerically reportable) value such as an intensity, duration, polarization, and/or other properties.

In some embodiments, a plurality of detectable labels can be attached to a detectably labeled probe. For example, detectable labels can be incorporated during nucleic acid polymerization or amplification (e.g., Cy5®-labeled nucleotides, such as Cy5®-dCTP). Any suitable detectable label can be used. In some embodiments, the detectable label is a fluorophore. Examples of fluorophores include: 7-AAD (7-Aminoactinomycin D), Acridine Orange (+DNA), Acridine Orange (+RNA), Alexa Fluor® 350, Alexa Fluor® 430, Alexa Fluor® 488, Alexa Fluor® 532, Alexa Fluor® 546, Alexa Fluor® 555, Alexa Fluor® 568, Alexa Fluor® 594, Alexa Fluor® 633, Alexa Fluor® 647, Alexa Fluor® 660, Alexa Fluor® 680, Alexa Fluor® 700, Alexa Fluor® 750, Allophycocyanin (APC), AMCA/AMCA-X, 7-Aminoactinomycin D (7-AAD), 7-Amino-4-methylcoumarin, 6-Aminoquinoline, Aniline Blue, ANS, APC-Cy®7, ATTO-TAG™ CBQCA, ATTO-TAG™ FQ, Auramine O-Feulgen, BCECF (high pH), BFP (Blue Fluorescent Protein), BFP/GFP FRET, BOBO™-1/BO-PRO™-1, BOBO™-3/BO-PRO™-3, BODIPY® FL, BODIPY® TMR, BODIPY® TR-X, BODIPY® 530/550, BODIPY® 558/568, BODIPY® 564/570, BODIPY® 581/591, BODIPY® 630/650-X, BODIPY® 650-665-X, BTC, Calcein, Calcein Blue, Calcium Crimson™, Calcium Green-1™, Calcium Orange™, Calcofluor® White, 5-Carboxyfluoroscein (5-FAM™), 5-Carboxynaphthofluoroscein, 6-Carboxyrhodamine 6G, 5-Carboxytetramethylrhodamine (5-TAMRA™), Carboxy-X-rhodamine (5-ROX™), Cascade Blue™, Cascade Yellow™, CCF2 (GeneBLAzer™), CFP (Cyan Fluorescent Protein), CFP/YFP FRET, Chromomycin A3, CI-NERF (low pH), CPM, 6-CR 6G, CTC Formazan, Cy2®, Cy3®, Cy3.5®, Cy5®, Cy5.5®, Cy7®, Cychrome (PE-Cy®5), Dansylamine, Dansyl cadaverine, Dansylchloride, DAPI, Dapoxyl, DCFH, DHR, DIA (4-Di-16-ASP), DiD (DilC18 (5)), DIDS, Dil (DilC18 (3)), DiO (DiOC18 (3)), DiR (DilC18 (7)), Di-4 ANEPPS, Di-8 ANEPPS, DM-NERF (4.5-6.5 pH), DsRed (Red Fluorescent Protein), EBFP, ECFP, EGFP, ELF®-97 alcohol, Eosin, Erythrosin, Ethidium bromide, Ethidium homodimer-1 (EthD-1), Europium (III) Chloride, 5-FAM™ (5-Carboxyfluorescein), Fast Blue, Fluorescein-dT phosphoramidite, FITC, Fluo-3, Fluo-4, FluorX®, Fluoro-Gold™ (high pH), Fluoro-Gold™ (low pH), Fluoro-Jade®, FM® 1-43, Fura-2 (high calcium), Fura-2/BCECF, Fura Red™ (high calcium), Fura Red™/Fluo-3, GeneBLAzer™ (CCF2), GFP Red Shifted (rsGFP), GFP Wild Type, GFP/BFP FRET, GFP/DsRed FRET, Hoechst™ 33342 & 33258, 7-Hydroxy-4-methylcoumarin (pH 9), 1,5 IAEDANS, Indo-1 (high calcium), Indo-1 (low calcium), Indodicarbocyanine, Indotricarbocyanine, JC-1, 6-JOE™, JOJO™-1/JO-PRO™-1, LDS 751 (+DNA), LDS 751 (+RNA), LOLO™-1/LO-PRO™-1, Lucifer Yellow, LysoSensor™ Blue (pH 5), LysoSensor™ Green (pH 5), LysoSensor™ Yellow/Blue (pH 4.2), LysoTracker® Green, LysoTracker® Red, LysoTracker® Yellow, Mag-Fura-2, Mag-Indo-1, Magnesium Green™, Marina Blue®, 4-Methylumbelliferone, Mithramycin, MitoTracker® Green, MitoTracker® Orange, MitoTracker® Red, NBD (amine), Nile Red, Oregon Green® 488, Oregon Green® 500, Oregon Green® 514, Pacific Blue™, PBF1, PE (R-phycoerythrin), PE-Cy®5, PE-Cy®7, PE-Texas Red®, PerCP (Peridinin chlorphyll protein), PerCP-Cy®5.5 (TruRed™), PharRed™ (APC-Cy®7), C-phycocyanin, R-phycocyanin, R-phycoerythrin (PE), PI (Propidium Iodide), PKH26, PKH67, POPO™-1/PO-PRO™-1, POPO™-3/PO-PRO™-3, Propidium Iodide (PI), PyMPO, Pyrene, Pyronin Y, Quantam Red (PE-Cy®5), Quinacrine Mustard, R670 (PE-Cy®5), Red 613 (PE-Texas Red®), Red Fluorescent Protein (DsRed), Resorufin, RH 414, Rhod-2, Rhodamine B, Rhodamine Green™, Rhodamine Red™, Rhodamine Phalloidin, Rhodamine 110, Rhodamine 123, 5-ROX™ (carboxy-X-rhodamine), S65A, S65C, S65L, S65T, SBFI, SITS, SNAFL®-1 (high pH), SNAFL®-2, SNARF®-1 (high pH), SNARF®-1 (low pH), Sodium Green™, SpectrumAqua®, SpectrumGreen® #1, SpectrumGreen® #2, SpectrumOrange®, SpectrumRed®, SYTOR 11, SYTOR 13, SYTOR 17, SYTOR 45, SYTOX® Blue, SYTOX® Green, SYTOX® Orange, 5-TAMRA™ (5-Carboxytetramethylrhodamine), Tetramethylrhodamine (TRITC), Texas Red®/Texas Red®-X, Texas Red®-X (NHS Ester), Thiadicarbocyanine, Thiazole Orange, TOTO®-1/TO-PRO®-1, TOTO®-3/TO-PRO®-3, TO-PRO®-5, Tri-color (PE-Cy®5), TRITC (Tetramethylrhodamine), TruRed™ (PerCP-Cy®5.5), WW 781, X-Rhodamine (XRITC), Y66F, Y66H, Y66W, YFP (Yellow Fluorescent Protein), YOYO®-1/YO-PRO®-1, YOYO®-3/YO-PRO®-3, 6-FAM™ (Fluorescein), 6-FAM™ (NHS Ester), 6-FAM™ (Azide), HEX™, TAMRA™ (NHS Ester), Yakima Yellow®, MAX, TET™, TEX615, ATTOR 488, ATTOR 532, ATTOR 550, ATTOR 565, ATTOR Rho101, ATTOR 590, ATTO® 633, ATTOR 647N, TYE™ 563, TYE™ 665, TYE™ 705, 5' IRDye® 700, 5' IRDye® 800, 5' IRDye® 800CW (NHS Ester), WellRED D4 Dye, WellRED D3 Dye, WellRED D2 Dye, Lightcycler® 640 (NHS Ester), and Dy 750 (NHS Ester).

As mentioned above, in some embodiments, a detectable label is or includes a luminescent or chemiluminescent moiety. Common luminescent/chemiluminescent moieties include, but are not limited to, peroxidases such as horseradish peroxidase (HRP), soybean peroxidase (SP), alkaline phosphatase, and luciferase. These protein moieties can catalyze chemiluminescent reactions given the appropriate substrates (e.g., an oxidizing reagent plus a chemiluminescent compound. A number of compound families are known to provide chemiluminescence under a variety of conditions. Non-limiting examples of chemiluminescent compound families include 2,3-dihydro-1,4-phthalazinedione luminol, 5-amino-6,7,8-trimethoxy- and the dimethylamino[ca]benz analog. These compounds can luminesce in the presence of alkaline hydrogen peroxide or calcium hypochlorite and base. Other examples of chemiluminescent compound families include, e.g., 2,4,5-triphenylimidazoles, para-dimethylamino and -methoxy substituents, oxalates such as oxalyl active esters, p-nitrophenyl, N-alkyl acridinum esters, luciferins, lucigenins, or acridinium esters. In some embodiments, a detectable label is or includes a metal-based or mass-based label. For example, small cluster metal ions, metals, or semiconductors may act as a mass code. In some examples, the metals can be selected from Groups 3-15 of the periodic table, e.g., Y, La, Ag, Au, Pt, Ni, Pd, Rh, Ir, Co, Cu, Bi, or a combination thereof.

EXAMPLE

The following example is included for illustrative purposes only and is not intended to limit the scope of the present disclosure.

Example 1: Use of a Circular Probe Comprising Ribonucleotides and RCA to Detect a Target Nucleic Acid This example describes an exemplary use of a circular probe comprising ribonucleotides for analyzing a biological sample. The exemplary circular probe is preformed from a first hairpin probe and a second hairpin probe, both comprising a loop region and a stem region, which are ligated together to produce the circular probe. The hairpin probes are composed primarily of DNA and the first hairpin comprises a first 3' single-stranded region comprising one or more ribonucleotides as depicted in FIG. 3. The first hairpin probe is ligated to the second hairpin probe to produce the exemplary circular probe of FIG. 3, comprising two loop regions and a stem region comprising a first strand (comprising one or more ribonucleotides) and a second strand. In some cases, hairpin probe(s) that do not circularize can be digested with an exonuclease such as Exonuclease-1.

A tissue sample is obtained and cryosectioned onto a glass slide for processing. The tissue is fixed by incubating in paraformaldehyde (PFA). One or more washes is performed and the tissue is then permeabilized. To prepare for probe hybridization, a wash buffer is added to the tissue section. The circular probe is incubated with the thin tissue section sample and hybridization buffer for hybridization of the probe sets to target nucleic acid (e.g., mRNAs) in the sample. As depicted in FIG. 1A, a first sequence of the target nucleic acid molecule can bind to the toehold region in the loop region of the circular probe. The second sequence in the nucleic acid molecule is complementary to the first strand of the circular probe and invades into the stem region, hybridizing to the first strand and displacing the second strand from the first strand as shown in FIG. 1B.

The biological sample is then contacted by RNAse H in order to digest ribonucleotides that remain hybridized to the second strand of the circular probe. As depicted in FIG. 2, if the circular probe does not bind to any target RNA in situ, the ribonucleotides in the stem region of the circular probe will be digested (left panel). As depicted in the center panel of FIG. 2, if the second sequence in the RNA molecule is not complementary to the first strand of the circular probe, the second strand is not displaced from the first strand, and upon addition of RNAse H, the one or more ribonucleotides are cleaved, thereby de-circularizing the circular probe. If the circular probe does not bind a target RNA or if the circular probe non-specifically binds an RNA, the RNAse H treatment will cleave the circular probe and no RCA will take place.

As depicted in the right panel of FIG. 2, the circular probe specifically binds the target RNA molecule and therefore the second sequence in the RNA molecule is complementary to the first strand of the circular probe. The second strand of the circular probe is displaced from the first strand, allowing continued hybridization of the RNA molecule to the circular probe. The contacting of RNAse H to the biological sample does not result in the cleavage of the ribonucleotides in the stem region, as the ribonucleotides are now part or an RNA/RNA duplex, being hybridized to the target RNA molecule. Because no digestion of ribonucleotides takes place, the circular probe is not cleaved and thus RCA occurs.

For the circular probe specifically bound to the target nucleic acid molecule, a primer is used to prime amplification of the circularized probe. The biological sample is then incubated with a rolling-circle amplification (RCA) mixture containing a Phi29 DNA polymerase and dNTPs for RCA of the circularized probes. Fluorescently labeled oligonucleotides complementary to a portion of the RCA product, a barcode contained therein, or a secondary probe attached thereto are incubated with the sample. Multiple cycles of contacting the sample with probes and sequence determination (e.g., using in situ sequencing based on sequencing-by-ligation or sequencing-by-hybridization) can be performed. Fluorescent images can be obtained in each cycle, and one or more wash steps can be performed in a cycle or between cycles.

The present disclosure is not intended to be limited in scope to the particular disclosed embodiments, which are provided, for example, to illustrate various aspects of the disclosure. Various modifications to the compositions and methods described will become apparent from the description and teachings herein. Such variations may be practiced without departing from the true scope and spirit of the disclosure and are intended to fall within the scope of the present disclosure.

The invention claimed is:

1. A method, comprising:

(a) contacting a biological sample comprising a plurality of ribonucleic acid (RNA) molecules with a plurality of circular probes, wherein a first circular probe of the plurality of circular probes comprises:
  (i) a first loop region comprising a sequence complementary to a first sequence of a first RNA molecule of the plurality of RNA molecules,
  (ii) a stem region comprising (1) a first strand complementary to the first RNA molecule, wherein the first strand comprises one or more ribonucleotides, and (2) a second strand comprising deoxyribonucleic acid (DNA) complementary to the first strand, and
  (iii) a second loop region;
(b) hybridizing the first loop region to the first sequence of the first RNA molecule;
(c) displacing the second strand from the first strand and hybridizing the first strand to the first RNA molecule, thereby obtaining a hybridized first circular probe;
(d) after (c), contacting the biological sample with an RNAse, wherein the RNAse cleaves one or more ribonucleotides of a second circular probe of the plurality of circular probes, wherein the one or more ribonucleotides of the second circular probe are not hybridized to an RNA molecule of the plurality of RNA molecules;

(e) performing a rolling circle amplification reaction on the hybridized first circular probe to generate a rolling circle amplification (RCA) product; and (f) detecting the RCA product, thereby detecting the first RNA molecule in the biological sample.

2. The method of claim 1, wherein the second circular probe comprises a stem region comprising (1) a first strand comprising one or more ribonucleotides, and (2) a second strand complementary to the first strand.

3. The method of claim 2, wherein the second circular probe comprises a loop region comprising a sequence complementary to the first sequence of the first RNA molecule.

4. The method of claim 1, wherein the first RNA molecule comprises a sequence of interest, wherein the sequence of interest or a portion thereof is complementary to one or more of the ribonucleotide(s) in the first strand of the first circular probe.

5. The method of claim 3, wherein the first strand of the stem region of the second circular probe does not hybridize to an RNA molecule of the plurality of RNA molecules.

6. The method of claim 1, wherein the first loop region or second loop region of the first circular probe comprises a first barcode sequence corresponding to the first RNA molecule or a sequence of interest therein.

7. The method of claim 1, wherein the RNAse is an RNAse H.

8. The method of claim 7, wherein the biological sample is treated with the RNAse H in the presence of one or more RNAse inhibitors that do not inhibit the RNAse H.

9. The method of claim 1, wherein the RNAse is an RNAse H1 or an RNAse H2.

10. The method of claim 1, wherein the RNAse does not cleave the first RNA molecule or a portion thereof hybridized to the first circular probe.

11. The method of claim 1, wherein the RNAse cleaves the first RNA molecule or a portion thereof hybridized to the first circular probe.

12. The method of claim 1, wherein performing the rolling circle amplification reaction on the hybridized first circular probe comprises contacting the biological sample with a primer that hybridizes to a sequence in the first loop region or second loop region.

13. The method of claim 1, wherein the detecting step comprises:

contacting the RCA product with one or more detectable probes that hybridize to the RCA product.

14. The method of claim 1, wherein the detecting step comprises:

contacting the RCA product with one or more intermediate probes that hybridize to the RCA product, wherein each intermediate probe comprises a sequence that hybridizes to the RCA product and a sequence that hybridizes to one or more detectable probes.

15. The method of claim 14, wherein the detecting step comprises contacting the RCA product with detectable probes and intermediate probes in sequential cycles.

16. The method of claim 1, wherein a circular probe of the plurality of circular probes is provided by ligating a first hairpin probe to a second hairpin probe, any one or both of which comprise one or more ribonucleotides at the 5' and/or the 3' end thereby circularizing the first and second hairpin probes to provide the circular probe.

17. The method of claim 16, wherein:

the first hairpin probe comprises a first loop region, a first stem region, and a first 3' single-stranded region comprising one or more ribonucleotides;

the second hairpin probe comprises a second loop region, a second stem region, and a second 3' single-stranded region that is DNA; and the first 3' single-stranded region or a portion thereof is complementary to the second 3' single-stranded region or a portion thereof.

18. The method of claim 1, wherein the biological sample is a tissue sample.

19. The method of claim 1, wherein the biological sample is embedded in a matrix.

20. A method, comprising:

(a) contacting a biological sample comprising a ribonucleic acid (RNA) molecule with a circular probe, wherein:

the circular probe comprises a stem region, a first loop region, and a second loop region, the stem region comprises (i) a first strand comprising one or more ribonucleotides and (ii) a second strand complementary to the first strand, and a sequence in the first loop region hybridizes to a first sequence in the RNA molecule;

(b) hybridizing a second sequence of the RNA molecule to the first strand of the stem region, wherein:

the second strand is displaced from the first strand, the circular probe hybridizes to at least the first and second sequences in the RNA molecule, and the one or more ribonucleotides in the circular probe hybridize to complementary ribonucleotide(s) in the RNA molecule;

(c) after (b), contacting the biological sample with an RNAse;

(d) performing a rolling circle amplification reaction on the circular probe to generate a rolling circle amplification (RCA) product; and (e) detecting a signal or absence thereof, wherein the signal is associated with the RCA product in the biological sample.

* * * * *